United States Patent
Nakao et al.

(10) Patent No.: US 11,326,163 B2
(45) Date of Patent: May 10, 2022

(54) THERAPEUTIC AGENT FOR FIBROSIS

(71) Applicant: KYORIN PHARMACEUTICAL CO., LTD., Tokyo (JP)

(72) Inventors: Kazuhisa Nakao, Shimotsuga-gun (JP); Junichi Ishiyama, Tokyo (JP); Wataru Ichikawa, Tsukuba (JP); Atsushi Masui, Shimotsuga-gun (JP); Yunike Akasaka, Shimotsuga-gun (JP); Hidekazu Toyofuku, Kurume (JP); Aya Honda, Shimotsuga-gun (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/633,909

(22) PCT Filed: Jul. 30, 2018

(86) PCT No.: PCT/JP2018/028459
§ 371 (c)(1),
(2) Date: Jan. 24, 2020

(87) PCT Pub. No.: WO2019/022257
PCT Pub. Date: Jan. 31, 2019

(65) Prior Publication Data
US 2021/0087556 A1 Mar. 25, 2021

(30) Foreign Application Priority Data
Jul. 28, 2017 (JP) .............................. JP2017-146957

(51) Int. Cl.
A61K 48/00 (2006.01)
C07H 21/04 (2006.01)
C12N 15/113 (2010.01)
A61K 31/7105 (2006.01)
A61K 31/713 (2006.01)

(52) U.S. Cl.
CPC .......... *C12N 15/113* (2013.01); *A61K 31/713* (2013.01); *A61K 31/7105* (2013.01)

(58) Field of Classification Search
CPC .......................... C12N 15/113; C12N 2310/14
See application file for complete search history.

(56) References Cited

U.S. PATENT DOCUMENTS

| | | |
|---|---|---|
| 2004/0097441 A1 | 5/2004 | Dobie |
| 2006/0094061 A1 | 5/2006 | Brys et al. |
| 2007/0083334 A1 | 4/2007 | Mintz et al. |
| 2012/0010271 A1 | 1/2012 | Ohgi et al. |
| 2012/0035246 A1 | 2/2012 | Ohgi et al. |
| 2014/0100362 A1 | 4/2014 | Hamasaki et al. |
| 2014/0171486 A1 | 6/2014 | Ohgi et al. |
| 2014/0171633 A1 | 6/2014 | Ohgi et al. |
| 2014/0206856 A1 | 7/2014 | Aoki et al. |
| 2014/0329886 A1 | 11/2014 | Ohgi et al. |
| 2015/0011605 A1 | 1/2015 | Ohgi et al. |
| 2015/0105443 A1 | 4/2015 | Ohgi et al. |
| 2015/0224132 A1 | 8/2015 | Appleman et al. |
| 2016/0003808 A1 | 1/2016 | Janssen et al. |
| 2016/0108400 A1 | 4/2016 | Ohgi et al. |
| 2016/0176810 A1 | 6/2016 | Aoki et al. |
| 2017/0306325 A1 | 10/2017 | Ohgi et al. |

FOREIGN PATENT DOCUMENTS

| | | |
|---|---|---|
| EP | 2436767 A1 | 4/2012 |
| WO | 2004/045527 | 6/2004 |
| WO | 2012/017919 A1 | 2/2012 |
| WO | 2016/108264 A1 | 7/2016 |
| WO | 2016/158809 A1 | 10/2016 |
| WO | 2016/159374 A1 | 10/2016 |

OTHER PUBLICATIONS

Elbashir et al. (The EMBO Journal, vol. 20, No. 23, pp. 6877-6888, 2001).*
Jee et al. (Cancer Letters, 335, 2013, 175-182).*
Notification of Transmittal of Translation of the International Preliminary Report on Patentability (Form PCT/IB/338) issued in counterpart International application No. PCT/JP2018/028459 dated Feb. 6, 2020 with Forms PCT/IB/373 and PCT/ISA/237. (7 pages).
International Search Report dated Oct. 9, 2018, issued in counterpart application No. PCT/JP2018/028459. (1 page).
Tatsuya Tsukui, et al., "Qualitative Rather than Quantitative Changes are Hallmarks of Fibroblasts in Bleomycin-Induced Pulmonary Fibrosis", Elsevier, The American Journal of Pathology, vol. 183, No. 3, Cardiovascular, Pulmonary, and Renal Pathology, Sep. 2013, p. 758-p773 (16 pages).
Miriam Barrios-Rodiles, et al., "High-Throughput Mapping of aDynamic Signaling Network in Mammalian Cells", Science vol. 307, No. 11, Mar. 2005, p. 1621-p. 1625 (6 pages).
Miriam Barrios-Rodiles, et al., "High-Throughput Mapping of a Dynamic Signaling Network in Mammalian Cells", Science Supporting Online Material, 2005 (27 pages).
Christopher Belham, et al., "A Mitotic Cascade of NIMA Family Kinases", The Journal of Biological Chemistry vol. 278, No. 37, Sep. 12, 2003, p. 34897-p. 34909 (14 pages).
Christopher Belham, et al., "Identification of the NIMA family kinases NEK6/7 as regulators of the p70 ribosomal S6 kinase", Current Biology vol. 11 No. 15, Aug. 7, 2001, p. 1155-p. 1167 (13 pages).
M Teresa Bertran, et al., "Nek9 is a Plk1-activated kinase that controls early centrosome separation through Nek6/7 and Eg5", The EMBO Journal vol. 30 No. 13, 2011, p. 2634-p. 2647 (14 Pages).

(Continued)

*Primary Examiner* — Amy H Bowman
(74) *Attorney, Agent, or Firm* — Wenderoth, Lind & Ponack, L.L.P.

(57) ABSTRACT

Disclosed is a phosphorylation inhibitor of SMAD2/3 protein or a therapeutic agent for fibrosis which contains as an active ingredient, a nucleic acid that suppresses NEK6 (NIMA-related serine/threonine kinase 6) gene expression.

7 Claims, 21 Drawing Sheets
Specification includes a Sequence Listing.

(56) References Cited

OTHER PUBLICATIONS

Zhouyan Bian., et al., "Never in Mitosis Gene A Related Kinase-6 Attenuates Pressure Overload-Induced Activation of the Protein Kinase B Pathway and Cardiac Hypertrophy", PLOS ONE vol. 9 No. 4, Apr. 2014 (8 Pages).
Jian Chen, et al., "Interaction of Pin1 with Nek6 and characterization of their expression correlation in Chinese hepatocellular carcinoma patients", Biochemical and Biophysical Research Communications vol. 341, 2006, p. 1059-p. 1065 (7 pages).
Erez Feige, Benny Motro, "The related murine kinases, Nek6 and Nek7, display distinct patterns of expression", Mechanisms of Development vol. 110, 2002, p. 219-p. 223 (5 Pages).
Andrew M. Fry , Laura O'Regan, Sarah R. Sabir and Richard Bayliss, "Cell cycle regulation by the NEK family of protein kinases", Journal of Cell Science vol. 125 No. 19, Oct. 2012, p. 4423-p. 4433 (11 pages).
Tamanna Haq, et al., "Mechanistic basis of Nek7 activation through Nek9 binding and induced dimerization", Nature Communications DOI: 10.1038/ncomms9771, 2015 (12 Pages).
Hye Jin Jee, et al., "Nek6 overexpression antagonizes p53-induced senescence in human cancer cells", Cell Cycle vol. 9 Issue 23, Dec. 1, 2010, p. 4703-p. 4710 (8 pages).
Hye Jin Jee, et al., "Nek6 suppresses the premature senescence of human cancer cells induced by camptothecin and doxorubicin treatment", Biochemical and Biophysical Research Communications vol. 408, 2011, p. 669-p. 673 (5 pages).
Young Jin Jeon, et al., "Role of NEK6 in Tumor Promoter-induced Transformation in JB6 C141 Mouse Skin Epidermal Cells", The Journal of Biological Chemistry vol. 285, No. 36,, Sep. 3, 2010, p. 28126-p. 28133 (9 pages).
Jie Zuo, et al., "An inhibitory role of NEK6 in TGF?/Smad signaling pathway", BMB Reports vol. 48 No. 8, 2015, p. 473-p. 478 (6 pages).
Jinsuk Kang, et al., "Dynamic Regulation of Oct1 during Mitosis by Phosphorylation and Ubiquitination", PLoS ONE vol. 6| Issue 8, Aug. 2011 (14 pages).
Sunghwan Kim, Seongjae Kim and Kunsoo Rhee vol. 124 No. 22, "NEK7 is essential for centriole duplication and centrosomal accumulation of pericentriolar material proteins in interphase cells", Journal of Cell Science , 2011, p. 3760-p. 3770 (13 pages).
Eun Jeoung Lee , Sung Hee Hyun , Jaesun Chun , Sang Sun Kang, "Human NIMA-related kinase 6 is one of the Fe65 WW domain binding proteins", Biochemical and Biophysical Research Communications vol. 358, 2007, p. 783-p. 788 (6 pages).
Jose M Lizcano, et al., "Molecular basis for the substrate specificity of NEK6: evidence that it does not phosphorylate the hydrophobic motif of S6K and SGK in vivo.", J. Biol. Chem. doi: 10.1074/jbc. M202042200, 2002 (39 Pages).
Gabriela Vaz Meirelles Daniel Carlos Ferreira Lanza, et al., "Characterization of hNek6 Interactome Reveals an Important Role for its Short N-Terminal Domain and Colocalization with Proteins at the Centrosome", Journal of Proteome Research vol. 9, No. 12, 2010, p. 6298-p. 6316 (19 Pages).
Shigeru Minoguchi, Mayu Minoguchi, and Akihiko Yoshimura, "Differential control of the NIMA-related kinases,Nek6 and Nek7, by serum stimulation", Biochemical and Biophysical Research Communications vol. 301, 2003, p. 899-p. 906 (8 pages).
Rounak Nassirpour, et al., "Nek6 Mediates Human Cancer Cell Transformation and is a Potential Cancer Therapeutic Target", Molecular Cancer Research 8(5), May 2010, p. 717-p. 728 (13 pages).

Shyam Nyati, et al., "The kinase activity of the Ser/Thr kinase BUB1 promotes TGF-b signaling", Science Signaling vol. 8 Issue 358, Jan. 2015 (12 Pages).
Laura O'Regan, Joelle Blot and Andrew M Fry, "Mitotic regulation by NIMA-related kinases", Cell Division doi:10.1186/1747-1028-2-25, Aug. 2007 (12 pages).
Laura O'Regan and Andrew M. Fry, "The Nek6 and Nek7 Protein Kinases are Required for Robust MitoticSpindle Formation and Cytokinesis", Molecular and Cellular Biology vol. 29, No. 14, Jul. 2009, p. 3975-p. 3990 (17 pages).
Joseph Rapley, et al., "The NIMA-family kinase Nek6 phosphorylates the kinesin Eg5 at a novel site necessary for mitotic spindle formation", Journal of Cell Science vol. 121 No. 23, Sep. 2008, p. 3912-p. 3921 (10 pages).
Mark W. Richards Laura O'Regan, et al., "An Autoinhibitory Tyrosine Motif in the Cell-Cycle-Regulated Nek7 Kinase is Released through Binding of Nek9", Molecular Cell vol. 36, Nov. 25, 2009, p. 560-p. 570 (11 pages).
Joan Roig, et al., "Nercc1, a mammalian NIMA-family kinase, binds the Ran GTPase and regulates mitotic progression", Genes & Development: vol. 16, 2002, p. 1640-p. 1658 (20 pages).
Sara Sdelci, et al., "Nek9 Phosphorylation of NEDD1/GCP-WD Contributes to Plk1 Control of g-Tubulin Recruitment to the Mitotic Centrosome", Current Biology vol. 22, Aug. 21, 2012, p. 1516-p. 1523 (8 pages).
Hexin Shi, et al., "NLRP3 activation and mitosis are mutually exclusive events coordinated by NEK7, a new inflammasome component", nature immunology doi:10.1038/ni.3333, Dec. 2015 (12 pages).
A Takeno, et al., "Integrative approach for differentially overexpressed genes in?gastric cancer by combining large-scale gene expression profiling and network analysis", British Journal of Cancer vol. 99, 2008, p. 1307-p. 1315 (9 pages).
Vladimir La? zeti'c and David S. Fay, "Conserved Ankyrin Repeat Proteins and Their NIMA Kinase Partners Regulate Extracellular Matrix Remodeling and Intracellular Trafficking in Caenorhabditis elegans", Genetics, vol. 205, Jan. 2017, p. 273-p. 293 (36 pages).
Min-Jean Yin, Lihua Shao, David Voehringer, Tod Smeal, and Bahija Jallal, "The Serine/Threonine Kinase Nek6 is Required for Cell Cycle Progression through Mitosis", The Journal of Biological Chemistry vol. 278, No. 52, 2003, p. 52454-p. 52460 (8 pages).
Min-Young Lee, et al., "Nek6 is involved in G2/M phase cell cycle arrest through DNA damage-induced phosphorylation", Cell Cycle vol. 7 Issue 17, Sep. 2008, p. 2705-p. 2709 (10 pages).
Biao Zhang, et al., "Never in mitosis gene A?related kinase 6 promotes cell proliferation of hepatocellular carcinoma via cyclin B modulation", Oncology Letters vol. 8, 2014, p. 1163-p. 1168 (6 pages).
Atish D. Choudhury, et al., "Castration Resistance in Prostate Cancer is mediated by the Kinase NEK6", Cancer Research vol. 77 No. 3, Feb. 2017, p. 753-p. 765 (18 pages).
Hye Jin Jee, et al., "The inhibition of Nek6 function senstitizes human cancer cells to premature senescence upon serum reduction or anticancer drug treatment.", Cancer Letters vol. 335, No. 1, 2013, p. 175-p. 182 (8 pages).
Marta De Donato, et al., "Identification and antitumor activity of a novel inhibitor of the NIMA-related kinase NEK6.", Scientific Reports vol. 8, No. 1, 2018, p. 16047 (13 pages).
Moniz et al., "Nek family of kinases in cell cycle, checkpoint control and cancer", Cell Division, 2011, vol. 6, No. 18, pp. 1-10.

* cited by examiner

Fig.1 atggcaggacagcccggccacatgcccatggagggagttccaacaacctctgccacaccctggggcctgtgcatcctcctga
                              KB-001 cccacagaggcatcccaacacgctgtcttttcgctgctcgctggcggacttccagatcgaaaagaagataggccgaggacagt tcagcgaggtgtacaaggccacctgcctgctggacaggaagacagtggctctgaagaaggtgcagatctttgagatgatgg acgccaaggccgagccagtactgtgtcaaggagatcggcctcttgaagcaactgaaccacccaaatatcatcaagtatttgga
         KB-002 ctcgtttatcgaagacaacgagctgaacattgtgctggagttggctgacgcaggggacctctcgcagatgatcaagtacttta agaagcagaagcggctcatcccggagaggacagtatggaagtacttgtgcagctgtgcagcgccgtggagcacatgcattc
                        Stealth                                    KB-003 acgcccgggtgatgcaccgagacatcaagcctgccaacgtgttcatcacagccacggggcgtcgtgaagctcggtgaccttggtc tgggccgcttcttcagctctgagaccaccgcagcccactccctagtggggacgccctactacatgtcaccggagaggatccatg agaacggctacaacttcaagtccgacatctggtccctgggctgtctgctgtacgagatggcagcctccagagcccttctatg gagataagatgaatctcttctcccctgtgccagaagatcgagcagtgtgactaccccccactcccggggagccactaccgag
  KB-004 aagttacgagaactggtcagcatgtgcatctgcctgacccccaccagagaacctgacatcgratacgtgcaccaggtggcca
                                    KB-005 agcagatgcacatctggatgtccagcacctga

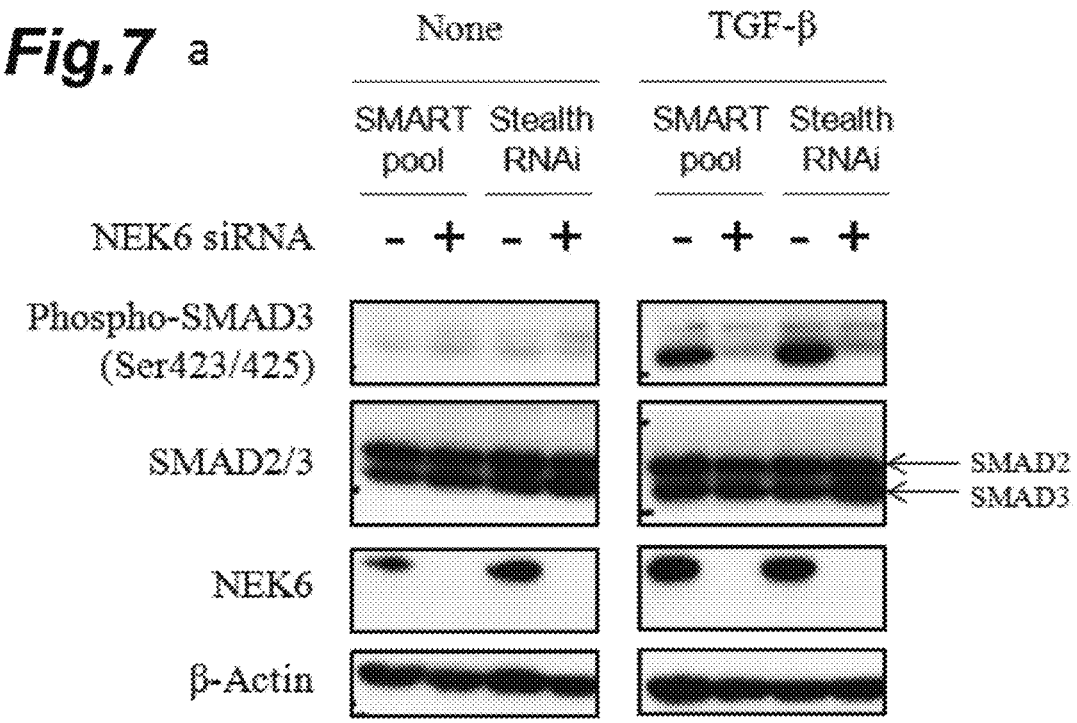
*Fig.7* a
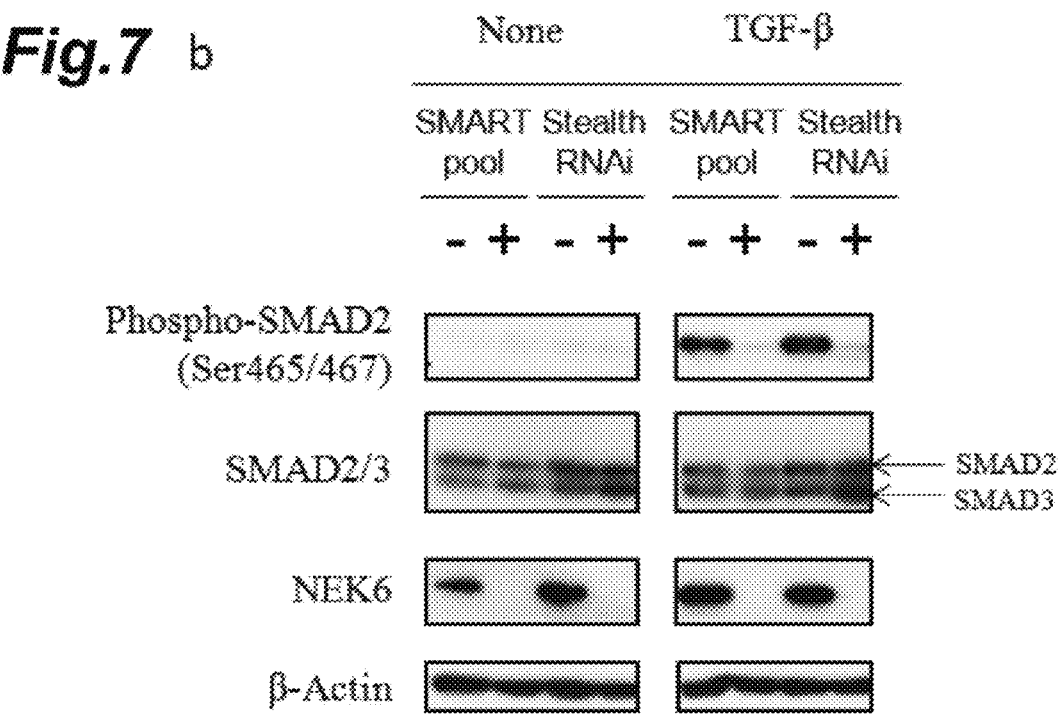
*Fig.7* b

*Fig.8* a
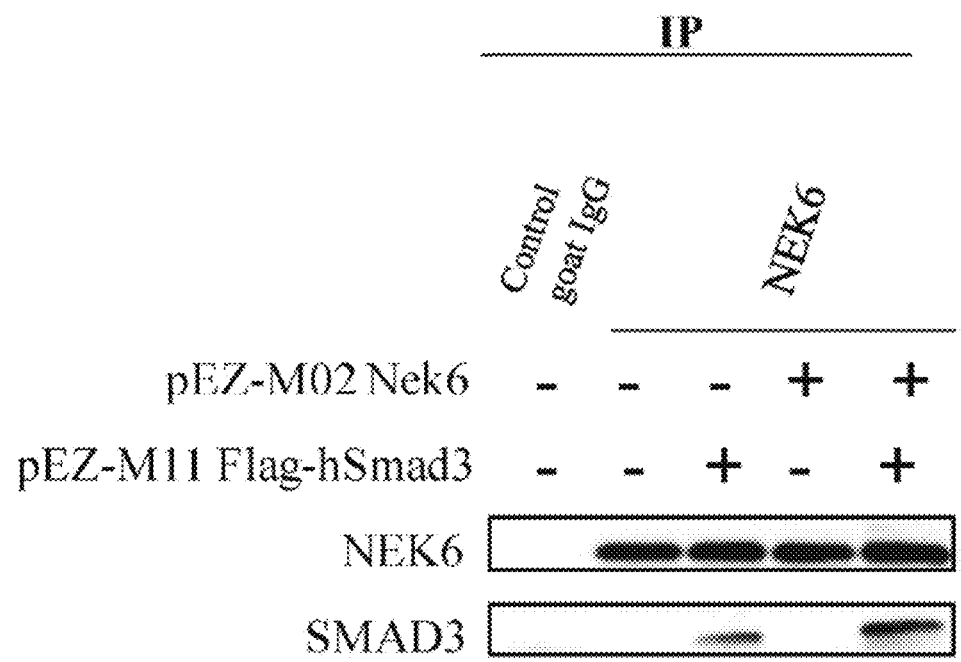
*Fig.8* b
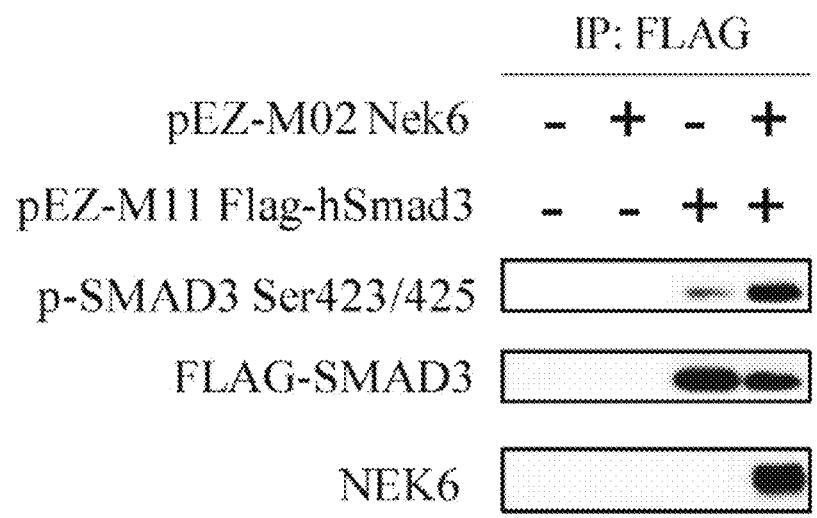

*Fig.10* a
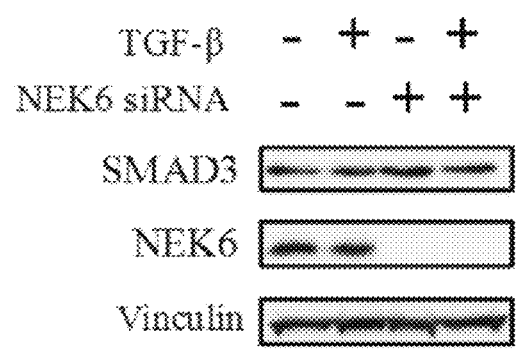
*Fig.10* b
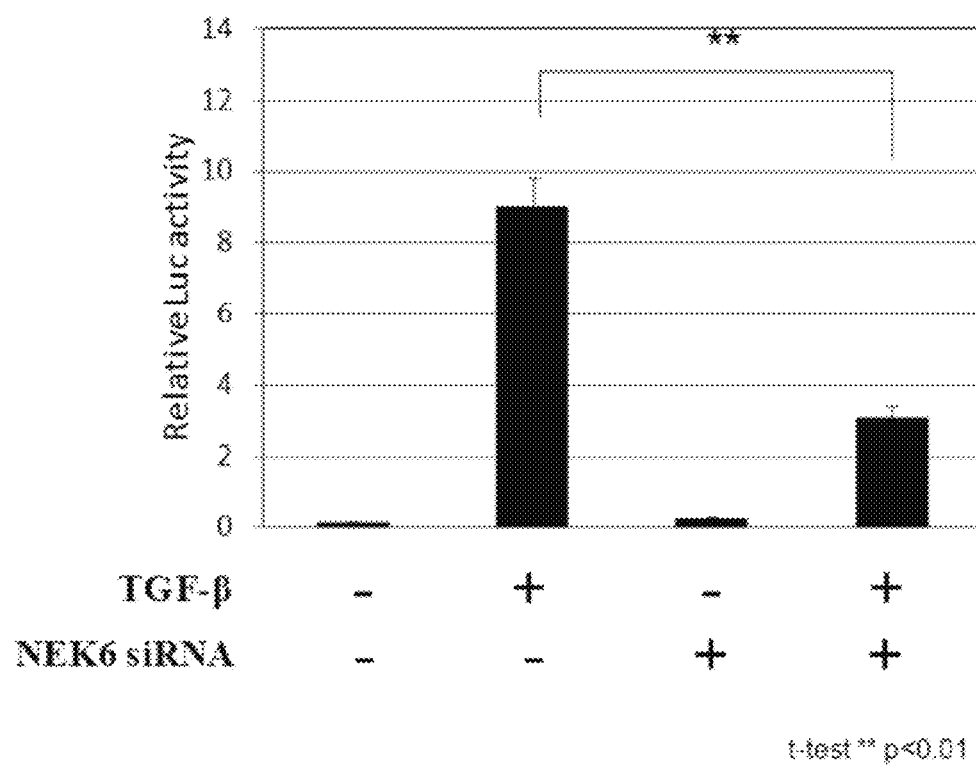

*Fig.15* a 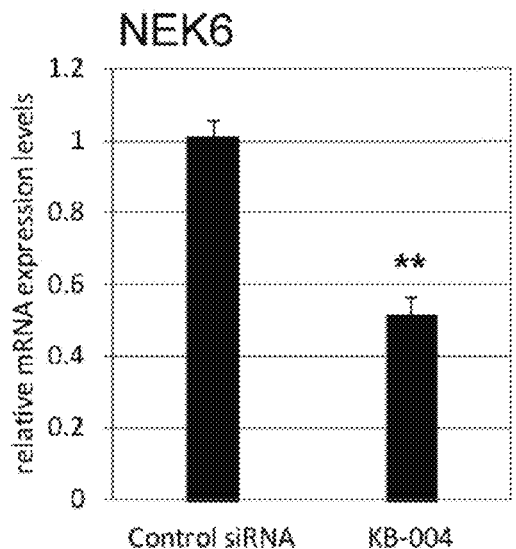
*Fig.15* b 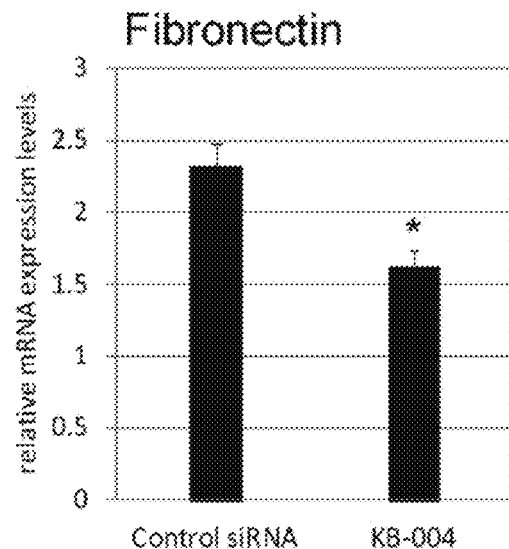
*Fig.15* c 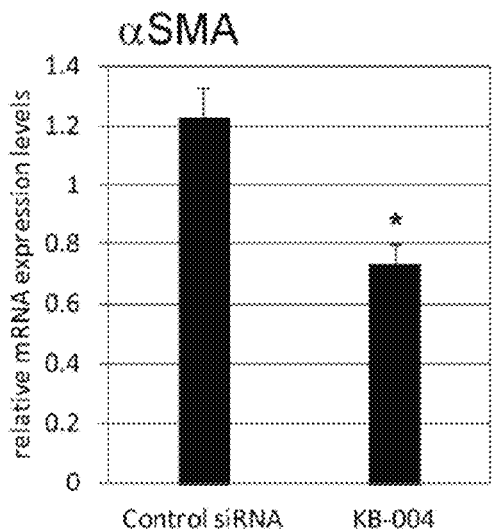
t-test *p<0.05, ** p<0.01

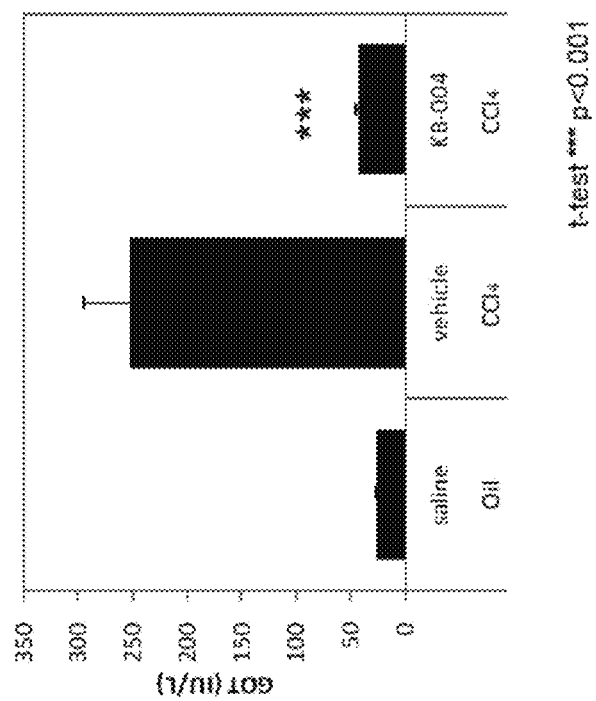
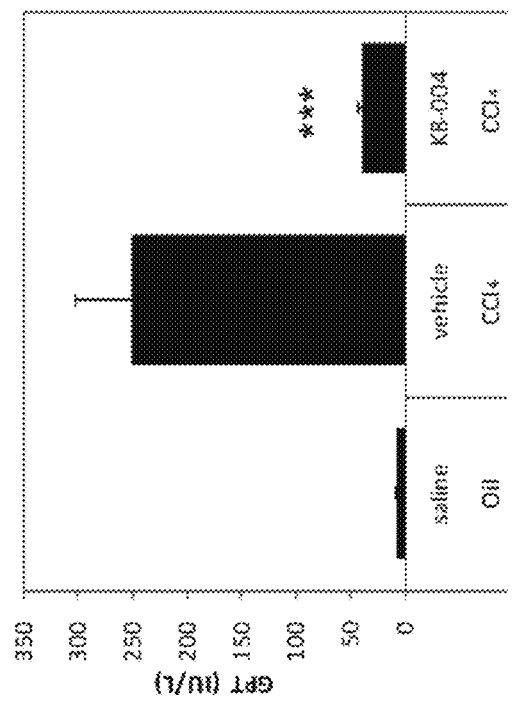
Fig. 17 a
Fig. 17 b

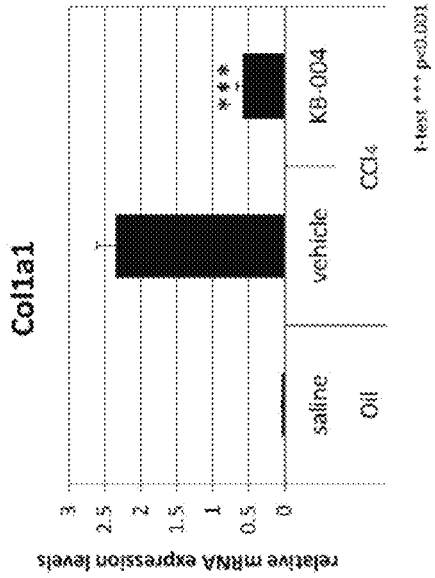
*Fig. 19* a
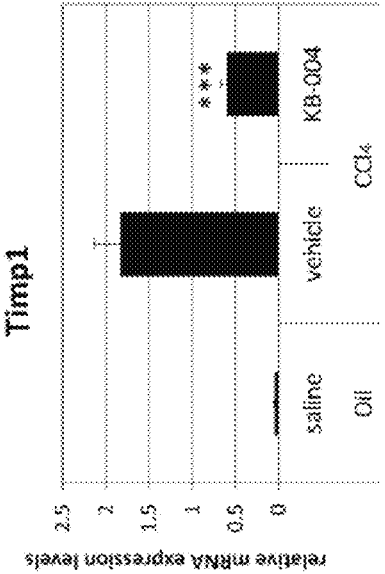
*Fig. 19* b
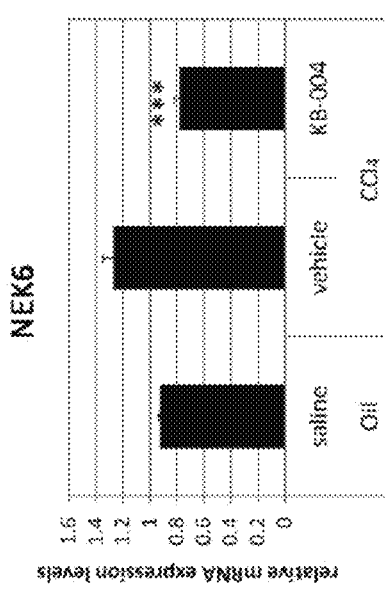
*Fig. 19* c
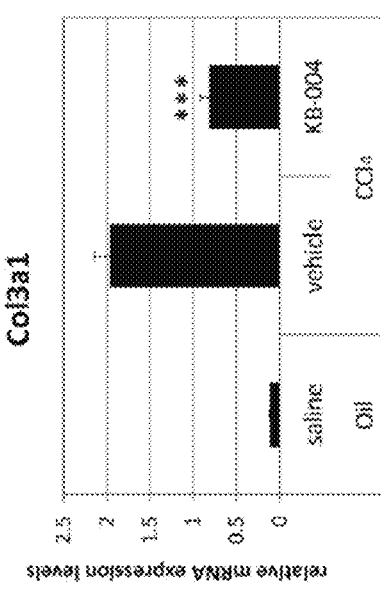
*Fig. 19* d

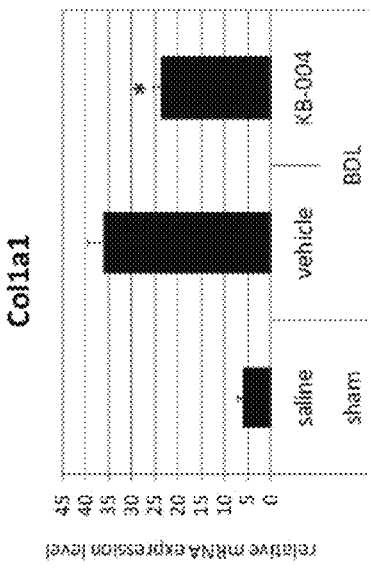
*Fig. 20* b
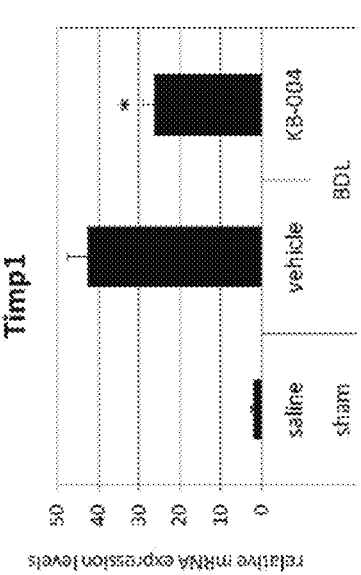
*Fig. 20* d
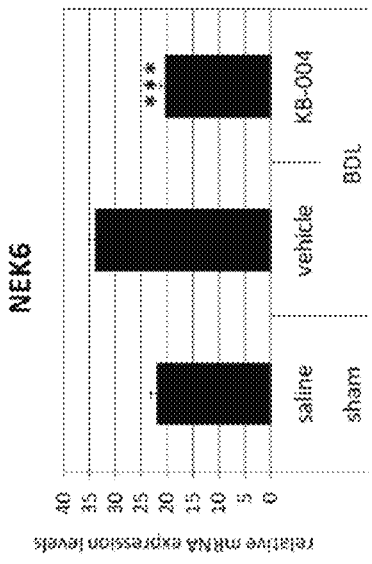
*Fig. 20* a
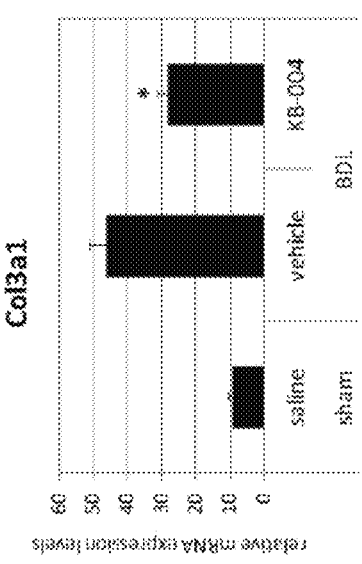
*Fig. 20* c

SEQUENCE LISTING

```
<160> NUMBER OF SEQ ID NOS: 61

<210> SEQ ID NO 1
<211> LENGTH: 15
<212> TYPE: RNA
<213> ORGANISM: Artificial
<220> FEATURE:
<223> OTHER INFORMATION: Synthetic RNA

<400> SEQUENCE: 1
agagguuguu ggaac                                                      15

<210> SEQ ID NO 2
<211> LENGTH: 15
<212> TYPE: RNA
<213> ORGANISM: Artificial
<220> FEATURE:
<223> OTHER INFORMATION: Synthetic RNA
```

```
<400> SEQUENCE: 2
ccuugacaca guccu                                                          15

<210> SEQ ID NO 3
<211> LENGTH: 15
<212> TYPE: RNA
<213> ORGANISM: Artificial
<220> FEATURE:
<223> OTHER INFORMATION: Synthetic RNA

<400> SEQUENCE: 3
cgugaaugca ugugc                                                          15

<210> SEQ ID NO 4
<211> LENGTH: 15
<212> TYPE: RNA
<213> ORGANISM: Artificial
<220> FEATURE:
<223> OTHER INFORMATION: Synthetic RNA

<400> SEQUENCE: 4
ggagaagaga uucau                                                          15

<210> SEQ ID NO 5
<211> LENGTH: 15
<212> TYPE: RNA
<213> ORGANISM: Artificial
<220> FEATURE:
<223> OTHER INFORMATION: Synthetic RNA

<400> SEQUENCE: 5
guauccgaug ucagg                                                          15

<210> SEQ ID NO 6
<211> LENGTH: 15
<212> TYPE: RNA
<213> ORGANISM: Artificial
<220> FEATURE:
<223> OTHER INFORMATION: Synthetic RNA

<400> SEQUENCE: 6
guuccaacaa ccucu                                                          15

<210> SEQ ID NO 7
<211> LENGTH: 15
<212> TYPE: RNA
<213> ORGANISM: Artificial
<220> FEATURE:
<223> OTHER INFORMATION: Synthetic RNA

<400> SEQUENCE: 7
aggacugugu caagg                                                          15

<210> SEQ ID NO 8
<211> LENGTH: 15
<212> TYPE: RNA
<213> ORGANISM: Artificial
<220> FEATURE:
<223> OTHER INFORMATION: Synthetic RNA

<400> SEQUENCE: 8
gcacaugcau ucacg                                                          15

<210> SEQ ID NO 9
```

```
<211> LENGTH: 15
<212> TYPE: RNA
<213> ORGANISM: Artificial
<220> FEATURE:
<223> OTHER INFORMATION: Synthetic RNA

<400> SEQUENCE: 9
augaaucucu ucucc                                                        15

<210> SEQ ID NO 10
<211> LENGTH: 15
<212> TYPE: RNA
<213> ORGANISM: Artificial
<220> FEATURE:
<223> OTHER INFORMATION: Synthetic RNA

<400> SEQUENCE: 10
ccugacaucg gauac                                                        15

<210> SEQ ID NO 11
<211> LENGTH: 19
<212> TYPE: RNA
<213> ORGANISM: Artificial
<220> FEATURE:
<223> OTHER INFORMATION: Synthetic RNA

<400> SEQUENCE: 11
agagguuguu ggaacuccc                                                    19

<210> SEQ ID NO 12
<211> LENGTH: 19
<212> TYPE: RNA
<213> ORGANISM: Artificial
<220> FEATURE:
<223> OTHER INFORMATION: Synthetic RNA

<400> SEQUENCE: 12
ccuugacaca guccugccu                                                    19

<210> SEQ ID NO 13
<211> LENGTH: 19
<212> TYPE: RNA
<213> ORGANISM: Artificial
<220> FEATURE:
<223> OTHER INFORMATION: Synthetic RNA

<400> SEQUENCE: 13
cgugaaugca ugugcucca                                                    19

<210> SEQ ID NO 14
<211> LENGTH: 19
<212> TYPE: RNA
<213> ORGANISM: Artificial
<220> FEATURE:
<223> OTHER INFORMATION: Synthetic RNA

<400> SEQUENCE: 14
ggagaagaga uucaucuua                                                    19

<210> SEQ ID NO 15
<211> LENGTH: 19
<212> TYPE: RNA
<213> ORGANISM: Artificial
<220> FEATURE:
<223> OTHER INFORMATION: Synthetic RNA

<400> SEQUENCE: 15
```
guauccgaug ucaggucuc                                                    19

<210> SEQ ID NO 16
<211> LENGTH: 21
<212> TYPE: RNA
<213> ORGANISM: Artificial
<220> FEATURE:
<223> OTHER INFORMATION: Synthetic RNA

<400> SEQUENCE: 16
agagguuguu ggaacucccu c                                                 21

<210> SEQ ID NO 17
<211> LENGTH: 21
<212> TYPE: RNA
<213> ORGANISM: Artificial
<220> FEATURE:
<223> OTHER INFORMATION: Synthetic RNA

<400> SEQUENCE: 17
ccuugacaca guccugccuc g                                                 21

<210> SEQ ID NO 18
<211> LENGTH: 21
<212> TYPE: RNA
<213> ORGANISM: Artificial
<220> FEATURE:
<223> OTHER INFORMATION: Synthetic RNA

<400> SEQUENCE: 18
cgugaaugca ugugcuccac g                                                 21

<210> SEQ ID NO 19
<211> LENGTH: 21
<212> TYPE: RNA
<213> ORGANISM: Artificial
<220> FEATURE:
<223> OTHER INFORMATION: Synthetic RNA

<400> SEQUENCE: 19
ggagaagaga uucaucuuau c                                                 21

<210> SEQ ID NO 20
<211> LENGTH: 21
<212> TYPE: RNA
<213> ORGANISM: Artificial
<220> FEATURE:
<223> OTHER INFORMATION: Synthetic RNA

<400> SEQUENCE: 20
guauccgaug ucaggucucu g                                                 21

<210> SEQ ID NO 21
<211> LENGTH: 23
<212> TYPE: RNA
<213> ORGANISM: Artificial
<220> FEATURE:
<223> OTHER INFORMATION: Synthetic RNA

<400> SEQUENCE: 21
agagguuguu ggaacucccu cca                                               23

<210> SEQ ID NO 22
<211> LENGTH: 23
<212> TYPE: RNA

```
<213> ORGANISM: Artificial
<220> FEATURE:
<223> OTHER INFORMATION: Synthetic RNA

<400> SEQUENCE: 22
ccuugacaca guccugccuc gcc                                              23

<210> SEQ ID NO 23
<211> LENGTH: 23
<212> TYPE: RNA
<213> ORGANISM: Artificial
<220> FEATURE:
<223> OTHER INFORMATION: Synthetic RNA

<400> SEQUENCE: 23
cgugaaugca ugugcuccac ggc                                              23

<210> SEQ ID NO 24
<211> LENGTH: 23
<212> TYPE: RNA
<213> ORGANISM: Artificial
<220> FEATURE:
<223> OTHER INFORMATION: Synthetic RNA

<400> SEQUENCE: 24
ggagaagaga uucaucuuau cuc                                              23

<210> SEQ ID NO 25
<211> LENGTH: 23
<212> TYPE: RNA
<213> ORGANISM: Artificial
<220> FEATURE:
<223> OTHER INFORMATION: Synthetic RNA

<400> SEQUENCE: 25
guauccgaug ucaggucucu ggu                                              23

<210> SEQ ID NO 26
<211> LENGTH: 25
<212> TYPE: RNA
<213> ORGANISM: Artificial
<220> FEATURE:
<223> OTHER INFORMATION: Synthetic RNA

<400> SEQUENCE: 26
ggagagguug uuggaacucc cucca                                            25

<210> SEQ ID NO 27
<211> LENGTH: 25
<212> TYPE: RNA
<213> ORGANISM: Artificial
<220> FEATURE:
<223> OTHER INFORMATION: Synthetic RNA

<400> SEQUENCE: 27
ggccuugaca caguccugcc ucgcc                                            25

<210> SEQ ID NO 28
<211> LENGTH: 25
<212> TYPE: RNA
<213> ORGANISM: Artificial
<220> FEATURE:
<223> OTHER INFORMATION: Synthetic RNA

<400> SEQUENCE: 28
ggcgugaaug caugugcucc acggc                                            25
```

<210> SEQ ID NO 29
<211> LENGTH: 25
<212> TYPE: RNA
<213> ORGANISM: Artificial
<220> FEATURE:
<223> OTHER INFORMATION: Synthetic RNA

<400> SEQUENCE: 29
ggggagaaga gauucaucuu aucuc                                              25

<210> SEQ ID NO 30
<211> LENGTH: 25
<212> TYPE: RNA
<213> ORGANISM: Artificial
<220> FEATURE:
<223> OTHER INFORMATION: Synthetic RNA

<400> SEQUENCE: 30
ggguauccga ugucaggucu cuggu                                              25

<210> SEQ ID NO 31
<211> LENGTH: 48
<212> TYPE: RNA
<213> ORGANISM: Artificial
<220> FEATURE:
<223> OTHER INFORMATION: Synthetic RNA

<400> SEQUENCE: 31
gagggaguuc caacaaccuc uccggagagg uuguuggaac ucccucca                     48

<210> SEQ ID NO 32
<211> LENGTH: 48
<212> TYPE: RNA
<213> ORGANISM: Artificial
<220> FEATURE:
<223> OTHER INFORMATION: Synthetic RNA

<400> SEQUENCE: 32
cgaggcagga cugugucaag gccggccuug acacaguccu gccucgcc                     48

<210> SEQ ID NO 33
<211> LENGTH: 48
<212> TYPE: RNA
<213> ORGANISM: Artificial
<220> FEATURE:
<223> OTHER INFORMATION: Synthetic RNA

<400> SEQUENCE: 33
cguggagcac augcauucac gccggcguga augcaugugc uccacggc                     48

<210> SEQ ID NO 34
<211> LENGTH: 48
<212> TYPE: RNA
<213> ORGANISM: Artificial
<220> FEATURE:
<223> OTHER INFORMATION: Synthetic RNA

<400> SEQUENCE: 34
gauaagauga aucucuucuc cccggggaga agagauucau cuuaucuc                     48

<210> SEQ ID NO 35
<211> LENGTH: 48
<212> TYPE: RNA
<213> ORGANISM: Artificial
<220> FEATURE:

```
<223> OTHER INFORMATION: Synthetic RNA

<400> SEQUENCE: 35
cagagaccug acaucggaua cccggguauc cgaugucagg ucucuggu                    48

<210> SEQ ID NO 36
<211> LENGTH: 25
<212> TYPE: RNA
<213> ORGANISM: Artificial
<220> FEATURE:
<223> OTHER INFORMATION: Synthetic RNA

<400> SEQUENCE: 36
ggcuuuucga ucuggaaguc cgcca                                             25

<210> SEQ ID NO 37
<211> LENGTH: 25
<212> TYPE: RNA
<213> ORGANISM: Artificial
<220> FEATURE:
<223> OTHER INFORMATION: Synthetic RNA

<400> SEQUENCE: 37
ggucuuuucg aucuggaagu ccgcc                                             25

<210> SEQ ID NO 38
<211> LENGTH: 25
<212> TYPE: RNA
<213> ORGANISM: Artificial
<220> FEATURE:
<223> OTHER INFORMATION: Synthetic RNA

<400> SEQUENCE: 38
ggcuucuuuu cgaucuggaa guccg                                             25

<210> SEQ ID NO 39
<211> LENGTH: 25
<212> TYPE: RNA
<213> ORGANISM: Artificial
<220> FEATURE:
<223> OTHER INFORMATION: Synthetic RNA

<400> SEQUENCE: 39
gggaagagau ucaucuuauc uccau                                             25

<210> SEQ ID NO 40
<211> LENGTH: 25
<212> TYPE: RNA
<213> ORGANISM: Artificial
<220> FEATURE:
<223> OTHER INFORMATION: Synthetic RNA

<400> SEQUENCE: 40
ggagauucau cuuaucucca uagaa                                             25

<210> SEQ ID NO 41
<211> LENGTH: 23
<212> TYPE: RNA
<213> ORGANISM: Artificial
<220> FEATURE:
<223> OTHER INFORMATION: Synthetic RNA

<400> SEQUENCE: 41
gcggacuucc agaucgaaaa gcc                                               23
```

```
<210> SEQ ID NO 42
<211> LENGTH: 23
<212> TYPE: RNA
<213> ORGANISM: Artificial
<220> FEATURE:
<223> OTHER INFORMATION: Synthetic RNA

<400> SEQUENCE: 42
cggacuucca gaucgaaaag acc                                              23

<210> SEQ ID NO 43
<211> LENGTH: 23
<212> TYPE: RNA
<213> ORGANISM: Artificial
<220> FEATURE:
<223> OTHER INFORMATION: Synthetic RNA

<400> SEQUENCE: 43
gacuuccaga ucgaaaagaa gcc                                              23

<210> SEQ ID NO 44
<211> LENGTH: 23
<212> TYPE: RNA
<213> ORGANISM: Artificial
<220> FEATURE:
<223> OTHER INFORMATION: Synthetic RNA

<400> SEQUENCE: 44
ggagauaaga ugaaucucuu ccc                                              23

<210> SEQ ID NO 45
<211> LENGTH: 23
<212> TYPE: RNA
<213> ORGANISM: Artificial
<220> FEATURE:
<223> OTHER INFORMATION: Synthetic RNA

<400> SEQUENCE: 45
cuauggagau aagaugaauc ucc                                              23

<210> SEQ ID NO 46
<211> LENGTH: 48
<212> TYPE: RNA
<213> ORGANISM: Artificial
<220> FEATURE:
<223> OTHER INFORMATION: Synthetic RNA

<400> SEQUENCE: 46
ggagauaaga ugaaucucuu cccgggaaga gauucaucuu aucccau                    48

<210> SEQ ID NO 47
<211> LENGTH: 48
<212> TYPE: RNA
<213> ORGANISM: Artificial
<220> FEATURE:
<223> OTHER INFORMATION: Synthetic RNA

<400> SEQUENCE: 47
cuauggagau aagaugaauc uccggagauu caucuuaucu ccauagaa                   48

<210> SEQ ID NO 48
<211> LENGTH: 48
<212> TYPE: RNA
<213> ORGANISM: Artificial
<220> FEATURE:
<223> OTHER INFORMATION: Synthetic RNA
```

```
<400> SEQUENCE: 48
gcggacuucc agaucgaaaa gccggcuuuu cgaucuggaa guccgcca                  48

<210> SEQ ID NO 49
<211> LENGTH: 48
<212> TYPE: RNA
<213> ORGANISM: Artificial
<220> FEATURE:
<223> OTHER INFORMATION: Synthetic RNA

<400> SEQUENCE: 49
cggacuucca gaucgaaaag accggucuuu ucgaucugga aguccgcc                  48

<210> SEQ ID NO 50
<211> LENGTH: 48
<212> TYPE: RNA
<213> ORGANISM: Artificial
<220> FEATURE:
<223> OTHER INFORMATION: Synthetic RNA

<400> SEQUENCE: 50
gacuuccaga ucgaaaagaa gccggcuucu uuucgaucug gaaguccg                  48

<210> SEQ ID NO 51
<211> LENGTH: 19
<212> TYPE: RNA
<213> ORGANISM: Artificial
<220> FEATURE:
<223> OTHER INFORMATION: Synthetic RNA

<400> SEQUENCE: 51
cuguccucgg ccuaucuuc                                                  19

<210> SEQ ID NO 52
<211> LENGTH: 19
<212> TYPE: RNA
<213> ORGANISM: Artificial
<220> FEATURE:
<223> OTHER INFORMATION: Synthetic RNA

<400> SEQUENCE: 52
uauuugggug guucaguug                                                  19

<210> SEQ ID NO 53
<211> LENGTH: 19
<212> TYPE: RNA
<213> ORGANISM: Artificial
<220> FEATURE:
<223> OTHER INFORMATION: Synthetic RNA

<400> SEQUENCE: 53
caacuccagc acaauguuc                                                  19

<210> SEQ ID NO 54
<211> LENGTH: 19
<212> TYPE: RNA
<213> ORGANISM: Artificial
<220> FEATURE:
<223> OTHER INFORMATION: Synthetic RNA

<400> SEQUENCE: 54
uacuugauca ucugcgaga                                                  19

<210> SEQ ID NO 55
<211> LENGTH: 24
```

-continued

<212> TYPE: RNA
<213> ORGANISM: Artificial
<220> FEATURE:
<223> OTHER INFORMATION: Synthetic RNA

<400> SEQUENCE: 55
aaguacuucc auacuguccu cucc                                          24

<210> SEQ ID NO 56
<211> LENGTH: 942
<212> TYPE: DNA
<213> ORGANISM: Homo sapiens

<400> SEQUENCE: 56
atggcaggac agcccggcca catgccccat ggagggagtt ccaacaacct ctgccacacc     60
ctggggcctg tgcatcctcc tgacccacag aggcatccca acacgctgtc ttttcgctgc    120
tcgctggcgg acttccagat cgaaaagaag ataggccgag acagttcag cgaggtgtac    180 aaggccacct gcctgctgga caggaagaca gtggctctga agaaggtgca gatctttgag    240
atgatggacg ccaaggcgag gcaggactgt gtcaaggaga tcggcctctt gaagcaactg    300
aaccacccaa atatcatcaa gtatttggac tcgtttatcg aagacaacga gctgaacatt    360
gtgctggagt tggctgacgc aggggacctc tcgcagatga tcaagtactt taagaagcag    420
aagcggctca tcccggagag gacagtatgg aagtactttg tgcagctgtg cagcgccgtg    480
gagcacatgc attcacgccg ggtgatgcac cgagacatca agcctgccaa cgtgttcatc    540
acagccacgg gcgtcgtgaa gctcggtgac cttggtctgg ccgcttctt cagctctgag    600 accaccgcag cccactccct agtggggacg ccctactaca tgtcaccgga gaggatccat    660
gagaacggct acaacttcaa gtccgacatc tggtccctgg gctgtctgct gtacgagatg    720
gcagccctcc agagccccctt ctatggagat aagatgaatc tcttctccct gtgccagaag    780
atcgagcagt gtgactaccc cccactcccc ggggagcact actccgagaa gttacgagaa    840
ctggtcagca tgtgcatctg ccctgacccc caccagagac ctgacatcgg atacgtgcac    900
caggtggcca agcagatgca catctggatg tccagcacct ga                       942

<210> SEQ ID NO 57
<211> LENGTH: 25
<212> TYPE: DNA
<213> ORGANISM: Artificial
<220> FEATURE:
<223> OTHER INFORMATION: Synthetic DNA

<400> SEQUENCE: 57
attggagggc aagtctggtg ccagc                                          25

<210> SEQ ID NO 58
<211> LENGTH: 21
<212> TYPE: DNA
<213> ORGANISM: Artificial
<220> FEATURE:
<223> OTHER INFORMATION: Synthetic DNA

<400> SEQUENCE: 58
cggctaccac atccaaggaa g                                              21

<210> SEQ ID NO 59
<211> LENGTH: 18
<212> TYPE: DNA
<213> ORGANISM: Artificial
<220> FEATURE:

```
<223> OTHER INFORMATION: Synthetic DNA

<400> SEQUENCE: 59
gctggaatta ccgcggct                                              18

<210> SEQ ID NO 60
<211> LENGTH: 48
<212> TYPE: DNA
<213> ORGANISM: Artificial
<220> FEATURE:
<223> OTHER INFORMATION: Synthetic DNA

<400> SEQUENCE: 60
agtatgtcta gactgaagta tgtctagact gaagtatgtc tagactga              48

<210> SEQ ID NO 61
<211> LENGTH: 48
<212> TYPE: RNA
<213> ORGANISM: Artificial
<220> FEATURE:
<223> OTHER INFORMATION: Synthetic RNA

<400> SEQUENCE: 61
gacucguuua ucgaagacaa cccggguugu cuucgauaaa cgagucca              48
```

THERAPEUTIC AGENT FOR FIBROSIS

TECHNICAL FIELD

The present invention relates to a nucleic acid molecule that suppresses NEK6 gene expression and a medicament comprising the nucleic acid molecule as an active ingredient.

BACKGROUND ART

Fibrosis is a disease in which organ function is impaired with excessive accumulation of collagen to lead to irreversible progression, and for example, skin, lung, liver, pancreas, kidney, bone marrow, and the like has been known as the onset organs. Idiopathic pulmonary fibrosis (IPF), which is a type of fibrosis in the lung, is designated as an intractable disease in Japan because, although the disease prevalence is not high as represented by about twenty patients per one hundred thousand population, the post-treatment prognosis is undesirable as represented by the average survival period of 2.5 to 5 years after confirmation of diagnosis.

As therapeutic drugs for IPF, pirfenidon and nintedanib were approved by the Japanese Ministry of Health, Labour and Welfare and have been launched to date. Although both drugs show suppression of decline in vital capacity and prolongation action on progression-free survival and slow down progression of pathological condition, these cannot be deemed to be sufficiently satisfactory as therapeutic efficacies, and development of a therapeutic drug based on a new mechanism has been demanded.

Meanwhile, "NEK6 protein", which is a target of the present invention, is known as one of NIMA-related serine/threonine kinase family involved in control of cell division, but has not drawn attention as a research subject for drug development to date. Although it was reported to have potential as a drug development target for cancer in 2002, there is no specific report that NEK6 protein interacts with SMAD2/3 protein and promotes tissue fibrogenesis.

CITATION LIST

Patent Literature

Patent Literature 1: U.S. Patent Application Publication No. 2004/0097441

SUMMARY OF INVENTION

Technical Problem

The present invention has an object to provide a novel phosphorylation inhibitor of SMAD2/3 protein and a therapeutic agent for fibrosis.

Solution to Problem

The inventors focused attention on finding of enhancement of mRNA level of NEK6 (NIMA-related serine/threonine kinase 6) from analysis with a bleomycin-induced pulmonary fibrosis model, then proceeded with their research, and as a result, found that NEK6 controls SMAD system signaling that contributes to fibrogenesis at the downstream of TGF-β, and arrived at completion of the present invention.

The present invention is as follows:

[1] A phosphorylation inhibitor of SMAD2/3 protein, comprising a nucleic acid that suppresses NEK6 gene expression as an active ingredient;

[2] A therapeutic agent for fibrosis, comprising a nucleic acid that suppresses NEK6 gene expression as an active ingredient;

[3] The therapeutic agent according to [2], wherein the therapeutic agent is for pulmonary fibrosis, hepatic fibrosis, or kidney fibrosis;

[4] A double-strand nucleic acid molecule selected from the group consisting of the following (a), (b), (c), (d), and (e):

(a) a double-strand nucleic acid molecule comprising a 19- to 30-nt guide strand (antisense strand) comprising a sequence shown in SEQ ID NO: 1 at 5' end and a 19- to 30-nt passenger strand (sense strand) comprising a sequence shown in SEQ ID NO: 6 at 3' end or 5' end, (b) a double-strand nucleic acid molecule comprising a 19- to 30-nt guide strand (antisense strand) comprising a sequence shown in SEQ ID NO: 2 at 5' end and a 19- to 30-nt passenger strand (sense strand) comprising a sequence shown in SEQ ID NO: 7 at 3' end or 5' end, (c) a double-strand nucleic acid molecule comprising a 19- to 30-nt guide strand (antisense strand) comprising a sequence shown in SEQ ID NO: 3 at 5' end and a 19- to 30-nt passenger strand (sense strand) comprising a sequence shown in SEQ ID NO: 8 at 3' end or 5' end, (d) a double-strand nucleic acid molecule comprising a 19- to 30-nt guide strand (antisense strand) comprising a sequence shown in SEQ ID NO: 4 at 5' end and a 19- to 30-nt passenger strand (sense strand) comprising a sequence shown in SEQ ID NO: 9 at 3' end or 5' end, and (e) a double-strand nucleic acid molecule comprising a 19- to 30-nt guide strand (antisense strand) comprising a sequence shown in SEQ ID NO: 5 at 5' end and a 19- to 30-nt passenger strand (sense strand) comprising a sequence shown in SEQ ID NO: 10 at 3' end or 5' end;

[5] The double-strand nucleic acid molecule according to [4], wherein 1 to 11 ribonucleotide residues and/or deoxyribonucleotide residues are further added to the 3' end of the guide strand (antisense strand) and/or the passenger strand (sense strand) to form an overhanging end;

[6] A single-strand nucleic acid molecule forming a hairpin RNA structure, wherein the 3' end of the passenger strand (sense strand) and the 5' end of the guide strand (antisense strand) set forth in [4] or [5] are linked to each other via a linker sequence of a nucleotide residue and/or a linker of a non-nucleotide structure, or the 3' end of the guide strand (antisense strand) and the 5' end of the passenger strand (sense strand) set forth in [4] or [5] are linked to each other via a linker sequence of a nucleotide residue and/or a linker of a non-nucleotide structure;

[7] A single-strand nucleic acid molecule of the following (A) or (B), comprising a sequence suppressing NEK6 gene expression selected from SEQ ID NOs: 1 to 5:

(A) the nucleic acid molecule comprising or consisting only of a region (X), a linker region (Lx), and a region (Xc), wherein the region (Xc), the linker region (Lx), and the region (X) are disposed in this order from 5' side to 3' side, wherein the region (Xc) is complementary to the region (X), wherein the linker region (Lx) has a non-nucleotide structure comprising at least one of a pyrrolidine skeleton and a piperidine skeleton, and wherein the region (X) comprises the sequence suppressing the expression;

(B) the nucleic acid molecule comprising a region (Xc), a linker region (Lx), a region (X), a region (Y), a linker region (Ly), and a region (Yc) in this order from 5' side to 3' side, wherein the region (X) and the region (Y) are linked and form an inner region (Z), wherein the region (Xc) is complementary to the region (X), wherein the region (Yc) is complementary to the region (Y), and wherein the linker region (Lx) and/or the linker region (Ly) have a non-nucleotide structure comprising at least one of a pyrrolidine skeleton and a piperidine skeleton, and wherein the inner region (Z) comprises the sequence suppressing the expression;

[8] The single-strand nucleic acid molecule according to [7], wherein the linker region (Lx) and/or (Ly) are represented as the following formula (I):

[Chemical Formula 1]

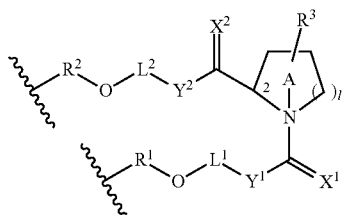

(I)

wherein
$X^1$ and $X^2$ are each independently $H_2$, O, S, or NH;
$Y^1$ and $Y^2$ are each independently a single bond, $CH_2$, NH, O, or S;
$R^3$ is a hydrogen atom or a substituent bound to C-3, C-4, C-5, or C-6 on ring A;
$L^1$ is an alkylene chain having n number of carbon atoms, wherein each of hydrogen atoms on the alkylene carbon atom may or may not be substituted with OH, $OR^a$, $NH_2$, $NHR^a$, $NR^aR^b$, SH, or $SR^a$, or
$L^1$ is a polyether chain in which one or more carbon atoms in the alkylene chain are replaced with one or more oxygen atoms,
with the proviso that if $Y^1$ is NH, O, or S, then an atom in $L^1$ bound to Y is carbon, an atom in $L^1$ bound to $OR^1$ is carbon, and oxygen atoms are not adjacent to each other;
$L^2$ is an alkylene chain having m number of carbon atoms, wherein each of hydrogen atoms on the alkylene carbon atom may or may not be substituted with OH, $OR^c$, $NH_2$, $NHR^c$, $NR^cR^d$, SH, or $SR^c$, or
$L^2$ is a polyether chain in which one or more carbon atoms in the alkylene chain are replaced with one or more oxygen atoms,
with the proviso that if $Y^2$ is NH, O, or S, then an atom in $L^2$ bound to $Y^2$ is carbon, an atom in $L^2$ bound to $OR^2$ is carbon, and oxygen atoms are not adjacent to each other;
$R^a$, $R^b$, $R^c$, and $R^d$ are each independently a substituent or a protecting group;
l is 1 or 2;
m is an integer ranging from 0 to 30;
n is an integer ranging from 0 to 30;
one carbon atom on the ring A other than C-2 may be replaced with nitrogen, oxygen, or sulfur, the ring A may comprise a carbon-carbon double bond or a carbon-nitrogen double bond therein,
the region (Xc) and the region (X) are each bound to the linker region (Lx) via —$OR^1$— or $OR^2$—, and
the region (Yc) and the region (Y) are each bound to the linker region (Ly) via —$OR^1$— or $OR^2$—;
wherein $R^1$ and $R^2$ may or may not be present, and if present, $R^1$ and $R^2$ are each independently a nucleotide residue or the structure (I);

[9] The single-strand nucleic acid molecule according to [7] or [8], wherein X or Z comprises a sequence selected from the group consisting of SEQ ID NOs: 11 to 25;

[10] A method for inhibiting phosphorylation of SMAD2/3 protein, comprising administering a nucleic acid that suppresses NEK6 gene expression to a subject;

[11] A method for treating fibrosis, comprising administering a nucleic acid that suppresses NEK6 gene expression to a subject;

[12] A nucleic acid that suppresses NEK6 gene expression for use in inhibiting the phosphorylation of SMAD2/3 protein;

[13] A nucleic acid that suppresses NEK6 gene expression for use in treating fibrosis;

[14] Use of a nucleic acid that suppresses NEK6 gene expression for producing a phosphorylation inhibitor of SMAD2/3 protein; and

[15] Use of a nucleic acid that suppresses NEK6 gene expression for producing a therapeutic agent for fibrosis.

[16] The use according to [15], wherein the nucleic acid that suppresses NEK6 gene expression is a nucleic acid comprising a sequence suppressing expression in KB-001 to -011 (an underlined part).

Advantageous Effects of Invention

According to the present invention, a novel phosphorylation inhibitor of SMAD2/3 protein and a therapeutic agent for fibrosis can be provided.

BRIEF DESCRIPTION OF DRAWINGS

FIG. 1 is a drawing showing the Coding Sequence region of NEK6 (SEQ ID NO: 56) and a target site of ssPN molecule made in Example 7.

FIG. 7a represents results of Western blot for phosphorylated SMAD3 protein when NEK6 was knockdown. FIG. 7b represents results of Western blot for phosphorylated SMAD2 protein when NEK6 was knockdown.

FIG. 8a represents results of co-immunoprecipitation with an anti-NEK6 antibody. FIG. 8b represents results of co-immunoprecipitation with an anti-FLAG antibody.

FIG. 10a represents results of Western blot when NEK6 was knockdown. FIG. 10b shows luminescence quantity of firefly luciferase when NEK6 was knockdown.

FIG. 15a shows the transcript amounts of NEK6 when NEK6 was knockdown in hepatic stellate cells. FIG. 15b shows the transcript amounts of Fibronectin when NEK6 was knockdown in hepatic stellate cells. FIG. 15c shows the transcript amounts of αSMA gene when NEK6 was knockdown in hepatic stellate cells.

FIG. 17a represents measurement results of serum GPT when NEK6 was knockdown in a $CCl_4$ models. FIG. 17b represents measurement results of serum GOT when NEK6 was knockdown in $CCl_4$ models.

FIG. 19a shows the transcript amounts of NEK6 gene when NEK6 was knockdown in $CCl_4$ models. FIG. 19b shows the transcript amounts of Col1a1 gene when NEK6 was knockdown in $CCl_4$ models. FIG. 19c shows the transcript amounts of Col3a1 gene when NEK6 gene was knockdown in $CCl_4$ models. FIG. 19d shows the transcript amounts of Timp1 gene when NEK6 gene was knockdown in $CCl_4$ models.

FIG. 20a shows the transcript amounts of NEK6 gene when NEK6 was knockdown in BDL models. FIG. 20b shows the transcript amounts of Col1a1 gene when NEK6 was knockdown in BDL models. FIG. 20c shows the transcript amounts of Col3a1 gene when NEK6 gene was knockdown in BDL models. FIG. 20d shows the transcript amounts of Timp1 gene when NEK6 gene was knockdown in BDL models.

FIG. 21a represents a result of the saline administration group not receiving $CCl_4$. FIG. 21b represents a result of the solvent administration group receiving $CCl_4$. FIG. 21c represents a result of the nucleic acid administration group receiving $CCl_4$.

DESCRIPTION OF EMBODIMENTS

Figure 2:
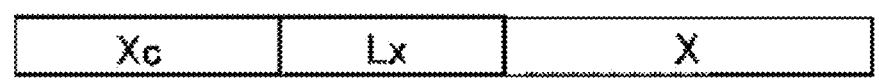
FIGS. 2(A) and 2(B) represent schematic diagrams showing an example of nucleic acid molecules as an active ingredient of a phosphorylation inhibitor of SMAD2/3 protein of the present invention (an ssPN molecule).
Figure 2:
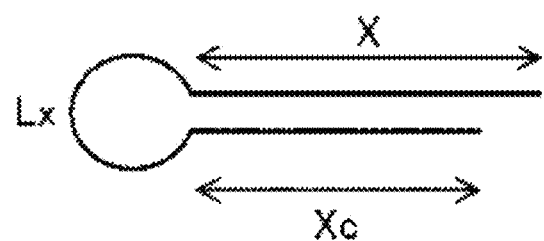

The terms herein used are used to mean as commonly used in the art unless otherwise stated. Additionally, in the present invention, "number of nucleotides" means, for example, "length", and can also be referred to as "nucleotide length". In the present invention, the range of the number of nucleotides discloses, for example, all of the positive integers falling within the range, and as a specific example, the description "1- to 4-nt" means the disclosure of all of "1-, 2-, 3-, 4-nt".

The present invention provides a phosphorylation inhibitor of SMAD2/3 protein, comprising a nucleic acid that suppresses NEK6 gene expression as an active ingredient and a therapeutic agent for fibrosis, comprising the nucleic acid as an active ingredient. Hereinafter, the contents of the present invention will be described in detail.

(1) Nucleic Acids that Suppresses NEK6 Gene Expression

NEK6 protein is one of 11 NIMA-related serine/threonine kinase families involving in control of cell division, and is phosphorylated (activated) in M-phase of cell cycle.

NEK6 gene, which is a target of the present invention, is a mammal-derived gene, and is preferably human-derived gene. Human-derived NEK6 gene has been reported for 7 variants, among which the Coding Sequence region of isoform 2 is shown in FIG. 1 (SEQ ID NO: 56).

The mechanism of suppressing NEK6 gene expression by a nucleic acid molecule is not particularly limited, and is simply required enabling the expression to be down regulated. Suppression of the expression of NEK6 gene can be confirmed by decrease in production of transcription product from NEK6 gene, decrease in production of translation product from NEK6 gene, or decrease in activity of the translation product.

The nucleic acids that suppress NEK6 gene expression include antisense polynucleotides, siRNAs, ssPN molecules, ssNc molecules, miRNAs, ribozymes, and the like of NEK6 mRNA.

The antisense polynucleotides, siRNAs, ssPN molecules, ssNc molecules, and ribozymes can be easily obtained by those skilled in the art on the basis of the nucleotide sequence of human NEK6 gene described above. Preferably, that is a nucleic acid made on the basis of a sequence of the Coding Sequence region of NEK6 isoform 2 (SEQ ID NO: 56).

(2) siRNAs

An siRNA (small interfering RNA), one of nucleic acids that suppress NEK6 gene expression, will be described below.

An siRNA is a nucleic acid molecule that consists of a guide strand (antisense strand) to pair with a target gene, and a passenger strand (sense strand) forming a double strand together with the guide strand. Within a cell, an siRNA is incorporated into a complex referred to as RNA-inducing silencing complex (RISC) that involves Argonaute (AGO) protein as a central core, and then the sense strand is degraded by AGO and the guide strand remains in RISC. A seed region in a guide strand (a 7-nt region at positions 2 to 8 from the 5' end of the guide strand) has been considered to have an important function in recognizing a target sequence, and it has been believed to be preferable to select a seed region specific to a target gene for the purpose of avoiding off-target effect. Accordingly, with regard to the seed region of the nucleic acid as an active ingredient of the present invention, it is also preferable to select a sequence specific to NEK6 gene. Such examples include selecting a nucleic acid containing, as the seed region, a sequence which is complementary to NEK6 gene and is not complementary to NEK7 gene (RefSeq database: NM_133494.2) or in which one or more (e.g., 1 to 3) nucleotides in the region is uncomplementary (mismatched) to NEK7 gene. Furthermore, also with regard to the full length sequence, it is useful, for example, to increase nucleotides which is complementary to NEK6 gene and uncomplementary (mismatched) to NEK7 gene (e.g., 4 or more, preferably 5 to 7 nucleotides), for the purpose of avoiding off-target effect. The number of nucleotides in a sequence suppressing expression contained in a guide strand is, for example, 15 to 30, preferably 19 to 25, more preferably 19 to 23, yet preferably 21, 22, 23, and particularly preferably 23.

The sequence suppressing expression described above may further have an additional sequence at the 3' side to form an overhanging end. The number of nucleotides in the additional sequence described above is, for example, 1 to 11, and preferably 1 to 4. The additional sequence may ribonucleotide residues or deoxyribonucleotide residues.

The number of nucleotides in the guide strand is, for example, 19- to 50-nt, preferably 19- to 30-nt, more preferably 19- to 25-nt, yet preferably 19- to 23-nt, yet more preferably 21-, 22-, 23-, and particularly preferably 23-nt.

The number of nucleotides in the passenger strand is, for example, 19- to 50-nt, preferably 19- to 30-nt, more preferably 19- to 25-nt, yet preferably 19- to 23-nt, yet more preferably 21-, 22-, 23-nt, and particularly preferably 21-nt.

In the passenger strand, a region showing complementarity to the guide strand is, for example, 19- to 50-nt, preferably 19- to 30-nt, more preferably 19- to 25-nt, and yet preferably 19- to 23-nt in length. The region may further have an additional sequence at the 3' side. The number of nucleotides in the additional sequence is, for example, 1- to 11-nt, and preferably 1- to 4-nt, and the additional sequence may be of ribonucleotide residues or deoxyribonucleotide residues. The passenger strand, for example, may be complementary to the region showing complementarity to the guide strand, or may have one or several nucleotides which are uncomplementary, but it is preferable to be complementary. The one nucleotide or several nucleotides means, for example, 1- to 3-nt, and preferably 1-nt or 2-nt.

An siRNA that suppresses NEK6 gene expression can be obtained on the basis of cDNA sequence information of NEK6 gene, for example, according to a siRNA-designing system such as siSNIPER®, or siDirect® for drug discovery/diagnostic research.

It is preferable NEK6 siRNA be an siRNA that specifically acts on NEK6, and examples include double-strand nucleic acids as follows:
(a) a double-strand nucleic acid molecule comprising a 19- to 30-nt guide strand (antisense strand) comprising a sequence shown in SEQ ID NO: 1 at the 5' end and a 19- to 30-nt passenger strand (sense strand) comprising a sequence shown in SEQ ID NO: 6 at the 3' end or the 5' end,
(b) a double-strand nucleic acid molecule comprising a 19- to 30-nt guide strand (antisense strand) comprising a sequence shown in SEQ ID NO: 2 at the 5' end and a 19- to 30-nt passenger strand (sense strand) comprising a sequence shown in SEQ ID NO: 7 at the 3' end or the 5' end,
(c) a double-strand nucleic acid molecule comprising a 19- to 30-nt guide strand (antisense strand) comprising a sequence shown in SEQ ID NO: 3 at the 5' end and a 19- to 30-nt passenger strand (sense strand) comprising a sequence shown in SEQ ID NO: 8 at the 3' end or the 5' end,
(d) a double-strand nucleic acid molecule comprising a 19- to 30-nt guide strand (antisense strand) comprising a sequence shown in SEQ ID NO: 4 at the 5' end and a 19- to 30-nt passenger strand (sense strand) comprising a sequence shown in SEQ ID NO: 9 at the 3' end or the 5' end,
(e) a double-strand nucleic acid molecule comprising a 19- to 30-nt guide strand (antisense strand) comprising a sequence shown in SEQ ID NO: 5 at the 5' end and a 19- to 30-nt passenger strand (sense strand) comprising a sequence shown in SEQ ID NO: 10 at the 3' end or the 5' end.

TABLE 1

| SEQ. NO. | 5' → 3' |
|---|---|
| NO. 1 | AGAGGUUGUUGGAAC |
| NO. 2 | CCUUGACACAGUCCU |
| No. 3 | CGUGAAUGCAUGUGC |
| NO. 4 | GGAGAAGAGAUUCAU |
| NO. 5 | GUAUCCGAUGUCAGG |
| NO. 6 | GUUCCAACAACCUCU |
| NO. 7 | AGGACUGUGUCAAGG |
| NO. 8 | GCACAUGCAUUCACG |
| NO. 9 | AUGAAUCUCUUCUCC |
| NO. 10 | CCUGACAUCGGAUAC |

The siRNA that suppresses NEK6 gene expression may also be a single-strand nucleic acid molecule forming a hairpin RNA structure, wherein the 3' end of the passenger strand (sense strand) and the 5' end of the guide strand (antisense strand) are linked to each other via a linker sequence of a nucleotide residue and/or a linker of a non-nucleotide structure, or the 3' end of the guide strand (antisense strand) and the 5' end of the passenger strand (sense strand) are linked to each other via a linker sequence of a nucleotide residue and/or a linker of a non-nucleotide structure.

The length of the linker sequence of a nucleotide residue described above is not particularly limited, but it is preferable, for example, that the passenger strand and the guide strand have a length that can form a duplex strand. The number of nucleotides in the linker sequence has the lower limit of, for example, 1-nt, preferably 2-nt, and more preferably 3-nt; and the upper limit of, for example, 100-nt, preferably 80-nt, and more preferably 50-nt. Specific examples of the number of nucleotides in the linker sequence are 1 to 100, 2 to 80, and 3 to 50.

Examples of the linkers comprising a non-nucleotide structure described above include chemical linkers such as a hexaethyleneglycol linker, a poly(oxyphosphinico-oxy-1,3-propanediol) linker, an allyl linker, or a polyethyleneglycol linker; and an amino linker having a carbamate structure. The length of the linker comprising a non-nucleotide structure is not limited, but it is preferable, for example, that the passenger strand and the guide strand have a length that can form a duplex strand.

(3) ssPN Molecules

An ssPN molecule to be one of the nucleic acid that suppresses NEK6 gene expression will be described. An ssPN molecule means a single-strand RNA nucleic acid molecule having excellent biological stability, which is disclosed in WO2012/017919, and is particularly as follows.

The ssPN molecule as an active ingredient of the present invention is a single-strand nucleic acid molecule containing a sequence suppressing NEK6 gene expression, and is characterized by containing a region (X), a linker region (Lx), and a region (Xc); wherein the linker region (Lx) is linked between the region (X) and the region (Xc); wherein at least one of the region (X) and the region (Xc) contains the sequence suppressing the expression; wherein the linker region (Lx) has a non-nucleotide structure containing at least one of a pyrrolidine skeleton and a piperidine skeleton. The ssPN molecule has the 5' end and the 3' end unlinked, and can also be referred to as a linear single-strand nucleic acid molecule.

In the ssPN molecule, a sequence suppressing NEK6 gene expression is, for example, a sequence that exhibits a suppressing activity on NEK6 gene expression when the ssPN molecule of the present invention is introduced into a cell in vivo or in vitro. An siRNA sequence to bind to NEK6 mRNA can be obtained in accordance with an existing siRNA-designing system on the basis of cDNA sequence information of NEK6 gene, and the ssPN molecule can also employ the sequence suppressing expression for siRNA as a sequence suppressing expression for the ssPN molecule.

It is preferable that the sequence suppressing expression have, for example, a 80% or more of complementarity to a target region of NEK6 gene, which is more preferably 90% or more, yet preferably 95% or more, yet more preferably 98% or more, and particularly preferably 100%.

In particular, with regard to a part corresponding to a seed region of siRNA, it is preferable to select a sequence specific to NEK6 gene as similar to the case of siRNA.

Suppression of NEK6 gene expression caused by the ssPN molecule is estimated to be due to, for example, occurrence of RNA interference, but is not limited by this mechanism. The ssPN molecule of the present invention is not one which is introduced into a cell or the like as a dsRNA consisting of two single-strand RNAs, such as so-called siRNA, and furthermore, excision of the sequence suppressing the expression is not necessarily essential within a cell.

In the ssPN molecule, the linker region (Lx) may have, for example, the non-nucleotide structure containing a pyrrolidine skeleton, or may have the non-nucleotide structure containing a piperidine skeleton, or may have both of the non-nucleotide structure containing a pyrrolidine skeleton and the non-nucleotide structure containing a piperidine skeleton.

In the ssPN molecule, the pyrrolidine skeleton may be, for example, a skeleton of pyrrolidine derivatives in which one or more carbons composing a five-membered ring of pyrrolidine are substituted, and if substituted, it is preferable that it be, for example, a carbon atom other than a carbon at position 2 (C-2) in the five-membered ring. The carbon may be substituted with, for example, nitrogen, oxygen, or sulfur.

The pyrrolidine skeleton may contain, for example, a carbon-carbon double bond or a carbon-nitrogen double bond, for example, within a five-membered ring of pyrrolidine. In the pyrrolidine skeleton, carbons and a nitrogen composing a five-membered ring of pyrrolidine, for example, may have a bond to a hydrogen, or may have a bond to a substituent as mentioned later. The linker region (Lx) may bind to the region (X) and the region (Xc), for example, via any groups on the pyrrolidine skeleton, which are preferably any one of carbon atoms and a nitrogen in the five-membered ring and are preferably a carbon at position 2 (C-2) and a nitrogen in the five-membered ring. Examples of the pyrrolidine skeletons include a proline skeleton and a prolinol skeleton. The proline skeleton and prolinol skeleton and the like are, for example, an in-vivo substance and a reductant thereof, and thus also have excellent safety.

In the ssPN molecule, the piperidine skeleton may be, for example, a skeleton of piperidine derivatives in which one or more carbons composing of a six-membered ring of piperidine are substituted, and if substituted, it is preferable that it be, for example, a carbon atom other than a carbon at position 2 (C-2) in the six-membered ring. The carbon may be substituted with, for example, nitrogen, oxygen, or sulfur. The piperidine skeleton may contain, for example, a carbon-carbon double bond or a carbon-nitrogen double bond, for example, within a six-membered ring of pyrrolidine. In the piperidine skeleton, carbons and a nitrogen composing a six-membered ring of piperidine, for example, may have a bond to a hydrogen, or may have a bond to a substituent as mentioned later. The linker region (Lx) may bind to the region (X) and the region (Xc), for example, via any groups on the piperidine skeleton, which are preferably any one of carbon atoms and a nitrogen in the six-membered ring and are preferably a carbon at position 2 (C-2) and a nitrogen in the six-membered ring.

The linker region, for example, may contain only a non-nucleotide residue consisting of the non-nucleotide structure described above, or may contain a non-nucleotide residue consisting of the non-nucleotide structure and a nucleotide residue.

In the ssPN molecule, the linker region is represented by, for example, the following formula (I).

[Chemical Formula 2]

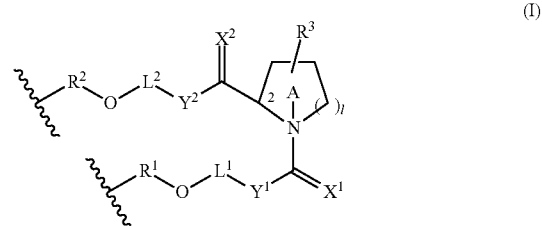

(I)

In the formula (I), for example, $X^1$ and $X^2$ are each independently $H_2$, O, S, or NH;

$Y^1$ and $Y^2$ are each independently a single bond, $CH_2$, NH, O, or S;

$R^3$ is a hydrogen atom or a substituent bound to C-3, C-4, C-5, or C-6 on ring A;

$L^1$ is an alkylene chain having n number of carbon atoms, wherein each of hydrogen atoms on the alkylene carbon atom may or may not be substituted with OH, $OR^a$, $NH_2$, $NHR^a$, $NR^aR^b$, SH, or $SR^a$, or $L^1$ is a polyether chain in which one or more carbon atoms in the alkylene chain are replaced with one or more oxygen atoms, with the proviso that if $Y^1$ is NH, O, or S, then an atom in $L^1$ bound to $Y^1$ is carbon, an atom in $L^1$ bound to $OR^1$ is carbon, and oxygen atoms are not adjacent to each other;

$L^2$ is an alkylene chain comprising m carbon atoms, wherein each of hydrogen atoms on the alkylene carbon atom may or may not be substituted with OH, $OR^c$, $NH_2$, $NHR^c$, $NR^cR^d$, SH, or $SR^c$, or $L^2$ is a polyether chain in which one or more carbon atoms in the alkylene chain are replaced with one or more oxygen atoms, with the proviso that if $Y^2$ is NH, O, or S, then an atom in $L^2$ bound to $Y^2$ is carbon, an atom in L bound to $OR^2$ is carbon, and oxygen atoms are not adjacent to each other;

$R^a$, $R^b$, $R^c$, and $R^d$ are each independently a substituent or a protecting group;

l is 1 or 2;

m is an integer ranging from of 0 to 30;

n is an integer ranging from of 0 to 30;

one carbon atom on the ring A other than C-2 may be replaced with nitrogen, oxygen, or sulfur, the ring A may comprise a carbon-carbon double bond or a carbon-nitrogen double bond therein, the region (Xc) and the region (X) are each bound to the linker region (Lx) via —$OR^1$— or $OR^2$—;

wherein $R^1$ and $R^2$ may or may not be present, and if present, $R^1$ and $R^2$ are each independently a nucleotide residue or the structure (I).

In the formula (I), $X^1$ and $X^2$ are, for example, each independently, $H_2$, O, S, or NH. In the formula (I), "$X^1$ is $H_2$" means that $X^1$ forms $CH_2$ (methylene group) with a carbon atom bound to $X^1$.

The same also applies to $X^2$.

In the formula (I), $Y^1$ and $Y^2$ are each independently a single bond, $CH_2$, NH, O, or S.

In the formula (I), in ring A, l is 1 or 2. In the case of l=1, ring A is a five-membered ring, for example, the pyrrolidine skeleton described above. Examples of the pyrrolidine skeleton include a proline skeleton and a prolinol skeleton, including divalent structures thereof. In the case of l=2, ring A is a six-membered ring, for example, the piperidine skeleton described above. In ring A, one carbon atom other than C-2 on ring A may be substituted with nitrogen, oxygen, or sulfur. Ring A may also contain a carbon-carbon double bond or a carbon-nitrogen double bond within ring A. Ring A may, for example, be either L type or D type.

In the formula (I), $R^3$ is a hydrogen atom or a substituent bound to C-3, C-4, C-5, or C-6 on ring A. If $R^3$ is the substituent, the substituent $R^3$ may be single or plural, or absent, and when $R^3$ is plural, they may be the same or different. The substituent $R^3$ is, for example, halogen, OH, $OR^4$, $NH_2$, $NHR^4$, $NR^4R^5$, SH, $SR^4$, an oxo group (=O), alkyl, alkenyl, alkynyl, haloalkyl, aryl, heteroaryl, arylalkyl, cycloalkyl, cycloalkenyl, cycloalkylalkyl, cyclylalkyl, hydroxyalkyl, alkoxyalkyl, aminoalkyl, heterocyclylalkenyl, heterocyclylalkyl, heteroarylalkyl, silyl, silyloxyalkyl, or the like.

$R^4$ and $R^5$ are, for example, each independently a substituent or a protecting group, and may be the same or different. Examples of the substituents as $R^4$ and $R^5$ include halogen, alkyl, alkenyl, alkynyl, haloalkyl, aryl, heteroaryl, arylalkyl, cycloalkyl, cycloalkenyl, cycloalkylalkyl, cyclylalkyl, hydroxyalkyl, alkoxyalkyl, aminoalkyl, heterocyclylalkenyl, heterocyclylalkyl, heteroarylalkyl, silyl, and silyloxyalkyl.

The protecting groups as $R^4$ and $R^5$ are, for example, functional groups that convert a highly reactive functional group to an inactive one, and include known protecting groups. The protecting group can employ, for example, descriptions in a reference (J. F. W. McOmie, "Protecting Groups in Organic Chemistry", Prenum Press, London and New York, 1973). The protecting group is not particularly limited, and examples include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM) and a tolylsulfonylethoxymethyl group (TEM), a dimethoxytrityl group (DMTr). If $R^3$ is $OR^4$, the protecting groups is not particularly limited, and examples include a TBDMS group, an ACE group, a TOM group, a CEE group, a CEM group, and a TEM group.

In the formula (I), $L^1$ is an alkylene chain having n number of carbon atoms. Each of hydrogen atoms on the alkylene carbon atom may or may not be substituted with, for example, OH, $OR^a$, $NH_2$, $NHR^a$, $NR^aR^b$, SH, or $SR^a$. Alternatively, $L^1$ may be a polyether chain in which one or more (e.g., 1-3) carbon atoms in the alkylene chain are replaced with one or more oxygen atoms. The polyether chain is, for example, polyethyleneglycol. Here, if $Y^1$ is NH, O, or S, then an atom in L bound to $Y^1$ is carbon, an atom in L bound to $OR^1$ is carbon, and oxygen atoms are not adjacent to each other. In other word, for example, if $Y^1$ is O, then such oxygen atom and an oxygen atom of $L^1$ are not adjacent, and an oxygen atom of $OR^1$ and the oxygen atom of $L^1$ are not adjacent.

In the formula (I), $L^2$ is an alkylene chain having m number of carbon atoms. Each of hydrogen atoms on the alkylene carbon atom may or may not be substituted with, for example, OH, $OR^c$, $NH_2$, $NHR^c$, $NR^cR^d$, SH, or SR. Alternatively, $L^2$ may be a polyether chain in which one or more (e.g., 1-3) carbon atoms in the alkylene chain are replaced with one or more oxygen atoms. Here, if $Y^2$ is NH, O, or S, then an atom in $L^2$ bound to $Y^2$ is carbon, an atom in $L^2$ bound to $OR^2$ is carbon, and oxygen atoms are not adjacent to each other. In other word, for example, if $Y^2$ is O, then such oxygen atom and an oxygen atom of $L^2$ are not adjacent, and an oxygen atom of $OR^2$ and the oxygen atom of $L^2$ are not adjacent.

n of $L^1$ and m of $L^2$ are not particularly limited, and in each of them, the lower limit is, for example, 0, and the upper limit is also not particularly limited. n and m can be appropriately set, for example, in accordance with a desired length of the linker region (Lx). It is preferable that n and m be, for example, each 0-30 in view of manufacturing cost and yield, and they are more preferably 0-20, and yet preferably 0-15. n and m may be the same (n=m) or different. n+m is, for example, 0-30, preferably 0-20, and more preferably 0-15. Here, n of $L^1$ and m of $L^2$ are the numbers of carbon atoms in each alkylene chain, but in the case of a polyether chain in which one or more carbon atoms in the alkylene chain of $L^1$ or $L^2$ are substituted with an oxygen atom, n and m mean the sum of the number of carbon atoms and the number of substituted oxygen atoms.

$R^a$, $R^b$, $R^c$, and $R^d$ are, for example, each independently a substituent or a protecting group. The substituent and protecting group of $R^a$, $R^b$, $R^c$, and $R^d$ are, for example, similar to the substituent and protecting group of $R^4$ and $R^5$.

In the formula (I), hydrogen atoms may be, for example, each independently substituted with halogen such as Cl, Br, F, and I.

The region (Xc) and the region (X) are each bound, for example, to the linker region (Lx) via —$OR^1$— or —$OR^2$—. Here, $R^1$ and $R^2$ may or may not be present. If $R^1$ and $R^2$ are present, $R^1$ and $R^2$ have each independently a nucleotide residue or the structure of the formula (I). If $R^1$ and/or $R^2$ are the nucleotide residues, the linker region (Lx), for example, is comprising the non-nucleotide residue consisting of the structure of the formula (I) except for the nucleotide residues $R^1$ and/or $R^2$, and the nucleotide residue. If $R^1$ and/or $R^2$ represent the structures of the formula (I), the linker region (Lx) will have a structure, for example, in which the two or more non-nucleotide residues consisting of the structures of formula (I) are linked to each other. For example, one, two, three, or four of the structures of formula (I) may be included. Thus, when including a plurality of the structures, the structures of the (I) may be, for example, directly linked or bound via the nucleotide residue. Meanwhile, if $R^1$ and $R^2$ are not present, the linker region (Lx) is comprising, for example, only the non-nucleotide residue consisting of the structure of the formula (I).

Combinations of bonds of the region (Xc) and the region (X) with —$OR^1$— and —$OR^2$— are not particularly limited, and examples include any of the following requirements.

Requirement (1)

The region (Xc) via —$OR^2$— and the region (X) via —$OR^1$— bind to the structure of the formula (I).

Requirement (2)

The region (Xc) via —$OR^1$— and the region (X) via —$OR^2$— bind to the structure of the formula (I).

Examples of the structures of the formula (I) include the following formula (I-1) to formula (I-9), and in the following formulas, n and m are the same as those in the formula (I). In the following formulas, q is an integer of 0-10.

[Chemical Formula 3]

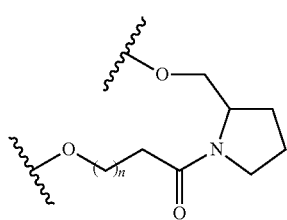

(I-1)

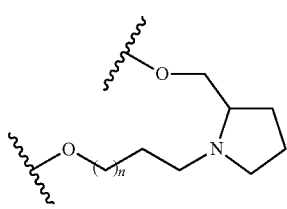

(I-2)

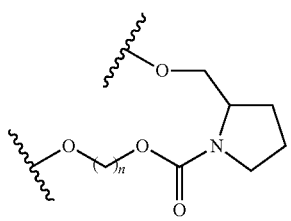

(I-3)

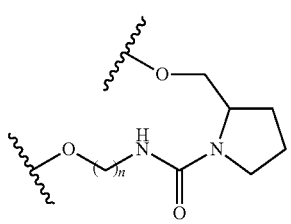

(I-4)

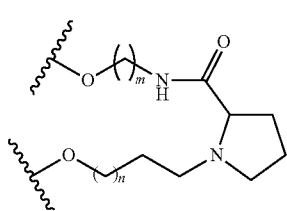

(I-5)

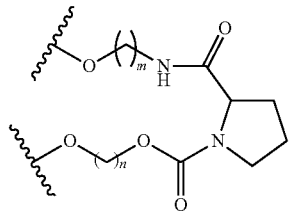

(I-6)

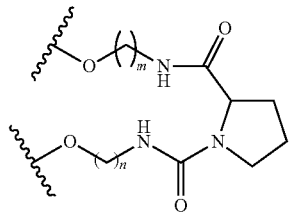

(I-7)

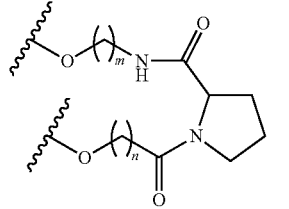

(I-8)

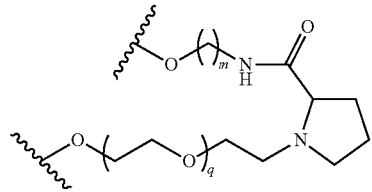

(I-9)

In the formulas (I-1)-(I-9), n, m, and q are not particularly limited, and are as mentioned above. Specific examples include, n=8 in the formula (I-1), n=3 in the (I-2), n=4 or 8 in the formula (I-3), n=7 or 8 in the (I-4), n=3 and m=4 in the formula (I-5), n=8 and m=4 in the (I-6), n=8 and m=4 in the formula (I-7), n=5 and m=4 in the (I-8), q=1 and m=4 in the formula (I-9). An example of the formula (I-4) (n=8) is shown in the following formula (I-4a), and an example of the formula (I-8) (n=5, m=4) is shown in the following (I-8a).

[Chemical Formula 4]

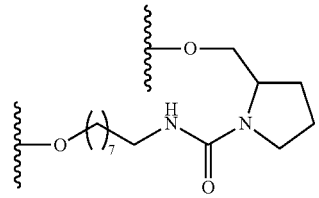

(I-4a)

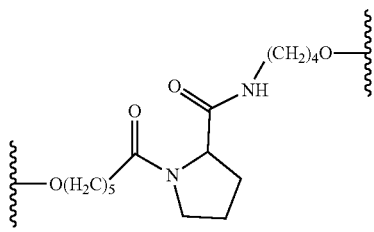

(I-8a)

In the ssPN molecule, the region (Xc) is complementary to the region (X). Hence, in the ssPN molecule, the region (Xc) folds toward the region (X), and the region (Xc) and the region (X) can form a duplex strand through self-annealing.

In the ssPN molecule, for example, only the region (Xc) may fold to form a duplex strand together with the region (X), and furthermore, a new duplex strand may form in another region. Hereinafter, the former ssPN molecule, i.e., a molecule having duplex strand formation at one position, is referred to as "first ssPN molecule", and the latter ssPN molecule, i.e., a molecule having duplex strand formation at two positions is referred to as "second ssPN molecule". The first ssPN molecule and the second ssPN molecule will be illustrated below.

(i) First ssPN Molecules

The first ssPN molecule is a molecule consisting of, for example, the region (X), the region (Xc), and the linker region (Lx).

The first ssPN molecule, for example, may have the region (Xc), the linker region (Lx), and the region (X) in this order from the 5' side to the 3' side, or may have the region (Xc), the linker region (Lx) and the region (X) in this order from the 3' side to the 5' side.

In the first ssPN molecule, the region (Xc) is complementary to the region (X). Here, the region (Xc) is simply required to have a sequence complementary to the entire region of the region (X) or a partial region thereof, and preferably contains a sequence complementary to the entire region of the region (X) or partial region thereof, or consists of only the complementary sequence. The region (Xc) may be, for example, complementary to the complementary entire region or the complementary partial region of the region (X), or one or several nucleotides may be uncomplementary, but it is preferable to be complementary. The one nucleotide or several nucleotides means, for example, 1- to 3-nt, and preferably 1-nt or 2-nt.

In the first ssPN molecule, the sequence suppressing expression is contained in at least of one of the region (Xc) and the region (X). The first ssPN molecule, for example, may have one of the sequence suppressing expression or may have two or more of them. In the latter case, the first ssPN molecule, for example, may have two or more sequences suppressing NEK6 gene expression which are same, or may have two or more sequences suppressing NEK6 gene expression which are different. If the first ssPN molecule has two or more of the sequences suppressing expression, a positional location of each sequence suppressing expression is not particularly limited, and may be in any one region of the region (X) and the region (Xc), or may be in a different region.

An example of the first ssPN molecules will be described according to the schematic diagrams in FIG. 2. FIG. 2 (A) is a schematic diagram showing an outline of order of each region for the ssPN molecule as an example, and FIG. 2 (B) is a schematic diagram showing a state in which the ssPN molecule forms a duplex strand within the molecule. As shown in FIG. 2 (B), in the ssPN molecule, a duplex strand is formed between the region (Xc) and the region (X), and the Lx region takes a loop structure in accordance with the length. FIG. 2 solely shows linkage order of the regions and positional relationship of each region that forms a duplex strand, and for example, the length of each region, the shape of the linker region (Lx), and the like are not limited to this.

In the first ssPN molecule, the numbers of nucleotides in the region (Xc) and the region (X) are not particularly limited. The length of each region will be illustrated below, but the present invention is not limited to this.

The region (Xc) may be, for example, complementary to the entire region of the region (X). This case means that the region (Xc), for example, consists of a nucleotide sequence complementary to the entire region from the 5' end to the 3' end of the region (X), and in other words, means that the region (Xc) and the region (X) have the same nucleotide length, as well as that all nucleotides in the region (Xc) are complementary to all nucleotides in the region (X).

The region (Xc) may also be, for example, complementary to a partial region of the region (X). This case means that the region (Xc), for example, consists of a nucleotide sequence complementary to the partial region of the region (X), and in other words, means that the region (Xc) consists of a nucleotide sequence having a nucleotide length with one or more nucleotides shorter than the region (X), and that all nucleotides in the region (Xc) are complementary to all nucleotides in the partial region of the region (X). It is preferable that the partial region of the region (X) be, for example, a region consisting of a nucleotide sequence running from the end nucleotide (the first nucleotide) on the region (Xc) side in the region (X).

In the first ssPN molecule, relationships of the number of nucleotides (X) in the region (X) and the number of nucleotides (Xc) in the region (Xc) satisfies, for example, the following requirement (3) or (5), and in the case of the former, it particularly, for example, satisfies the following requirement (11).

$$X > Xc \quad (3)$$

$$X - Xc = 1 \text{ to } 10, \text{ preferably } 1, 2, \text{ or } 3, \text{ more preferably } 1 \text{ or } 2 \quad (11)$$

$$X = Xc \quad (5)$$

If the region (X) and/or the region (Xc) contain the sequence suppressing expression, then the region, for example, may be a region composed only of the sequence suppressing expression, or may be a region containing the sequence suppressing expression.

The number of nucleotides in the sequence suppressing expression is, for example, 15- to 30-nt, preferably 19- to 25-nt, more preferably 19- to 23-nt, yet preferably 21-, 22-, 23-nt, and particularly preferably 23-nt. A region containing the sequence suppressing expression may have, for example, an additional sequence at the 5' side and/or the 3' side of the sequence suppressing expression. The number of nucleotides in the additional sequence is, for example, 1- to 31-nt, preferably 1- to 21-nt, and more preferably 1- to 11-nt.

The number of nucleotides in the region (X) is not particularly limited. If the region (X) contains the sequence suppressing expression, the lower limit is, for example, 19-nt. The upper limit is, for example, 50-nt, preferably 40-nt, more preferably 30-nt, and yet preferably 25-nt. Specific examples of the number of nucleotides in the region (X) are, for example, 19- to 50-nt, preferably, 19- to 30-nt, more preferably 19- to 25-nt, yet preferably 21-, 22-, 23-nt, and particularly preferably 23-nt.

The number of nucleotides in the region (Xc) is not particularly limited. The lower limit is, for example, 19-nt, preferably 20-nt, and more preferably 21-nt. The upper limit is, for example, 50-nt, preferably 40-nt, more preferably 30-nt, and yet preferably 25-nt. Specific examples of the number of nucleotides in the region (Xc) are, for example, 19- to 50-nt, preferably 19- to 30-nt, more preferably 19- to 25-nt, yet preferably 21-, 22- and 23-nt, and particularly preferably 21-nt.

In the first ssPN molecule, the length of the linker region (Lx) is not particularly limited. It is preferable that the linker region (Lx), for example, is long enough for the region (X) and the region (Xc) to form a duplex strand. If the linker region (Lx) contains the nucleotide residue other than the non-nucleotide residue, the number of nucleotides in the linker region (Lx) has the lower limit of, for example, 1-nt, preferably 2-nt, and more preferably 3-nt, and the upper limit of, for example, 100-nt, preferably 80-nt, and more preferably 50-nt. Specific examples of the number of nucleotides in the linker region (Lx) are 1- to 100-nt, 2- to 80-nt, and 3- to 50-nt. It is preferable the linker region (Lx) have a structure not causing self-annealing inside its own region.

The full length of the first ssPN molecule is not particularly limited. In the first ssPN molecule, the sum of the number of nucleotides (the number of nucleotides in the full length) has the lower limit of, for example, 38-nt, preferably 42-nt, more preferably 44-nt, and yet preferably 48-nt; and the upper limit of, for example, 300-nt, preferably 200-nt, more preferably 150-nt, yet preferably 100-nt, and particularly preferably 80-nt. Specific examples of the sum of the number of nucleotides in the full length of the first ssPN molecule are 38- to 300-nt, 42- to 200-nt, 44- to 150-nt, 48- to 100-nt, and 48- to 80-nt. In the first ssPN molecule, the sum of the number of nucleotides except for that of the linker region (Lx) has the lower limit of, for example, 38-nt, preferably 42-nt, and yet preferably 44-nt; and the upper limit of, for example, 300-nt, preferably 200-nt, more preferably 150-nt, yet preferably 100-nt, and particularly preferably 80. Specific examples of the sum of the number of nucleotides except for that of the linker region (Lx) are 38- to 300-nt, 42- to 200-nt, 42- to 150-nt, 44- to 100-nt, and 44- to 80-nt.

Specific examples of the first ssPN molecules that suppress NEK6 gene expression include the following single-strand nucleic acid molecules.

KB-001
(SEQ ID NO: 31)
5'-GAGGGAGUUCCAACAACCUCUCC-Lx-
GGAGAGGUUGUUGGAACUCCCUCCA-3'

KB-002
(SEQ ID NO: 32)
5'-CGAGGCAGGACUGUGUCAAGGCC-Lx-
GGCCUUGACACAGUCCUGCCUCGCC-3'

KB-003
(SEQ ID NO: 33)
5'-CGUGGAGCACAUGCAUUCACGCC-Lx-
GGCGUGAAUGCAUGUGCUCCACGGC-3'

KB-004
(SEQ ID NO: 34)
5'-GAUAAGAUGAAUCUCUUCUCCCC-Lx-
GGGGAGAAGAGAUUCAUCUUAUCUC-3'

KB-005
(SEQ ID NO: 35)
5'-CAGAGACCUGACAUCGGAUACCC-Lx-
GGGUAUCCGAUGUCAGGUCUCUGGU-3'

KB-006
(SEQ ID NO: 46)
5'-GGAGAUAAGAUGAAUCUCUUCCC-Lx-
GGGAAGAGAUUCAUCUUAUCUCCAU-3'

KB-007
(SEQ ID NO: 47)
5'-CUAUGGAGAUAAGAUGAAUCUCC-Lx-
GGAGAUUCAUCUUAUCUCCAUAGAA-3'

KB-008
(SEQ ID NO: 48)
5'-GCGGACUUCCAGAUCGAAAAGCC-Lx-
GGCUUUUCGAUCUGGAAGUCCGCCA-3'

KB-009
(SEQ ID NO: 49)
5'-CGGACUUCCAGAUCGAAAAGACC-Lx-
GGUCUUUUCGAUCUGGAAGUCCGCC-3'

KB-010
(SEQ ID NO: 50)
5'-GACUUCCAGAUCGAAAAGAAGCC-Lx-
GGCUUCUUUUCGAUCUGGAAGUCCG-3'

KB-011
(SEQ ID NO: 61)
5'-GACUCGUUUAUCGAAGACAACCC-Lx-
GGGUUGUCUUCGAUAAACGAGUCCA-3'

Wherein Lx is a linker region Lx, and represents L-proline-diamide-amidite in the following structural formula.

[Chemical Formula 5]

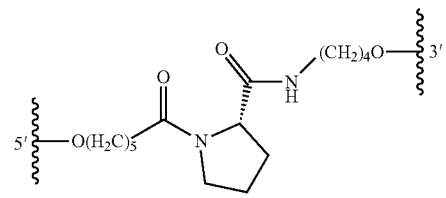

Furthermore, preferable first ssPN molecules include a single-strand nucleic acid molecule which contains a sequence that suppresses NEK6 gene expression selected from SEQ ID NOs: 1 to 5 and consists of only a region (X), a linker region (Lx), and a region (Xc), which are disposed in order of the region (Xc), the linker region (Lx), and the region (X) from the 5' side to the 3' side,
wherein the linker region (Lx) has a non-nucleotide structure containing at least one of a pyrrolidine skeleton and a piperidine skeleton, and
wherein the region (X) comprises the sequence suppressing expression.

Yet preferably, the region (Xc) is the above-described single-strand nucleic acid fully complementary to the entire region or a partial region of the region (X). Particularly preferably, the region (X) is the above-described single-strand nucleic acid containing a sequence selected from the group consisting of SEQ ID NOs: 11 to 25.

TABLE 2

| SEQ. NO. | 5' → 3' |
|---|---|
| NO. 11 | AGAGGUUGUUGGAACUCCC |
| NO. 12 | CCUUGACACAGUCCUGCCU |
| No. 13 | CGUGAAUGCAUGUGCUCCA |
| NO. 14 | GGAGAAGAGAUUCAUCUUA |
| NO. 15 | GUAUCCGAUGUCAGGUCUC |
| NO. 16 | AGAGGUUGUUGGAACUCCCUC |
| NO. 17 | CCUUGACACAGUCCUGCCUCG |
| NO. 18 | CGUGAAUGCAUGUGCUCCACG |
| NO. 19 | GGAGAAGAGAUUCAUCUUAUC |
| NO. 20 | GUAUCCGAUGUCAGGUCUCUG |
| NO. 21 | AGAGGUUGUUGGAACUCCCUCCA |
| NO. 22 | CCUUGACACAGUCCUGCCUCGCC |
| NO. 23 | CGUGAAUGCAUGUGCUCCACGGC |
| NO. 24 | GGAGAAGAGAUUCAUCUUAUCUC |
| NO. 25 | GUAUCCGAUGUCAGGUCUCUGGU |

(ii) Second ssPN Molecules

The second ssPN molecule is, for example, a molecule further having a region (Y) and a region (Yc) complementary to the region (Y) in addition to the region (X), the linker region (Lx), and the region (Xc). In the second ssPN molecule, the region (X) and the region (Y) are linked to each other to form an inner region (Z). Additionally, unless otherwise indicated, the second ssPN molecule can employ the descriptions about the first ssPN molecule.

The second ssPN molecule, for example, may have the region (Xc), the linker region (Lx), the region (X), the region (Y), and the region (Yc) in this order from the 5' side to the 3' side. In this case, the region (Xc) is also referred to as a 5' side region (Xc); the region (X) in the inner region (Z) is also referred to as an inner 5' side region (X); the region (Y) in the inner region (Z) is also referred to as an inner 3' region (Y); and the region (Yc) is also referred to as a 3' side region (Yc). The second ssPN molecule may also have, for example, the region (Xc), the linker region (Lx), the region (X), the region (Y), and the region (Yc) in this order from the 3' side to the 5' side. In this case, the region (Xc) is also referred to as a 3' side region (Xc); the region (X) in the inner region (Z) is also referred to as an inner 3' side region (X); the region (Y) of the inner region (Z) is also referred to as an inner 5' region (Y); and the region (Yc) is also referred to as a 5' side region (Yc).

In the inner region (Z), for example, the region (X) and the region (Y) are linked to each other. The region (X) and the region (Y) are, for example, directly linked, and have no intervening sequence therebetween. The inner region (Z) is defined as "consists of the region (X) linked to the region (Y)" in order to show relationship of sequences of the region (Xc) and the region (Yc), and do not limit as, in the inner region (Z), the region (X) and the region (Y) are separate, independent regions in use of the ssPN molecule. In other words, for example, if the inner region (Z) has the sequences suppressing expression, the sequences suppressing expression may be disposed over the region (X) and the region (Y) in the inner region (Z).

In the second ssPN molecule, the region (Xc) is complementary to the region (X). Here, the region (Xc) is simply required to have a sequence complementary to the entire region of the region (X) or a partial region thereof, and preferably contains a sequence complementary to the entire region of the region (X) or a partial region thereof, or consists of the complementary sequence. The region (Xc) may be, for example, complementary to the complementary entire region or the complementary partial region of the region (X), or one or several nucleotides may be uncomplementary, but it is preferable to be complementary. The one nucleotide or several nucleotides means, for example, 1- to 3-nt, and preferably 1-nt or 2-nt.

In the second ssPN molecule, the region (Yc) is complementary to the region (Y). Here, the region (Yc) is simply required to have a sequence complementary to the entire region of the region (Y) or a partial region thereof, and preferably contains a sequence complementary to the entire region of the region (Y) or a partial region thereof, or consists of the complementary sequence. The region (Yc) may be, for example, complementary to the complementary entire region or the complementary partial region of the region (Y), or one or several nucleotides may be uncomplementary, but it is preferable to be complementary. The one nucleotide or several nucleotides means, for example, 1- to 3-nt, and preferably 1-nt or 2-nt.

In the second ssPN molecule, the sequence suppressing expression, for example, is contained in at least one of the inner region (Z) comprising the region (X) and the region (Y), and the region (Xc), and may be further contained in the region (Yc). Preferable is an ssPN molecule in which the sequence suppressing expression is contained in the inner region (Z). If having the sequence suppressing expression, the inner region (Z), for example, may have the sequence suppressing expression in either of the region (X) and the region (Y), or alternatively may have the sequence suppressing expression over the region (X) and the region (Y). The second ssPN molecule, for example, may have one of the sequences suppressing expression or may have two or more of them.

If the second ssPN molecule has two or more of the sequences suppressing expression, a positional location of each sequence suppressing expression is not particularly limited, and may be in either of the inner region (Z) and the region (Xc), or may be in either of the inner region (Z) and the region (Xc) and in yet another different region.

In the second ssPN molecule, the region (Yc) and the region (Y), for example, may be directly linked or indirectly linked. In the case of the former, examples of direct linkages include linkages such as a phosphodiester bond. In the latter case, examples include a form having a linker region (Ly) between the region (Yc) and the region (Y), in which the region (Yc) and the region (Y) are linked to each other via the linker region (Ly).

If the second ssPN molecule has the linker region (Ly), the linker region (Ly) may be, for example, a linker consisting of the nucleotide residue, or may be a linker having the non-nucleotide structure containing at least one of a pyrrolidine skeleton and piperidine skeleton as mentioned above. In the latter case, the linker region (Ly) can be represented by, for example, the formula (I), and can employ all of the description about the formula (I) in the linker region (Lx).

The region (Yc) and the region (Y) are each bound, for example, to the linker region (Ly) via —OR$^1$— or —OR$^2$—. Here, R$^1$ and R$^2$ may or may not be present as similar to those in the linker region (Lx) mentioned above.

Combinations of bonds of the region (Xc) and the region (X), and the region (Yc) and the (Y), with —OR$^1$— and —OR$^2$— are not particularly limited, and examples include any of the following requirements.

Requirement (1)

The region (Xc) via —OR$^2$— and the region (X) via —OR$^1$— bind to the structure of the formula (I), and the region (Yc) via —OR$^1$— and the region (Y) via —OR$^2$— bind to the structure of the formula (I).

Requirement (2)

The region (Xc) via —OR$^2$— and the region (X) via —OR$^1$— bind to the structure of the formula (I), and the region (Yc) via —OR$^2$— and the region (Y) via —OR$^1$— bind to the structure of the formula (I).

Requirement (3)

The region (Xc) via —OR$^1$— and the region (X) via —OR$^2$— bind to the structure of the formula (I), and the region (Yc) via —OR$^1$— and the region (Y) via —OR$^2$— bind to the structure of the formula (I).

Requirement (4)

The region (Xc) via —OR$^1$— and the region (X) via —OR$^2$— bind to the structure of the formula (I), and the region (Yc) via —OR$^2$— and the region (Y) via —OR$^1$— bind to the structure of the formula (I).

Figure 3:
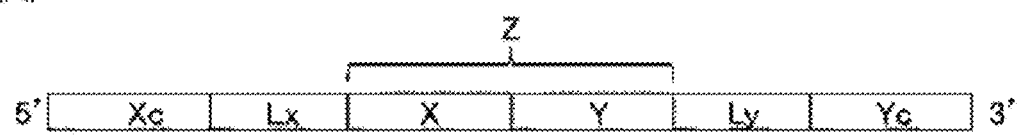
FIGS. 3(A) and 3(B) represent schematic diagrams showing an example of nucleic acid molecules as an active ingredient of a phosphorylation inhibitor of SMAD2/3 protein of the present invention (an ssPN molecule or ssNc molecule).
Figure 3:
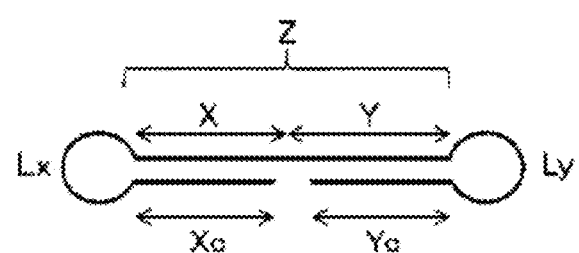

With regard to the second ssPN molecule, an example of the ssPN molecules having the linker region (Ly) will be described according to the schematic diagrams in FIG. 3. FIG. 3 (A) is a schematic diagram showing an outline of order of each region from the 5' side to the 3' side for the ssPN molecule as an example, and FIG. 3 (B) is a schematic diagram showing a state in which the ssPN molecule forms a duplex strand within the molecule. As shown in FIG. 3 (B), in the ssPN molecule, duplex strands are formed between the region (Xc) and the region (X) and between the region (Y) and the region (Yc), and the Lx region and the Ly region take loop structures depending on the length. FIG. 3 solely shows linkage order of each region and positional relationship of each region that forms a duplex strand, and for example, the length of each region, the shape of the linker region, and the like are not limited to this. Moreover, in FIG. 3, the region (Xc) is shown at the 5' side, but not limited to this, and the region (Xc) may be located at the 3' side.

In the second ssPN molecule, the numbers of nucleotides in the region (Xc), the region (X), the region (Y), and the region (Yc) are not particularly limited. The length of each region will be illustrated below, but the present invention is not limited to this.

The region (Xc) may be, for example, complementary to the entire region of the region (X). In this case, it is preferable the region (Xc), for example, have the same nucleotide length as the region (X), and consist of a nucleotide sequence complementary to the entire region of the region (X). The region (Xc) has, more preferably, the same nucleotide length as the region (X), and all nucleotides in the region (Xc) are complementary to all nucleotides in the region (X). Moreover, none is limited to this, for example, one or several nucleotides may be uncomplementary.

The region (Xc) may also be, for example, complementary to a partial region of the region (X). In this case, it is preferable that the region (Xc) have, for example, the same nucleotide length as the partial region of the region (X), in other words, consist of a nucleotide sequence with a nucleotide length one or more nucleotides shorter than the region (X). The region (Xc) has, more preferably, the same nucleotide length as the partial region of the region (X), and all nucleotides in the region (Xc) are complementary to all nucleotides in the partial region of the region (X). It is preferable that the partial region of the region (X) be, for example, a region consisting of a nucleotide sequence running from the end nucleotide (the first nucleotide) on the region (Xc) side in the region (X).

The region (Yc) may be, for example, complementary to the entire region of the region (Y). In this case, it is preferable that the region (Yc) have, for example, the same nucleotide length as the region (Y), and consist of a nucleotide sequence complementary to the entire region of the region (Y). The region (Yc) has, more preferably, the same nucleotide length as the region (Y) and all nucleotides in the region (Yc) are complementary to all nucleotides in the region (Y). Moreover, none is limited to this, for example, one or several nucleotides may be uncomplementary.

The region (Yc) may also be, for example, complementary to a partial region of the region (Y). In this case, the region (Yc) have, for example, the same nucleotide length as the partial region of the region (Y), and in other words, it is preferable to consist of a nucleotide sequence with nucleotide length one or more nucleotides shorter than the region (Y). The region (Yc) has, more preferably, the same nucleotide length as the partial region of the region (Y), and all nucleotides in the region (Yc) are complementary to all nucleotides in the partial region of the region (Y). It is preferable that the partial region of the region (Y) be, for example, a region consisting of a nucleotide sequence running from the end nucleotide (the first nucleotide) on the region (Yc) side in the region (Y).

In the second ssPN molecule, relationship of the number of nucleotides (Z) in the inner region (Z) to the number of nucleotides (X) in the region (X) and the number of nucleotides (Y) in the region (Y), and relationship of the number of nucleotides (Z) in the inner region (Z) to the number of nucleotides (Xc) in the region (Xc) and the number of nucleotides (Yc) in the region (Yc) satisfy, for example, requirements of the following formula (1) and (2).

$$Z=X+Y \tag{1}$$

$$Z \geq Xc+Yc \tag{2}$$

In the second ssPN molecule, relationship of the number of nucleotides (X) in the region (X) to the number of nucleotides (Y) in the region (Y) is not particularly limited, and for example, satisfies any of requirements of the following formulas.

$$X=Y \tag{19}$$

$$X<Y \tag{20}$$

$$X>Y \tag{21}$$

In the second ssPN molecule, relationship of the number of nucleotides (X) in the region (X), the number of nucleotides (Xc) in the region (Xc), the number of nucleotides (Y) in the region (Y), and the number of nucleotides (Yc) in the region (Yc) satisfies, for example, any of requirements of the following (a) to (d).

(a) Satisfy requirements of the following formulas (3) and (4).

$$X > Xc \quad (3)$$

$$Y = Yc \quad (4)$$

(b) Satisfy requirements of the following formulas (5) and (6).

$$X = Xc \quad (5)$$

$$Y > Yc \quad (6)$$

(c) Satisfy requirements of the following formulas (7) and (8).

$$X > Xc \quad (7)$$

$$Y > Yc \quad (8)$$

(d) Satisfy requirements of the following formulas (9) and (10).

$$X = Xc \quad (9)$$

$$Y = Yc \quad (10)$$

In the (a) to (d), it is preferable that difference between the number of nucleotides (X) in the region (X) and the number of nucleotides (Xc) in the region (Xc), and difference between the number of nucleotides (Y) in the region (Y) and the number of nucleotides (Yc) in the region (Yc) satisfy, for example, the following requirements.

(a) Satisfy requirements of the following formulas (11) and (12).

$$X-Xc=1 \text{ to } 10, \text{preferably } 1,2,3, \text{ or } 4, \text{ more preferably } 1,2, \text{ or } 3 \quad (11)$$

$$Y-Yc=0 \quad (12)$$

(b) Satisfy requirements of the following formulas (13) and (14).

$$X-Xc=0 \quad (13)$$

$$Y-Yc=1 \text{ to } 10, \text{preferably } 1,2,3, \text{ or } 4, \text{ more preferably } 1,2, \text{ or } 3 \quad (14)$$

(c) Satisfy requirements of the following formulas (15) and (16).

$$X-Xc=1 \text{ to } 10, \text{preferably}, 1,2, \text{ or } 3, \text{ more preferably } 1 \text{ or } 2 \quad (15)$$

$$Y-Yc=1 \text{ to } 10, \text{preferably}, 1,2, \text{ or } 3, \text{ more preferably } 1 \text{ or } 2 \quad (16)$$

(d) Satisfy requirements of the following formulas (17) and (18).

$$X-Xc=0 \quad (17)$$

$$Y-Yc=0 \quad (18)$$

Figure 4:
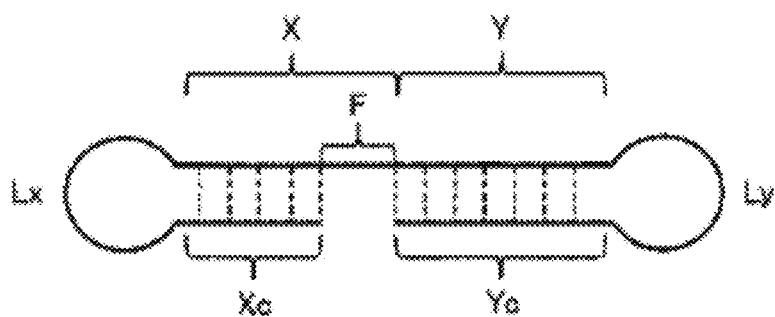
FIGS. 4(A)-4(D) represent schematic diagrams showing an example of nucleic acid molecules as an active ingredient of a phosphorylation inhibitor of SMAD2/3 protein of the present invention (ssPN molecules or ssNc molecules).
Figure 4:
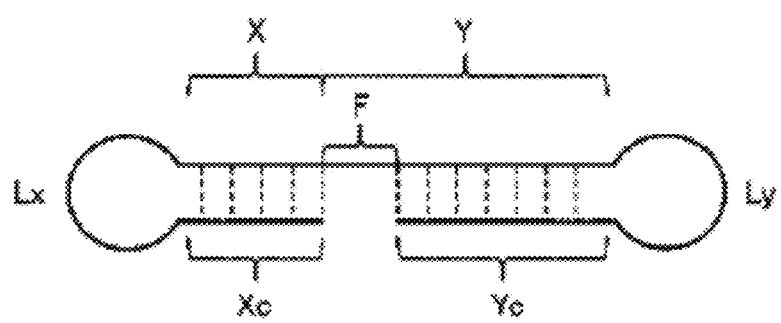
Figure 4:
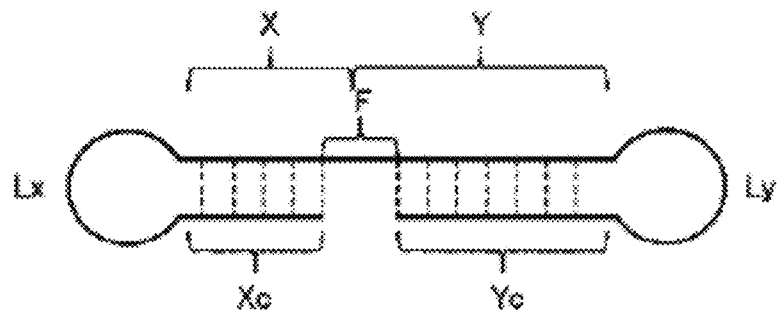
Figure 4:
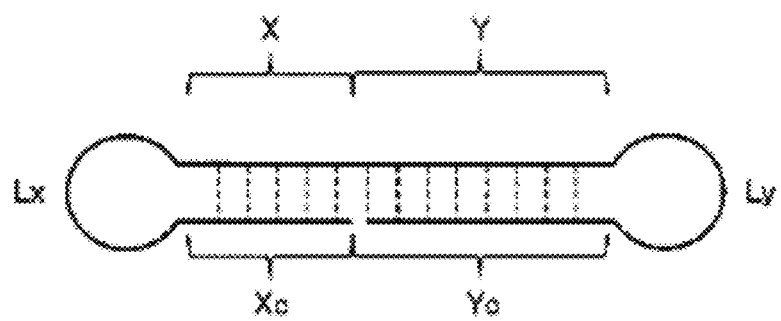

With regard to the second ssPN molecules of the (a) to (d), an example of each structure will be described according to schematic diagrams in FIG. 4. FIG. 4 represents ssPNs containing the linker region (Lx) and the linker region (Ly): (A) is an example of ssPN molecules of the (a); (B) is an example of ssPN molecules of the (b); (C) is an example of ssPN molecules of the (c); and (D) is an example of ssPN molecules of the (d). In FIG. 4, dotted lines represent a state of forming a duplex strand through self-annealing. In ssPN molecules in FIG. 4, the number of nucleotides (X) in the region (X) and the number of nucleotides (Y) in the region (Y) are represented as "X<Y" of the formula (20), but are not limited to this, and they may be "X=Y" of the formula (19) or "X>Y" of the formula (21). Moreover, FIG. 4 represents schematic diagrams sorely showing relationship between the region (X) and the region (Xc), and relationship between the region (Y) and the region (Yc), and for example, the length of each region, shape, presence or absence of the linker region (Ly), or the like are not limited to this.

The ssPN molecules of the (a) to (c) have structures, for example, in which each of the region (Xc) with the region (X), and the region (Yc) with the region (Y) forms a duplex strand thereby having nucleotides not aligned with either of the region (Xc) and the region (Yc) in the inner region (Z); and they may also be considered as nucleotide not forming duplex strands. In the inner region (Z), the unaligned nucleotides (also referred to as nucleotides not forming a duplex strand) are hereinafter referred to as "free nucleotides". In FIG. 4, the region of fee nucleotides is shown by "F". The number of nucleotides in the region (F) is not particularly limited. The number of nucleotides (F) in the region (F) is, for example, the number of nucleotides of "X−Xc" in the case of the ssPN molecule of the (a), the number of nucleotides of "Y−Yc" in the case of the ssPN molecule of the (b), the sum of the number of nucleotides of "X−Xc" and the number of nucleotides of "Y−Yc" in the case of ssPN molecule in the (c).

In contrast, the ssPN molecule of the (d) has a structure, for example, in which the entire region of the inner region (Z) is aligned to the region (Xc) and the region (Yc), and it may also be considered as a structure in which the entire region of the inner region (Z) forms a duplex strand. Here, in the ssPN molecule of the (d), the 5' end of the region (Xc) and the 3' end of the region (Yc) are unlinked.

The sum of the number of nucleotides of the region (Xc), the region (Yc), and the free nucleotides (F) in the inner region (Z) will be the number of nucleotides in the inner region (Z). Thus, the lengths of the region (Xc) and the region (Yc) are appropriately determined, for example, in accordance with the length of the inner region (Z) and the number and position of the free nucleotides.

The number of nucleotides in the inner region (Z) is, for example, 19-nt or more. The lower limit of the number of nucleotides is, for example, 19-nt, preferably 20-nt, and more preferably 21-nt. The upper limit of the number of nucleotides is, for example, 50-nt, preferably 40-nt, and more preferably 30-nt. Specific examples of the number of nucleotides in the inner region (Z) are, for example, 19- to 50-nt, 20- to 40-nt, 21- to 30-nt, and 21- to 25-nt.

If the inner region (Z) contains the sequence suppressing expression, the inner region (Z) may be, for example, a region composed of only the sequence suppressing expression, or a region containing the sequence suppressing expression. The number of nucleotides of the sequence suppressing expression is, for example, 15- to 30-nt, preferably 19- to 25-nt, more preferably 19- to 23-nt, yet preferably, 21-nt, 22-nt, 23-nt, and particularly preferably 23-nt. The inner region (Z), if containing the sequence suppressing expression, may further have an additional sequence at the 5' side and/or the 3' side of the sequence suppressing expression. The number of nucleotides of the additional sequence is, for example, 1- to 31-nt, preferably 1- to 21-nt, more preferably 1- to 11-nt, yet preferably 1- to 7-nt, and yet more preferably 1- to 3-nt.

The number of nucleotides in the region (Xc) is, for example, 1- to 49-nt, preferably 1- to 39-nt, and more preferably 1- to 29-nt. The number of nucleotides in the region (Yc) is, for example, 1- to 49-nt, preferably 1- to 39-nt, and more preferably 1- to 29-nt. It is preferable that the number of nucleotides of either of the region (Xc) or (Yc) be 1- to 4-nt, yet preferably 1-nt, 2-nt, or 3-nt.

The number of nucleotides in the inner region (Z), the region (Xc), and the region (Yc) can be represented, for example, by "Z≥Xc+Yc" in the formula (2). As specific example, the number of nucleotides of "Xc+Yc" is, for example, the same as that of the inner region (Z), or less than the inner region (Z). In the case of the latter, "Z−(Xc+Yc)" is, for example, 1 to 10, preferably 1 to 4, and more preferably 1, 2, or 3. The "Z−(Xc+Yc)" corresponds to, for example, the number of nucleotides (F) of the free region (F) in the inner region (Z).

In the second ssPN molecule, the lengths of the linker region (Lx) and the linker region (Ly) are not particularly limited. The linker region (Lx) is as mentioned above. If structure units of the linker region (Ly) contains a nucleotide, the number of nucleotides in the linker region (Ly) has the lower limit of, for example, 1-nt, preferably 2-nt, and more preferably 3-nt; and the upper limit of, for example, 100-nt, preferably 80-nt, and more preferably 50-nt. Specific examples of the number of nucleotides in each of the linker regions include, but not limited to, 1- to 50-nt, 1- to 30-nt, 1- to 20-nt, 1- to 10-nt, 1- to 7-nt, and 1- to 4-nt. It is preferable that the linker region (Ly) be a structure not causing self-annealing within its own region.

The linker region (Ly) may be, for example, the same as or different from the linker region (Lx).

The full length of the second ssPN molecule is not particularly limited. In the second ssPN molecule, the sum of the number of nucleotides (the number of nucleotides of the full length) has the lower limit of, for example, 38-nt, preferably 42-nt, more preferably 44-nt, yet preferably 48-nt, and particularly preferably 50-nt; and the upper limit of, for example, 300-nt, preferably 200-nt, more preferably 150-nt, yet preferably 100-nt, and particularly preferably 80-nt. Specific examples of the sum of the number of nucleotides of the full length of the second ssPN molecule are 38- to 300-nt, 42- to 200-nt, 44- to 150-nt, 48- to 100-nt, and 50- to 80-nt. In the second ssPN molecule, the sum of the number of nucleotides except for those in the linker region (Lx) and the linker region (Ly) has the lower limit of, for example, 38-nt, preferably 42-nt, more preferably 44-nt, yet preferably 48-nt, and particularly preferably 50-nt; and the upper limit of, for example, 300-nt, preferably 200-nt, more preferably 150-nt, yet preferably 100-nt, yet more preferably 80-nt, and particularly preferably 60-nt. Specific examples of the sum of the number of nucleotide except for that in the linker region (Lx) is 38- to 300-nt, 42- to 200-nt, 44- to 150-nt, 48- to 100-nt, 48- to 80-nt, and 50- to 60-nt.

In the ssPN molecule, it is simply required that the linker region (Lx) has the non-nucleotide structure, and the structure units are not particularly limited. Examples of the structure units include nucleotide residues. Examples of the nucleotide residues include ribonucleotide residues and deoxyribonucleotide residues. Examples of the nucleotide residues include unmodified nucleotide residues with no modification and modified nucleotide residues with modification. The ssPN molecules can, for example, contain the modified nucleotide residue, thereby enabling to improve nuclease resistance and raise stability. The ssPN molecule may also, for example, further contain a non-nucleotide residue other than the nucleotide residue.

It is preferable that each of structure units of the region (Xc), the region (X), the region (Y), and the region (Yc) be the nucleotide residue. Each of the region is, for example, composed of the following residues (1) to (3):

(1) an unmodified nucleotide residue,
(2) a modified nucleotide residue,
(3) an unmodified nucleotide residue and a modified nucleotide residue.

The linker region (Lx), for example, may be composed of only the non-nucleotide residue, or may be composed of the non-nucleotide and the nucleotide residue. The linker region (Lx) is composed of, for example, the following residues (4) to (7):

(4) a non-nucleotide residue,
(5) a non-nucleotide residue and an unmodified nucleotide residue,
(6) a non-nucleotide residue and a modified nucleotide residue,
(7) a non-nucleotide residue, an unmodified nucleotide residue, and a modified nucleotide residue.

Structure units of the linker region (Ly) are not particularly limited, and examples include the nucleotide residues and the non-nucleotide residues. The linker region, for example, may be composed of only the nucleotide residue, or may be composed of only the non-nucleotide residue, or may be composed of the nucleotide residue and the non-nucleotide residue. The linker region is composed of, for example, the following residues (1) to (7):

(1) an unmodified nucleotide residue,
(2) a modified nucleotide residue,
(3) an unmodified nucleotide residue and a modified nucleotide residue,
(4) a non-nucleotide residue,
(5) a non-nucleotide residue and an unmodified nucleotide residue,
(6) a non-nucleotide residue and a modified nucleotide residue,
(7) a non-nucleotide residue, an unmodified nucleotide residue, and a modified nucleotide residue.

Examples of the ssPN molecules include a molecule composed of only the nucleotide residues except for the linker region (Lx), and a molecule containing the non-nucleotide residue other than the nucleotide residue. In the ssPN molecule, the nucleotide residues, for example, may be only the unmodified nucleotide residues, or may be only the modified nucleotide residues, or may be both of the unmodified nucleotide residue and the modified nucleotide residue. If the ssPN molecule contains the unmodified nucleotide residue and the modified nucleotide residue, the number of the modified nucleotide residue is not particularly limited, but is, for example, "one or several", particularly, for example, 1 to 5, preferably 1 to 4, more preferably 1 to 3, and most preferably 1 or 2. If the ssPN molecule contains the non-nucleotide residue, the number of the non-nucleotide residue is not particularly limited, but is, for example, "one or several", and particularly, for example, 1 or 2.

In ssPN molecule, it is preferable that the nucleotide residue be, for example, a ribonucleotide residue. In this case, the ssPN molecule of the present invention is also referred to as, for example, "P-ssRNA molecule". Examples of the P-ssRNA molecules include a molecule composed of only the ribonucleotide residues except for the linker region (Lx), and a molecule containing the non-nucleotide residue other than the ribonucleotide residue. In the P-ssRNA molecule, the ribonucleotide residues, for example, may be only the unmodified ribonucleotide residues, or may be only the modified ribonucleotide residues, or may contain both of the unmodified ribonucleotide residue and the modified ribonucleotide residue.

If the P-ssRNA molecule contains, for example, the modified ribonucleotide residue other than the unmodified ribonucleotide residue, the number of the modified ribonucleotide residue is not particularly limited, but is, for example, "one or several", particularly, for example, 1 to 5, preferably 1 to 4, more preferably 1 to 3, and most preferably 1 or 2. Examples of the modified ribonucleotide residues corresponding to the unmodified ribonucleotide residues include the deoxyribonucleotide residue with substitution of a ribose residue with a deoxyribose residue. If the P-ssRNA molecule contains, for example, the deoxyribonucleotide residue other than the unmodified ribonucleotide residue, the number of the deoxyribonucleotide is not particularly limited, but is, for example, "one or several", particularly, for example, 1 to 5, preferably 1 to 4, more preferably 1 to 3, and most preferably 1 or 2.

Preferable ssPN molecules that suppress NEK6 gene expression include a single-strand nucleic acid molecule that contains a sequence suppressing NEK6 gene expression selected from SEQ ID NOs: 1 to 5, and contains a region (Xc), a linker region (Lx), a region (X), a region (Y), a linker region (Ly), and region (Yc) in this order from the 5' side to the 3' side,
wherein the region (X) and the region (Y) are linked to each other to form an inner region (Z),
wherein the region (Xc) is complementary the region (X),
wherein the region (Yc) is complementary to the region (Y), and
wherein the linker region (Lx) and the linker region (Ly) have a non-nucleotide structure comprising at least one of a pyrrolidine skeleton and a piperidine skeleton, and
wherein the inner region (Z) comprises the sequence suppressing expression.

(4) ssNc Molecule

An ssNc molecule which is one of nucleic acids that suppress NEK6 gene expression will be described.
An ssNc molecule means a single-strand RNA nucleic acid molecule disclosed in WO2012/05368, and is specifically as follows.
The ssNc molecule is a single-strand nucleic acid molecule containing a sequence suppressing expression that suppresses the expression of a target gene, and
contains a 5' side region (Xc), an inner region (Z), and a 3' side region (Yc) in this order from the 5' side to the 3' side,
wherein the inner region (Z) consists of an inner 5' side region (X) linked to an inner 3' side region (Y),
wherein the 5' side region (Xc) is complementary to the inner 5' side region (X),
wherein the 3' side region (Yc) is complementary to the inner 3' side region (Y),
wherein at least one of the inner region (Z), the 5' side region (Xc), and the 3' side region (Yc) contains the sequence suppressing expression.

The ssNc molecule has the 5' end and 3' end unlinked, and can also be referred to as a linear single-strand nucleic acid molecule. The ssNc molecule of the present invention, for example, has the inner region (Z) in which the inner 5' region (X) and the inner 3' region (Y) are directly linked.

In ssNc molecule, the 5' side region (Xc) is complementary to the inner 5' side region (X), and the 3' side region (Yc) is complementary to the inner 3' side region (Y). Hence, in the 5' side, the region (Xc) folds toward the region (X), and the region (Xc) and the region (X) can form a duplex strand through self-annealing, whereas on the 3' side, the region (Yc) folds toward the region (Y), and the region (Yc) and the region (Y) can form a duplex strand through self-annealing.

The ssNc molecule, thus, can form a duplex strand within a molecule, and has a structure clearly different from that in which two separate single-strand RNAs form a double-strand RNA thorough annealing, for example, as siRNAs used for a conventional RNA interference.

The sequence suppressing expression in the ssNc molecule can employ the description for ssPN molecules.

Suppression of the expression of NEK6 gene by the ssNc molecule is estimated to be caused by, for example, taking a structure in which the sequence suppressing expression is disposed in at least one of the inner region (Z), the 5' side region (Xc), and the 3' side region (Yc), thereby leading to RNA interference or a phenomenon similar to RNA interference (RNA interference-like phenomenon). Here, mechanisms of the ssNc molecules are also not limited, as are the cases with mechanisms of the ssPN molecules. The ssNc molecule is not one that is introduced into a cell or the like as a dsRNA consisting of two single-strand RNAs, such as so-called siRNA, and furthermore, excision of the sequence suppressing expression is not necessarily essential within a cell. Thus, ssNc molecules can also be considered to have, for example, RNA interference-like function.

In the ssNc molecule, the sequence suppressing expression is contained in at least one of the inner region (Z), the 5' side region (Xc), and the 3' side region (Yc). The ssNc molecule, for example, may have one of the sequences suppressing expression or may have two or more of them. In the latter case, the ssNc molecule, for example, may have two or more of the same sequences suppressing NEK6 gene expression, or may have two or more different sequences suppressing NEK6 gene expression. If the ssNc molecule has two or more of the sequences suppressing expression, a positional location of each sequence suppressing expression is not particularly limited, and may be in any one region of the inner region (Z), the 5' side region (Xc), and the 3' side region (Yc), or may be in different regions.

In the inner region (Z), the inner 5' side region (X) and the inner 3' side region (Y) are linked to each other. The region (X) and the region (Y) are, for example, directly linked, and have no intervening sequence therebetween. The inner region (Z) is indicated as "consists of the inner 5' side region (X) linked to the inner 3' side region (Y)" in order to show relationship of sequences of the 5' side region (Xc) and the 3' side region (Yc), and do not limit as, in the inner region (Z), the inner 5' side region (X) and the inner 3' side region (Y) are separate, independent regions, for example, in use of the ssNc molecule. In other words, for example, if the inner region (Z) has the sequences suppressing expression, the sequences suppressing expression may be disposed over the region (X) and the region (Y) in the inner region (Z).

In the ssNc molecule, the 5' side region (Xc) is complementary to the inner 5' side region (X). Here, the region (Xc) is simply required to have a sequence complementary to the entire region of the region (X) or a partial region thereof, and it is preferable that it particularly, for example, contain a sequence complementary to the entire region of the region (X) or partial region thereof, or consist of the complementary sequence. The region (Xc) may be, for example, fully complementary to the complementary entire region or the complementary partial region of the region (X), or one or several nucleotides may be uncomplementary, but it is preferable to be complementary. In the ssNc molecule, the 3' side region (Yc) is complementary to the inner 3' side region (Y). Here, the region (Yc) is simply required to have a sequence complementary to the entire region of the region (Y) or a partial region thereof, and it is preferable that it particularly, for example, contain a sequence complementary to the entire region of the region (Y) or partial region thereof, or consist of the complementary sequence. The region (Yc) may be, for example, fully complementary to the complementary entire region or the complementary partial region of the region (Y), or one or several nucleotides may be uncomplementary, but it is preferable to be complementary. The one nucleotide or several nucleotides means, for example, 1- to 3-nt, preferably 1-nt or 2-nt.

In the ssNc molecule, the 5' side region (Xc) and the inner 5' side region (X), for example, may be directly linked or indirectly linked. In the former case, examples of direct linkages include a phosphodiester bond. In the latter case, examples include a form having a linker region (Lx) between the region (Xc) and the region (X) in which the region (Xc) and the region (X) are linked to each other via the linker region (Lx).

In the ssNc molecule, the 3' side region (Yc) and the inner 3' side region (Y), for example, may be directly linked or indirectly linked. In the former case, examples of direct linkages include a phosphodiester bond. In the latter case, examples include a form having a linker region (Ly) between the region (Yc) and the region (Y) in which the region (Yc) and the region (Y) are linked to each other via the linker region (Ly).

The ssNc molecule, for example, may have both of the linker region (Lx) and the linker region (Ly), or may have either of them. The latter cases include a form that has the linker region (Lx) between the 5' side region (Xc) and the inner 5' side region (X) and does not have the linker region (Ly) between the 3' side region (Yc) and the inner 3' side region (Y), in other words, in which the region (Yc) and the region (Y) are directly linked. Meanwhile, examples of the latter cases include a form that has the linker region (Ly) between the 3' side region (Yc) and the inner 3' side region (Y) and does not have the linker region (Lx) between the 5' side region (Xc) and the inner 5' side region (X), in other words, in which the region (Xc) and the region (X) are directly linked.

It is preferable the linker region (Lx) and the linker region (Ly) each have a structure not causing self-annealing inside their own regions.

Figure 5:
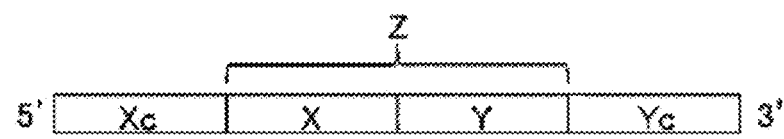
FIGS. 5(A) and 5(B) represent schematic diagrams showing an example of nucleic acid molecules as an active ingredient of a phosphorylation inhibitor of SMAD2/3 protein of the present invention (an ssNc molecule).
Figure 5:
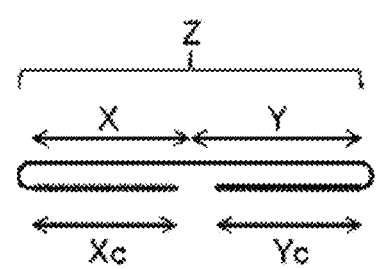

With regard to the ssNc molecule, an example of the ssNc molecules not having the linker region will be described according to the schematic diagrams in FIG. 5. FIG. 5 (A) is a schematic diagram showing an outline of order of each region from the 5' side to the 3' side for the ssNc molecule, and FIG. 5 (B) is a schematic diagram showing a state in which the ssNc molecule forms a duplex strand within the molecule. As shown in FIG. 5 (B), in the ssNc molecule, the 5' side region (Xc) folds and a duplex strand is formed between the 5' side region (Xc) and the inner 5' side region (X); and the 3' side region (Yc) folds and a duplex strand is formed between the 3' side region (Yc) and the inner 3' side region (Y). FIG. 5 solely shows linkage order of each region and positional relationship of each region that forms a duplex strand, and for example, the length of each region and the like are not limited to this.

With regard to the ssNc molecule, an example of the ssNc molecules having the linker region will be described according to the schematic diagrams in FIG. 3. FIG. 3 (A) is a schematic diagram showing an outline of order of each region from the 5' side to the 3' side for the ssNc molecule as an example, and FIG. 3 (B) is a schematic diagram showing a state in which the ssNc molecule forms a duplex strand within the molecule. As shown in FIG. 3 (B), in the ssNc molecule, duplex strands are formed between the 5' side region (Xc) and the inner 5' side region (X) and between the inner 3' side region (Y) and the 3' side region (Yc) and the region (Lx) and (Ly) take loop structures. FIG. 3 solely shows linkage order of each region and positional relationship of each region that forms a duplex strand, and for example, the length of each region and the like are not limited to this.

In the ssNc molecule, the numbers of nucleotides in the 5' side region (Xc), the inner 5' side region (X), the inner 3' side region (Y), and the 3' side region (Yc) are not particularly limited, and for example, are as follows.

The 5' side region (Xc) may be, for example, complementary to the entire region of the inner 5' side region (X). In this case, it is preferable that the region (Xc), for example, have the same nucleotide length as the region (X), and consist of a nucleotide sequence complementary to the entire region from the 5' end to the 3' end of the region (X). The region (Xc) more preferably has the same nucleotide length as the region (X), and it is preferable that all nucleotides in the region (Xc) be complementary to all nucleotides in the region (X). Moreover, none is limited to this, and for example, one or several nucleotides may be uncomplementary.

The 5' side region (Xc) may also be, for example, complementary to a partial region of the inner 5' side region (X). In this case, it is preferable that the region (Xc) have, for example, the same nucleotide length as the partial region of the region (X), in other words, consist of a nucleotide sequence with a nucleotide length one or more nucleotides shorter than the region (X). The region (Xc) more preferably has the same nucleotide length as the partial region of the region (X), and it is preferable that all nucleotides in the region (Xc) be complementary to all nucleotides in the partial region of the region (X). It is preferable that the partial region of the region (X) be, for example, a region (segment) consisting of a nucleotide sequence running from the 5' end nucleotide (the first nucleotide) in the region (X).

The 3' side region (Yc) may be, for example, complementary to the entire region of the inner 3' side region (Y). In this case, it is preferable that the region (Yc), for example, have the same nucleotide length as the region (Y), and consist of a nucleotide sequence complementary to the entire region from the 5' end to the 3' end of the region (Y). The region (Yc) more preferably has the same nucleotide length as the region (Y), and it is preferable that all nucleotides in the region (Yc) be complementary to all nucleotides in the region (Y). Moreover, none is limited to this, and for example, one or several nucleotides may be uncomplementary.

The 3' side region (Yc) may also be, for example, complementary to a partial region of the inner 3' side region (Y). In this case, it is preferable that the region (Yc) have, for example, the same nucleotide length as the partial region of the region (Y), in other words, consist of a nucleotide sequence with a nucleotide length one or more nucleotides shorter than the region (Y). The region (Yc) more preferably has the same nucleotide length as the partial region of the region (Y), and it is preferable that all nucleotides in the region (Yc) be complementary to all nucleotides in the partial region of the region (Y). It is preferable that the partial region of the region (Y) be, for example, a region (segment) consisting of a nucleotide sequence running from the 3' end nucleotide (the first nucleotide) in the region (Y).

In the ssNc molecule, relationship of the number of nucleotides (Z) in the inner region (Z) to the number of nucleotides (X) in the inner 5' side region (X) and the number of nucleotides (Y) in the inner 3' side region (Y), and relationship of the number of nucleotides (Z) in the inner region (Z) to the number of nucleotides (Xc) in the inner 5' side region (Xc) and the number of nucleotides (Yc) in the 5' side region (Yc) satisfy, for example, requirements of the following formulas (1) and (2).

$$Z = X + Y \tag{1}$$

$$Z \geq Xc + Yc \tag{2}$$

In the ssNc molecule, relationship of length between the number of nucleotides (X) in the inner 5' side region (X) and the number of nucleotides (Y) in the inner 3' side region (Y) is not particularly limited, and may satisfy, for example, any requirement of the following formulas.

$$X = Y \tag{19}$$

$$X < Y \tag{20}$$

$$X > Y \tag{21}$$

In the ssNc molecule, relationship of the number of nucleotides (X) in the inner 5' side region (X), the number of nucleotides (Xc) in the 5' side region (Xc), the number of nucleotides (Y) in the inner 3' side region (Y), and the number of nucleotides (Yc) in the 3' side region (Yc) satisfies, for example, any requirement of the following (a) to (d).

(a) Satisfy requirements of the following formulas (3) and (4).

$$X > Xc \tag{3}$$

$$Y = Yc \tag{4}$$

(b) Satisfy requirements of the following formulas (5) and (6).

$$X = Xc \tag{5}$$

$$Y > Yc \tag{6}$$

(c) Satisfy requirements of the following formulas (7) and (8).

$$X > Xc \tag{7}$$

$$Y > Yc \tag{8}$$

(d) Satisfy requirements of the following formulas (9) and (10).

$$X = Xc \tag{9}$$

$$Y = Yc \tag{10}$$

In the (a) to (d), it is preferable that difference between the number of nucleotides (X) in the inner 5' side region (X) and the number of nucleotides (Xc) in the 5' side region (Xc), and difference between the number of nucleotides (Y) in the inner 3' side region (Y) and the number of nucleotides (Yc) in the 3' side region (Yc) satisfy, for example, the following requirements.

(a) Satisfy requirements of the following formulas (11) and (12).

$$X - Xc = 1 \text{ to } 10, \text{preferably } 1, 2, 3, \text{ or } 4, \text{ more preferably } 1, 2, \text{ or } 3 \tag{11}$$

$$Y - Yc = 0 \tag{12}$$

(b) Satisfy requirements of the following formulas (13) and (14).

$$X - Xc = 0 \tag{13}$$

$$Y - Yc = 1 \text{ to } 10, \text{ preferably } 1, 2, 3, \text{ or } 4, \text{ more preferably } 1, 2, \text{ or } 3 \tag{14}$$

(c) Satisfy requirements of the following formulas (15) and (16).

$$X - Xc = 1 \text{ to } 10, \text{ preferably, } 1, 2, \text{ or } 3, \text{ more preferably } 1 \text{ or } 2 \tag{15}$$

$$Y - Yc = 1 \text{ to } 10, \text{ preferably, } 1, 2, \text{ or } 3, \text{ more preferably } 1 \text{ or } 2 \tag{16}$$

(d) Satisfy requirements of the following formulas (17) and (18).

$$X - Xc = 0 \tag{17}$$

$$Y - Yc = 0 \tag{18}$$

With regard to the ssNc molecules of the (a) to (d), an example of each structure will be described according to the schematic diagrams in FIG. 4. FIG. 4 represents ssNcs containing the linker region (Lx) and the linker region (Ly): (A) is an example of ssNc molecules of the (a); (B) is an example of ssNc molecules of the (b); (C) is an example of ssNc molecules of the (c); and (D) is an example of ssNc molecules of the (d). In FIG. 4, dashed lines represent a state of forming a duplex strand through self-annealing. In ssNc molecules in FIG. 4, the number of nucleotides (X) in the inner 5' side region (X) and the number of nucleotides (Y) in the inner 3' side region (Y) are represented as "X<Y" of the formula (20), but are not limited to this, and they may be "X=Y" of the formula (19) or "X>Y" of the formula (21). Moreover, FIG. 4 represents schematic diagrams solely showing relationship between the inner 5' side region (X) and the 5' side region (Xc), and relationship between the inner 3' side region (Y) and the 3' side region (Yc), and for example, the length, shape, and the like are not limited to this, and moreover, the presence and absence of the linker region (Lx) and the linker region (Ly) are also not limited to this.

The ssNc molecules of the (a) to (c) have structures, for example, in which each of the 5' side region (Xc) with the inner 5' side region (X), and the 3' side region (Yc) with the inner 3' side region (Y), forms a duplex strand thereby having nucleotides that cannot be aligned with either of the 5' side region (Xc) and the 3' side region (Yc) in the inner region (Z); and they may also be considered as structures not forming duplex strands. In the inner region (Z), the unaligned nucleotides (also referred to as nucleotides not forming a duplex strand) are hereinafter referred to as "free nucleotides". In FIG. 4, the region of free nucleotides is shown by "F". The number of nucleotides in the region (F) is not particularly limited. The number of nucleotides (F) in the region (F) is, for example, the number of nucleotides of "X−Xc" in the case of the ssNc molecule of the (a), the number of nucleotides of "Y−Yc" in the case of the ssNc molecule of the (b), the sum of the number of nucleotides of "X−Xc" and the number of nucleotides of "Y−Yc" in the case of ssNc molecule of the (c).

In contrast, the ssNc molecule of the (d) has a structure, for example, in which the entire region of the inner region (Z) is aligned with the 5' side region (Xc) and the 3' side region (Yc), and it may also be considered as a structure in which the entire region of the inner region (Z) forms a duplex strand. Here, in the ssNc molecule of the (d), the 5' end of the 5' side region (Xc) and the 3' end of the 3' side region (Yc) are unlinked.

The sum of the number of nucleotides in the 5' side region (Xc), the 3' side region (Yc), and the free nucleotides (F) in the inner region (Z) will be the number of nucleotides in the inner region (Z). Thus, the length of the 5' side region (Xc) and the 3' side region (Yc) is appropriately determined, for example, in accordance with the length of the inner region (Z) and the number and position of the free nucleotides.

The number of nucleotides in the inner region (Z) is, for example, 19-nt or more. The lower limit of the number of nucleotides is, for example, 19-nt, preferably 20-nt, and more preferably 21-nt. The upper limit of the number of nucleotides is, for example, 50-nt, preferably 40-nt, and more preferably 30-nt. Specific examples of the number of nucleotides in the inner region (Z) are, for example, 19- to 50-nt, 20- to 40-nt, 21- to 30-nt, and 21- to 23-nt.

If the inner region (Z) contains the sequence suppressing expression, the inner region (Z) may be, for example, a region composed of only the sequence suppressing expression, or a region containing the sequence suppressing expression. The number of nucleotides of the sequence suppressing expression is, for example, 15- to 30-nt, preferably 19- to 25-nt, more preferably 19- to 23-nt, yet preferably, 21-, 22-, 23-nt, and particularly preferably 23-nt. The inner region (Z), if containing the sequence suppressing expression, may further have an additional sequence at the 5' side and/or the 3' side of the sequence suppressing expression. The number of nucleotides of the additional sequence is, for example, 1- to 31-nt, preferably 1- to 21-nt, more preferably 1- to 11-nt, yet preferably 1- to 7-nt, and yet more preferably 1- to 3-nt.

The number of nucleotides in the 5' side region (Xc) is, for example, 1- to 49-nt, preferably 1- to 39-nt, and more preferably 1- to 29-nt. The number of nucleotides in the 3' side region (Yc) is, for example, 1- to 49-nt, preferably 1- to 39-nt, and more preferably 1- to 29-nt. It is preferable that the number of nucleotides of either of the 5' side region (Xc) and the 3' side region (Yc) be 1- to 4-nt, yet preferably 1-nt, 2-nt, or 3-nt.

The number of nucleotides in the inner region (Z), the 5' side region (Xc), and the 3' side region (Yc) can be represented, for example, by "Z≥Xc+Ye" in the formula (2). As a specific example, the number of nucleotides of "Xc+Yc" is, for example, the same as the inner region (Z), or less than the inner region (Z). In the latter case, "Z−(Xc+Yc)" is, for example, 1 to 10, preferably 1 to 4, and more preferably 1, 2, or 3. The "Z−(Xc+Yc)" corresponds to, for example, the number of nucleotides (F) of the free region (F) in the inner region (Z).

In the ssNc molecule, the lengths of the linker region (Lx) and the linker region (Ly) are not particularly limited. It is preferable that the linker region (Lx), for example, be long enough for the inner 5' side region (X) and the 5' side region (Xc) to form a duplex strand, and that the linker region (Ly), for example, be long enough for the inner 3' side region (Y) and the 3' side region (Yc) to form a duplex strand. If structure units of the linker region (Lx) and the linker region (Ly) contains a nucleotide, each of the number of nucleotides in the linker region (Lx) and the linker region (Ly) may be the same or different, and their nucleotide sequences may also be the same or different. The numbers of nucleotides in the linker region (Lx) and the linker region (Ly) have the lower limit of, for example, 1-nt, preferably 2-nt, and more preferably 3-nt, and the upper limit of, for example, 100-nt, preferably 80-nt, and more preferably 50-nt. Specific examples of the numbers of nucleotides in each of the linker regions include, but not limited to, 1- to 50-nt, 1- to 30-nt, 1- to 20-nt, 1- to 10-nt, 1- to 7-nt, and 1- to 4-nt.

The full length of the ssNc molecule is not particularly limited. In the ssNc molecule of the present invention, the sum of the number of nucleotides (the number of nucleotides of the full length) described above has the lower limit of, for example, 38-nt, preferably 42-nt, more preferably 50-nt, yet preferably 51-nt, and particularly preferably 52-nt; and the upper limit of, for example, 300-nt, preferably 200-nt, more preferably 150-nt, yet preferably 100-nt, yet more preferably 80-nt, and particularly preferably 60-nt. Specific examples of the sum of the number of nucleotides of the full length of the ssNc molecule include 38- to 300-nt, 42- to 200-nt, 50- to 150-nt, 51- to 100-nt, and 52- to 80-nt. In the ssNc molecule, the sum of the number of nucleotides except for those in the linker region (Lx) and the linker region (Ly) has the lower limit of, for example, 38-nt, preferably 42-nt, more preferably 50-nt, yet preferably 51-nt, and particularly preferably 52-nt; and the upper limit of, for example, 300-nt, preferably 200-nt, more preferably 150-nt, yet preferably 100-nt, yet more preferably 80-nt, and particularly preferably 60-nt. Specific examples of the sum of the number of nucleotides except for that in the linker region (Lx) include 38- to 300-nt, 42- to 200-nt, 50- to 150-nt, 51- to 100-nt, 52- to 80-nt, and 52- to 60-nt.

Examples of the nucleotide residues, which are the main structure units of the ssNc molecule, include ribonucleotide residues and deoxyribonucleotide residues. Examples of the nucleotide residues include unmodified nucleotide residues with no modification and modified nucleotide residues with modification. The ssNc molecules can, for example, contain the modified nucleotide residue, thereby enabling to improve nuclease resistance and raise stability. The ssNc molecule of the present invention may also, for example, further contain a non-nucleotide residue other than the nucleotide residue.

In the ssNc molecule, it is preferable that structure units of each of the inner region (Z), the 5' side region (Xc), and the 3' side region (Yc) be the nucleotide residues. Each of the regions is composed of, for example, residues of the following (1) to (3):
(1) an unmodified nucleotide residue,
(2) a modified nucleotide residue,
(3) an unmodified nucleotide residue and a modified nucleotide residue.

In the ssNc molecule, structure units of the linker region (Lx) and the linker region (Ly) are not particularly limited, and examples include the nucleotide residue and the non-nucleotide residue. The linker region, for example, may be composed of only the nucleotide residue, or may be composed of only the non-nucleotide residue, or may be composed of the nucleotide residue and the non-nucleotide residue. The linker region is composed of, for example, residues of the following (1) to (7).
(1) an unmodified nucleotide residue,
(2) a modified nucleotide residue,
(3) an unmodified nucleotide residue and a modified nucleotide residue,
(4) a non-nucleotide residue,
(5) a non-nucleotide residue and an unmodified nucleotide residue,
(6) a non-nucleotide residue and a modified nucleotide residue,
(7) a non-nucleotide residue, an unmodified nucleotide residue, and a modified nucleotide residue.

If the ssNc molecule has both of the linker region (Lx) and the linker region (Ly), for example, structure units of both may be the same or different. Specific examples include a form in which structure units of both linker regions are the nucleotide residues, a form in which structure units of both linker regions are the non-nucleotide residues, a form in which a structure unit of one region is the nucleotide residue while a structure unit of the other linker region is the non-nucleotide residue.

Examples of the ssNc molecules include a molecule composed of only the nucleotide residues, and a molecule containing the non-nucleotide residue other than the nucleotide residue. In the ssNc molecule of the present invention, the nucleotide residue, for example, may be only the unmodified nucleotide residues, or may be only the modified nucleotide residues, or may be both of the unmodified nucleotide residue and the modified nucleotide residue. If the ssNc molecule contains the unmodified nucleotide residue and the modified nucleotide residue, the number of the modified nucleotide residues is not particularly limited, but is, for example, "one or several", specifically, for example, 1 to 5, preferably 1 to 4, more preferably 1 to 3, and most preferably 1 or 2. If the ssNc molecule contains the non-nucleotide residue, the number of the non-nucleotide residues is not particularly limited, but is, for example, "one or several", particularly, for example, 1 to 8, 1 to 6, 1 to 4, 1, 2, or 3.

In the ssNc molecule, it is preferable that the nucleotide residue be, for example, a ribonucleotide residue. In this case, the ssNc molecule of the present invention is also referred to as, for example, "N-ssRNA molecule". Examples of the N-ssRNA molecules include a molecule composed of only the ribonucleotide residues, and a molecule containing the non-nucleotide residue other than the ribonucleotide residue. In the N-ssRNA molecule, the ribonucleotide residues, for example, may be only the unmodified ribonucleotide residues, may be only the modified ribonucleotide residues, or may contain both of the unmodified ribonucleotide residue and the modified ribonucleotide residue.

If the N-ssRNA molecule contains, for example, the modified ribonucleotide residue other than the unmodified ribonucleotide residue, the number of the modified ribonucleotide residues is not particularly limited, but is, for example, "one or several", particularly, for example, 1 to 5, preferably 1 to 4, more preferably 1 to 3, and most preferably 1 or 2. The modified ribonucleotide residue corresponding to the unmodified ribonucleotide residue may be, for example, the deoxyribonucleotide residue in which a ribose residue is substituted with a deoxyribose residue. If the N-ssRNA molecule contains, for example, the deoxyribonucleotide residue other than the unmodified ribonucleotide residue, the number of the deoxyribonucleotide residues is not particularly limited, and is, for example, "one or several", particularly, for example, 1 to 5, preferably 1 to 4, more preferably 1 to 3, and most preferably 1 or 2.

(5) Synthesis Method of ssPN Molecule and ssNc Molecule

Synthesis methods of ssPN molecules and ssNc molecules are not particularly limited, and can employ conventional known methods. Examples of the synthesis methods include a synthesis method by a genetic engineering technique, and a chemical synthesis method. Examples of genetic engineering techniques include an in vitro transcription synthesis method, a method using a vector, and a method by a PCR cassette. The vector is not particularly limited, and examples include non-viral vectors such as plasmids, and viral vectors. The chemical synthesis method is not particularly limited, and examples include a phosphoroamidite method and an H-phosphonate method. The chemical synthesis method can utilize, for example, a commercially-available automated nucleic acid synthesizer. In the chemical synthesis method, amidite is generally used. The amidite is not particularly limited, and examples of commercially-available amidites include RNA Phosphoramidites (2'-O-TBDMSi, trade name, Samchully Pharmaceutical Co., Ltd), ACE amidite, TOM amidite, CEE amidite, CEM amidite, and TEM amidite. Moreover, the ssPN molecule and ssNc molecule of the present invention can be manufactured according to manufacture methods described in WO2012/05368, WO2012/17919, WO2013/27843, and WO2016/159374.

(6) Antisense Polynucleotide

An antisense polynucleotide which is one of nucleic acids that suppress NEK6 gene expression will be described below.

An antisense polynucleotide is an antisense DNA and/or an antisense RNA, and exerts an effect by introducing into a cell, an antisense nucleic acid against the full length or a portion of a target gene RNA.

Mechanisms of expression inhibition by an antisense polynucleotide include:
1) steric inhibition of a translation initiation complex by directing to a region from the 5' cap site of mRNA to about 25-nt downstream of the initiation codon as a target sequence,
2) mRNA degradation via RNaseH with a single-strand DNA complementary to a target mRNA, and
3) splicing inhibition that directs to a boundary region between an exon and an intron of a pre-mRNA as a target sequence (mRNA maturation inhibition),
but the mechanism is not particularly limited as long as it suppresses NEK6 gene expression.

It is preferable that the antisense polynucleotide contain a modified nucleotide residue in view of binding stability with RNA (such as Tm value), mismatch sequence recognition capability, nuclease resistance, RNaseH activity, and the like.

For the modified nucleotide residue, modification on a ribose residue and a phosphate skeleton is preferable.

(7) miRNA

An miRNA which is one of nucleic acids that suppress NEK6 gene expression will be described below.

An miRNA participates in regulation of gene expression through inhibition of translation from mRNA to protein or degradation of mRNA. An miRNA is a short-strand (20- to 25-nt) non-coding RNA present within a cell. At first, an miRNA is transcribed as a single-strand pri-RNA that contains an miRNA and the complementary strand thereof and can take a hairpin loop structure from DNA. Next, the pri-RNA is cut out with a portion by an enzyme called Drosha within a nucleus, converted to a pre-RNA, and transported outside the nucleus. Then, the pre-RNA is further cleaved by Dicer, thereby functioning as an miRNA. The miRNA executes incomplete hybridization binding to the 3' untranslated region of mRNA to inhibit synthesis of protein encoded by the mRNA.

The miRNA that suppresses NEK6 gene expression can be obtained on the basis of gene name or mRNA sequence information of a target gene, for example, according to a database such as miRDB (http://mirdb.org/miRDB/index.html).

(8) Nucleotide Residues Used for Nucleic Acid

The nucleotide residue used for a nucleic acid as an active ingredient of the present invention, contains a sugar, a base, and phosphate as components. Examples of the nucleotide residues include ribonucleotide residues and deoxyribonucleotide residues. The ribonucleotide residue, for example, has a ribose residue as a sugar, and has adenine (A), guanine (G), cytosine (C), and uracil (U) as a base; and the deoxyribose residue, for example, has a deoxyribose residue as a sugar, and has adenine (A), guanine (G), cytosine (C), and thymine (T) as a base.

The nucleotide residues include unmodified nucleotide residues and modified nucleotide residues. In the unmodified nucleotide residue, each of the components is, for example, identical or substantially identical to naturally occurring one, and preferably identical or substantially identical to naturally occurring one in human body.

The modified nucleotide residue is, for example, a nucleotide residue in which the unmodified nucleotide residue is modified. In the modified nucleotide, for example, any of components in the unmodified nucleotide residue may be modified. In the present invention, "modification" represents, for example, substitution, addition, and/or deletion of the component, and substitution, addition, and/or deletion of an atom and/or a functional group in the component, and can be referred to as "alteration". Examples of the modified nucleotide residues include a naturally occurring nucleotide residue, and an artificially modified nucleotide residue. The naturally-originated modified nucleotide residue can refer to, for example, Limbach et al. (Limbach et al., 1994, Summary: the modified nucleosides of RNA, Nucleic Acids Res., 22:2183-2196). Additionally, the modified nucleotide residue may be, for example, an alternative residue of the nucleotide.

Examples of modifications of the nucleotide residues include modification of a ribose-phosphate skeleton (hereinafter referred to as a ribophosphate skeleton).

In the ribophosphate skeleton, for example, a ribose residue can be modified. The ribose residue can be, for example, modified at carbon of position 2', and can be specifically, for example, substituted at a hydroxyl group bound to carbon 2' by hydrogen or fluoro. By substituting a hydroxyl group on the carbon 2' by hydrogen, a ribose residue can be substituted with deoxyribose. The ribose residue can be, for example, substituted with a stereoisomer, and may be, for example, substituted with an arabinose residue.

The ribophosphate skeleton may be substituted, for example, a non-ribophosphate skeleton having a non-ribose residue and/or non-phosphate. Examples of the non-ribophosphate skeletons include an uncharged form of the ribophosphate skeleton. Examples of the nucleotide alternatives having substitution with the non-ribophosphate skeleton include morpholino, cyclobutyl, and pyrrolidine. In addition to these, examples of the alternatives include artificial nucleic acid monomer residues. Specific examples include PNA (peptide nucleic acid), LNA (Locked Nucleic Acid), and ENA (2'-O, 4'-C-Ethylenebridged Nucleic Acids), and a preferable one is PNA.

In the ribophosphate skeleton, for example, a phosphate group can be modified. In the ribophosphate skeleton, a phosphate group closest to a sugar residue is referred to as a phosphate group. The α phosphate group is negatively charged, and the electric charges are uniformly distributed over two oxygen atoms unbound to the sugar residue. Among four oxygen atoms in the α phosphate group, two oxygen atoms unbound to the sugar residue in a phosphodiester bond between nucleotide residues is also hereinafter referred to as "unbinding (non-linking) oxygen". In contrast, two oxygen atoms bound to the sugar residue in the phosphodiester bond between the nucleotide residues is hereinafter referred to as "binding (linking) oxygen". It is preferable that the α phosphate group be subjected to, for example, modification to undergo uncharging, or modification to allow the electric charge distribution on the unbinding atom to be an asymmetry type.

The phosphate group may be substituted, for example, at the unbinding oxygen. The oxygen can be, for example, substituted with any atom of S (sulfur), Se (selenium), B (boron), C (carbon), H (hydrogen), N (nitrogen), and OR (R is, for example, an alkyl group or an aryl group), and preferably substituted with S. It is preferable that in the unbinding oxygens, for example, both be substituted, and more preferably, both are substituted with S. Examples of the modified phosphate groups include phosphorothioate, phosphorodithioate, phosphoroselenate, boranophosphate, boranophosphate ester, phosphonatehydrogen, phosphoramidate, alkyl or arylphosphonate, and phosphotriester, and among them, phosphorodithioate in which both of the two unbinding oxygens are substituted with S is preferable.

The phosphate group may be substituted, for example, at the binding oxygen. The oxygen can be substituted with, for example, any atom of S (sulfur), C (carbon), and N (nitrogen). Examples of the modified phosphate groups include a cross-linking phosphoroamidate having substitution with N, a cross-linking phosphorothioate having substitution with S, and a cross-linking methylenephosphonate having substitution with C. It is preferable that substitution of the biding oxygen be made, for example, on at least one of the 5' end nucleotide residue and the 3' end nucleotide residue of the ssPN molecule of the present invention; in the case of the 5' side, substitution with C is preferable, and in the case of the 3' side, substitution with N is preferable.

The phosphate group may be substituted with, for example, the phosphorous-free linker described above. The linkers include, for example, siloxane, carbonate, carboxymethyl, carbamate, amide, thioether, ethyleneoxide linker, sulfonate, sulfonamide, thioformacetal, formacetal, oxime, methyleneimino, methylenemethylimino, methylenehydrazo, methylenedimethylhydrazo, and methyleneoxymethylimino, and preferably include a methylenecarbonylamino group and a methylenemethylimino group.

Examples of modifications of the end nucleotide residue include addition of another molecule. Examples of the other molecules include functional molecules such as a labelling substance and a protecting group as mentioned above. Examples of the protecting groups include S (sulfur), Si (silicon), B (boron), and an ester-containing group.

The other molecule, for example, may be added to a phosphate group of the nucleotide residue, or may be added to the phosphate group or the sugar residue via a spacer. An end atom of the spacer can be added to or substituted with, for example, the binding oxygen of the phosphate group, or O, N, S, or C of a sugar residue. It is preferable that the binding site of the sugar residue be, for example, C of position 3' or C of position 5', or an atom bound thereto. The spacer can also be added to or substituted with, for example, an end atom of the nucleotide alternative such as the PNA.

The spacer is not particularly limited, and may contain, for example, $-(CH_2)_n-$, $-(CH_2)_nN-$, $-(CH_2)_nO-$, $-(CH_2)_nS-$, $O(CH_2CH_2O)_nCH_2CH_2H$, non-base sugar, amide, carboxy, amine, oxyamine, oxyimine, thioether, disulfide, thiourea, sulfonamide, morpholino, and a biotin reagent, a fluorescein reagent. In the formula, n is a positive integer, and n=3 or 6 is preferable.

In addition to these, examples of the molecules to be added to the end include dyes, intercalaters (e.g., acridine), cross-linkers (e.g., psoralen, mitomycin C), porphyrin (TPPC4, texaphyrin, sapphyrin), polycyclic aromatic hydrocarbon (e.g., fenadine, dihydrofenadine), artificial endonucleases (e.g., EDTA), lipophilic carriers (e.g., cholesterol, cholic acid, adamantaneacetic acid, 1-pyrenebutyric acid, dihydrotestosteron, 1,3-bis-O(hexadecyl)glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyl)cholic acid, dimethoxytrityl, or phenoxazine) and peptide complexes (e.g., Antennapedia peptides, Tat peptides), alkylators, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption accelerators (e.g., aspirin, vitamin E, folic acid), and synthetic ribonucleases (e.g., imidazole, bisimidazole, histamine, imidazole clusters, acridine-imidazole complexes, tetraaza macro-cyclic Eu$^{3+}$ complexes).

The nucleic acid molecule may have modification of the 5' end with, for example, a phosphate group or a phosphate group analogue. Examples of the phosphate group include 5' monophosphate ((HO)$_2$(O)P—O-5'), 5' diphosphate ((HO)$_2$(O)P—O—P(HO)(O)—O-5'), 5' triphosphate ((HO)$_2$(O)P—O—(HO)(O)P—O—P(HO)(O)—O-5'), 5'-guanosine caps (7-methylated or unmethylated, 7m-G-O-5'-(HO)(O)P—O—(HO)(O)P—O—P(HO)(O)—O-5'), 5'-adenosine caps (Appp), any modified or unmodified nucleotide cap structure (N—O-5'-(HO)(O)P—O—(HO)(O)P—O—P(HO)(O)—O-5'), 5'-thiophospate (phosphorothioate: (HO)$_2$(S)P—O-5'), 5'-dithiophosphate (phosphorodithioate: (HO)(HS)(S)P—O-5'), 5'-phosphorothiolic acid ((HO)$_2$(O)P—S-5'), sulfur-substituted monophosphate, diphosphate, and triphosphate (such as 5'-α-thiotriphosphate or 5'-γ-thiotriphosphate), 5'-phosphoramidate ((HO)$_2$(O)P—NH-5', (HO)(NH$_2$)(O)P—O-5'), 5'-alkylphosphonate (e.g., RP(OH)(O)—O-5', (OH)$_2$(O)P-5'-CH$_2$, wherein R is alkyl [such as methyl, ethyl, isopropyl, or propyl]), and 5'-alkyletherphosphate (e.g., RP(OH)(O)—O-5', wherein R is alkylether [such as methoxymethyl or ethoxymethyl]).

In the nucleotide residue, the base is not particularly limited. The base may be, for example, a natural base or an unnatural base. The base may be, for example, naturally-originated or a synthesized one. The base can employ, for example, a common base, or a modified analogue thereof.

Examples of the bases include purine bases such as adenine and guanine, and pyrimidine bases such as cytosine, uracil, and thymine. The bases otherwise include inosine, thymine, xantine, hypoxantine, nubularine, isoguanisine, and tubercidine. Examples of the bases include alkyl derivatives such as 2-amino adenine, 6-methylated purine; alkyl derivatives such as 2-propylated purine; 5-halouracil and 5-halocytosine; 5-propynyluracil and 5-propynylcytosine; 6-azouracil, 6-azocytosine, and 6-azothymine; 5-uracil (pseudouracil), 4-thiouracil, 5-halouracil, 5-(2-aminopropyl)uracil, 5-aminoallyl uracil; 8-haloate, aminated, thiolated, thioalkylated, hydroxylated, and other 8-substituted purines; 5-trifluoromethylated and other 5-substituted pyrimidines; 7-methylguanine; 5-substituted pyrimidine; 6-azapyrimidine; N-2, N-6, and O-6 substituted purine (including 2-amino propyladenine); 5-propynyluracil and 5-propynylcytosine; dihydrouracil; 3-deaza-5-azacytosine; 2-amino purine; 5-alkyl uracil; 7-alkyl guanine; 5-alkyl cytosine; 7-deazaadenine; N6,N6-dimethyladenine; 2,6-diaminopurine; 5-amino-allyl-uracil; N3-methyluracil; substituted 1,2,4-triazole; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl)uracil; 3-methylcytosine; 5-methylcytosine; N$^4$-acetylcytosine; 2-thiocytosine; N6-methyladenine; N6-isopentyladenine; 2-methylthio-N6-isopentenyladenine; N-methylguanine; and O-alkylate bases. Furthermore, examples of purines and pyrimidines include those disclosed in U.S. Pat. No. 3,687,808, "Concise Encyclopedia Of Polymer Science And Engineering", p. 858-859, ed. Kroschwitz J. I., John Wiley & Sons, 1990, and Englisch et al., Angewandte Chemie, International Edition, 1991, 30, p. 613.

(9) Definition of Other Terms

The terms used in descriptions of the nucleic acids as an active ingredient of the present invention, linkers, and the like are those commonly used in the art, and for example, can be shown as follows.

In the present invention, "alkyl" includes, for example, linear or branched alkyl groups. The number of carbons of the alkyl is not particularly limited, but is, for example, 1 to 30, and preferably 1 to 6 or 1 to 4. Examples of the alkyl groups include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl. Preferably, examples include methyl, ethyl, n-propyl, isopropyl, n-butyl, isobutyl, sec-butyl, tert-butyl, n-pentyl, isopentyl, neopentyl, n-hexyl, and isohexyl.

In the present invention, "alkenyl" includes, for example, linear or branched alkenyls. The alkenyl includes those having one or more double bonds or the like in the alkyl. The number of carbons of the alkenyl is not particularly limited, but is, for example, similar to that on the alkyl, and preferably 2-8. Examples of the alkenyl include vinyl, 1-propenyl, 2-propenyl, 1-butenyl, 2-butenyl, 3-butenyl, 1,3-butadienyl, and 3-methyl-2-butenyl.

In the present invention, "alkynyl" includes, for example, linear or branched alkynyls. The alkynyl includes those having one or more triple bonds or the like in the alkyl. The number of carbons of the alkynyl is not particularly limited, but is, for example, similar to that of the alkyl, and preferably 2 to 8. Examples of the alkynyl include ethynyl, propynyl, and butynyl. The alkynyl may further have, for example, one or more double bonds.

In the present invention, "aryl" includes, for example, monocyclic aromatic hydrocarbon groups and polycyclic aromatic hydrocarbon groups. Examples of the monocyclic aromatic hydrocarbon groups include phenyl. Examples of the polycyclic aromatic hydrocarbon groups include 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl. Examples preferably include phenyl, and naphthyl such as 1-naphthyl and 2-naphthyl.

In the present invention, "heteroaryl" includes, for example, monocyclic aromatic heterocyclic groups and condensed aromatic heterocyclic groups. Examples of the heteroaryl include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridadinyl (e.g., 3-pyridadinyl, 4-pyridadinyl), pyrimidinyl (e.g., 2-pyrimidinyl, 4-pyrimidinyl, 5-pyrimidinyl), furazanyl (e.g., 3-furazanyl), pyradinyl (e.g., 2-pyradinyl), oxadiazolyl (e.g., 1,3,4-oxadiazol-2-yl), benzofuryl (e.g., 2-benzo[b]furyl, -benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzoimidazolyl, 2-benzoimidazolyl, 4-benzoimidazolyl, 5-benzoimidazolyl), dibenzofuryl, benzoxazolyl, benzothiazolyl, quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phtharadinyl (e.g., 1-phtharadinyl, 5-phtharadinyl, 6-phtharadinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, puteridinyl (e.g., 2-puteridinyl, 4-puteridinyl, 6-puteridinyl, 7-puteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, and phenadinyl (e.g., 1-phenadinyl, 2-phenadinyl) or phenothiadinyl (e.g., 1-phenothiadinyl, 2-phenothiadinyl, 3-phenothiadinyl, 4-phenothiadinyl).

In the present invention, "cycloalkyl" is, for example, a cyclic saturated hydrocarbon group, in which the number of carbons is, for example, 3 to 15. Examples of the cycloalkyl include cyclopropyl, cyclobutyl, cyclopentyl, cyclohexyl, cycloheptyl, cyclooctyl, bridged cyclic hydrocarbon groups, and spiro hydrocarbon groups, and preferably include cyclopropyl, cyclobutyl, cyclopentyl, cyclohexyl, and bridged cyclic hydrocarbon groups.

In the present invention, examples of "bridged cyclic hydrocarbon groups" include bicyclo[2.1.0]pentyl, bicyclo[2.2.1]heptyl, bicyclo[2.2.2]octyl and bicyclo[3.2.1]octyl, tricyclo[2.2.1.0]heptyl, bicyclo[3.3.1]nonane, 1-adamantyl, and 2-adamantyl.

In the present invention, examples of "spiro hydrocarbon groups" include spiro[3.4]octyl.

In the present invention, "cycloalkenyl" encompasses, for example, a cyclic unsaturated aliphatic hydrocarbon group, in which the number of carbons is, for example, 3 to 7. Examples of the groups include cyclopropenyl, cyclobutenyl, cyclopentenyl, cyclohexenyl, and cycloheptenyl, and are preferably, cyclopropenyl, cyclobutenyl, cyclopentenyl, cyclohexenyl. The cycloalkenyl also include, for example, a bridged cyclic hydrocarbon group and spiro hydrocarbon group having an unsaturated bond within a ring.

In the present invention, examples of "arylalkyl" include benzyl, 2-phenetyl, and naphthalenylmethyl; examples of "cycloalkyl alkyl" or "cyclylalkyl" include cyclohexylmethyl and adamantylmethyl; and examples of "hydroxyalkyl" include, hydroxymethyl and 2-hydroxyethyl.

In the present invention, "alkoxy" includes the alkyl —O— group, and examples include methoxy, ethoxy, n-propoxy, isopropoxy, and n-butoxy; examples of "alkoxyalkyl" include methoxymethyl; and examples of "amino alkyl" include 2-amino ethyl.

In the present invention, examples of "heterocyclyl" include 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazolinyl, 2-imidazolinyl, 4-imidazolinyl, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperadinyl, 2-piperadinyl, piperadinone, 2-morpholinyl, 3-morpholinyl, morpholino, tetrahydropyranyl, and tetrahydrofuranyl.

In the present invention, examples of "heterocyclylalkyl" include piperidinylmethyl and piperadinylmethyl; examples of "heterocyclylalkenyl" include 2-piperidinylethenyl; and examples of "heteroarylalkyl" include pyridylmethyl and quinolin-3-ylmethyl.

In the present invention, "silyl" includes a group represented by formula $R_3Si$—, in which R can be independently selected from alkyl, aryl, and cycloalkyl described above, and examples include a trimethylsilyl group and a tert-butyldimethylsilyl group; examples of "silyloxy" include a trimethylsilyloxy group; and examples of "silyloxyalkyl" include trimethylsilyloxymethyl.

In the present invention, examples of "alkylene" include methylene, ethylene, and propylene.

In the present invention, the various kinds of groups mentioned above may be substituted. Examples of the substituents include hydroxy, carboxy, halogen, halogenated alkyl (e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkyl alkyl (e.g., cyclohexylmethyl, adamantylmethyl), cycloalkenyl (e.g., cyclopropenyl), aryl (e.g., phenyl, naphthyl), arylalkyl (e.g., benzyl, phenetyl), heteroaryl (e.g., pyridyl, furyl), heteroarylalkyl (e.g., pyridylmethyl), heterocyclyl (e.g., piperidyl), heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyl oxycarbonyl (e.g., methoxycarbonyl, ethoxycarbonyl, tert-butoxycarbonyl), arylalkyloxy (e.g., benzyloxy), amino (alkylamino [e.g., methylamino, ethylamino, dimethylamino], acylamino [e.g., acetylamino, benzoylamino], arylalkylamino [e.g., benzylamino, tritylamino], hydroxyamino), alkylaminoalkyl (e.g., diethylaminomethyl), sulfamoyl, and oxo.

(10) Phosphorylation Inhibitor of SMAD2/3 Protein

Inhibition of the phosphorylation of SMAD2/3 protein means that the phosphorylation of SMAD2 and/or SMAD3 promoted by TGF-β stimulation is inhibited (controlled). SMAD2/3 is one of R-SMADs (receptor regulated SMADs) that undergo phosphorylation by TGF-β type I receptor, and after stimulation by TGF-β, phosphorylated (activated) SMAD2 and SMAD3 immigrate together with SMAD4, which is Co-SMAD (common partner SMAD), into the nucleus. A shown in Example 4, the inventors found that NEK6 protein interacts with SMAD2/3 protein within a cell and promotes the phosphorylation of SMAD2/3 protein. The phosphorylated SMAD2/3 protein forms a SMAD protein complex, immigrates into the nucleus, and enhances transcription of α-SMA, α2-collagen, interferon β, interleukine-5, VEGF, and the like.

Accordingly, inhibition of SMAD signal system by the phosphorylation inhibitor of SMAD2/3 protein of the present invention enables transcriptional control of α-SMA, α2-collagen, interferon β, and the like, and is, in turn, useful for suppressing differentiation of a fibroblast, a hepatic stellate cell, or the like into a myofibroblast, controlling matrix synthesis caused by fibroblasts or the like, and regulating inflammatory and immune reactions, and the like, in a wound healing process.

(11) Therapeutic Agent for Fibrosis

The therapeutic agent for fibrosis of the present invention is a therapeutic agent for hepatic fibrosis, hepatic cirrhosis, viral hepatitis, autoimmune hepatitis, primary biliary hepatitis, nonalcoholic steatohepatitis, alcoholic liver disease, primary sclerosing cholangitis, hemochromatosis, Wilson's disease, α1-antitrypsin deficiency, non-viral congestive hepatic cirrhosis, drug-induced hepatic disorder, pancreatitis, pancreatic fibrosis, retinal fibrosis, vocal fold scarring, vocal cord mucosal fibrosis, laryngeal fibrosis, pulmonary fibrosis, pneumonitis, idiopathic pulmonary fibrosis, non-specific pneumonitis, idiopathic organizing pneumonia, desquamative pneumonitis, respiratory bronchiolitis-associated pneumonitis, acute pneumonitis, lymphocytic pneumonitis, sarcoidosis, chronic eosinophilic pneumonia, acute eosinophilic pneumonia, lymphangioleiomyomatosis, pulmonary alveolar proteinosis, Hermansky-Pudlak syndrome, pulmonary Langerhans cell histiocytosis, siderosis, amyloidosis, pulmonary alveolar microlithiasis, hypersensitivity pneumonitis, pneumoconiosis, infectious pulmonary disease, drug-induced pneumonia, radiation pneumonia, cystic fibrosis, myelofibrosis, kidney fibrosis, chronic renal failure, diabetic nephropathy, chronic glomerulonephritis, malignant nephrosclerosis, polycystic kidney, drug-induced renal disorder, retroperitoneal fibrosis, collagenosis, scleroderma, congenital dyskeratosis, nephrogenic systemic fibrosis, and additionally, diseases widely associated with fibrogenesis including airway fibrogenesis, intestinal fibrogenesis, urinary bladder fibrogenesis, prostatic fibrogenesis, and dermal fibrogenesis. Preferably, it is for hepatic fibrosis, hepatic cirrhosis, pulmonary fibrosis, pneumonitis, kidney fibrosis, and chronic renal failure.

An administration method of the therapeutic agent for fibrosis of the present invention is not particularly limited, but it is preferable that it be parenteral administration such as inhalation, intravenous injection, or transdermal administration. The dosage of the nucleic acid molecule of the present invention in a therapeutic method of the present invention is not particularly limited as long as it is an effective amount for treating the disease described above, and varies depending on the type of disease, the degree of severity, age, body weight, route of administration, and the like, but may be typically about 0.0001 to about 100 mg/kg by body weight per once for an adult, for example, about 0.001 to about 10 mg/kg by body weight, and preferably about 0.005 to about 5 mg/kg by body weight. Such amount can be administered at an interval of, for example, three times a day to once a month, preferably once a day to a week. The therapeutic agent for fibrosis of the present invention is typically formulated as an appropriate pharmaceutical composition with a pharmaceutically acceptable carrier and administered in an oral or parenteral form.

Hereinafter, the present invention will be described in detail with Examples and the like, but the present invention is not limited to these. Incidentally, culture condition was at 37° C., under 5% $CO_2$. Additionally, unless otherwise stated, a medium used for human pulmonary fibroblast line LL29 cells was F-12K medium (Gibco®) containing 10% FCS; a medium used for human primary hepatic stellate cells (ScienCell Research Laboratories, Inc.) was stellate cell medium (ScienCell Research Laboratories, Inc.) containing 2% FCS and 1% Stellate cell growth supplement (SteCGS, ScienCell Research Laboratories, Inc.).

EXAMPLES

Example 1: NEK6 Knockdown Using siRNAs

To human pulmonary fibroblast line LL29 cells established from the lung of an IPF patient, siRNAs for human NEK6 (ON-TARGET plus SMART pool siRNA, Dharmacon Inc., or Stealth RNAi siRNA, Thermo Fisher Scientific, Inc.) were transfected using Lipofectamine RNAi MAX (Invitrogen™). 24 hours after transfection, the medium was changed from F-12K medium (Gibco®) containing 10% FCS to F-12K medium containing 0.1% BSA. 72 hours after transfection, RNAs were extracted from the cells transfected with the siRNAs, using RNeasy Mini Kit (Qiagen N.V.). The RNAs thus obtained were subjected to reverse transcription using High Capacity cDNA Reverse Transcription Kit (Applied Biosystems®) to obtain cDNAs. The cDNAs thus obtained were subjected to real-time PCR using TaqMan Gene Expression Assays (Applied Biosystems®) to examine influence on the transcript amount of NEK6 gene by NEK6 knockdown. The transcript amount of NEK6 gene was calculated by dividing a measurement value in NEK6 Taqman Probe (HS00205221_m1, Applied Biosystems®) by a measurement value in 18s Probe. As the 18s Probe, the following custom synthesized 18s MGB Probe, custom synthesized 18s Primer 1, and custom synthesized 18s Primer 2 were mixed so as to be 0.2 µM, 0.4 µM, and 0.4 µM, respectively, and subjected to real-time PCR.

Custom synthesized 18s MGB Probe (Applied Biosystems®):

```
                                        (SEQ ID NO: 57)
     5'-ATTGGAGGGCAAGTCTGGTGCCAGC-3'
```

Custom synthesized 18s Primer 1 (Thermo Fisher Scientific, Inc.):

```
                                        (SEQ ID NO: 58)
           5'-CGGCTACCACATCCAAGGAAG-3'
```

Custom synthesized 18s Primer 2 (Thermo Fisher Scientific, Inc.):

```
                                        (SEQ ID NO: 59)
              5'-GCTGGAATTACCGCGGCT-3'
```

As siRNA sequences, ON-TARGET plus SMART pool siRNA (mixing SEQ ID NOs: 51 to 54 in equal amounts) and Stealth RNAi siRNA (SEQ ID NO: 55) were used.

```
     <ON-TARGET plus SMART pool siRNA>
                                        (SEQ ID NO: 51)
        siNEK6:  5'-CUGUCCUCGGCCUAUCUUC-3'

(SEQ ID NO: 52)
        siNEK6:  5'-UAUUUGGGUGGUUCAGUUG-3'

(SEQ ID NO: 53)
        siNEK6:  5'-CAACUCCAGCACAAUGUUC-3'
```

-continued (SEQ ID NO: 54)
siNEK6: 5'-UACUUGAUCAUCUGCGAGA-3'

<Stealth RNAi siRNA>
(SEQ ID NO: 55)
siNEK6: 5'-AAGUACUUCCAUACUGUCCUCUCC-3'

Figure 6:
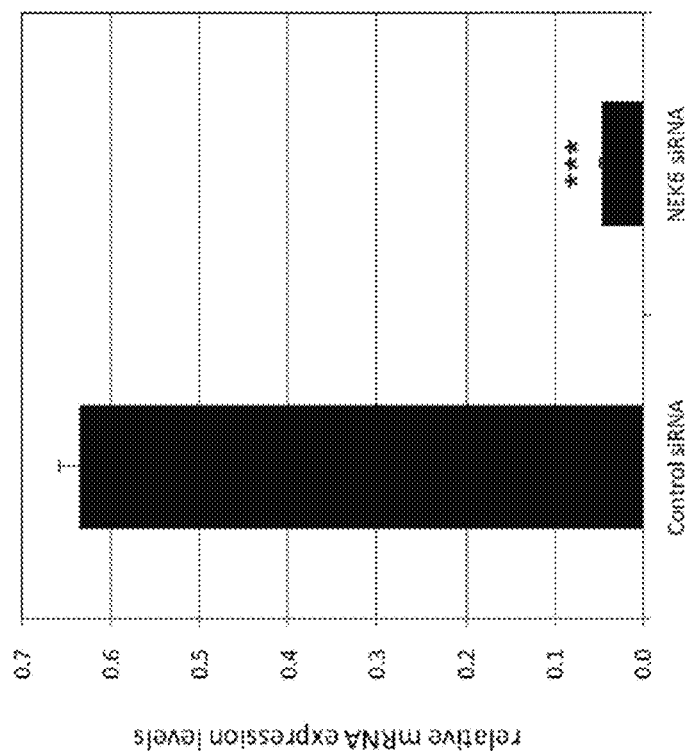
FIGS. 6a and 6b are graphs showing the amounts of the transcripts of NEK6 gene when siRNAs were introduced.
Figure 6:
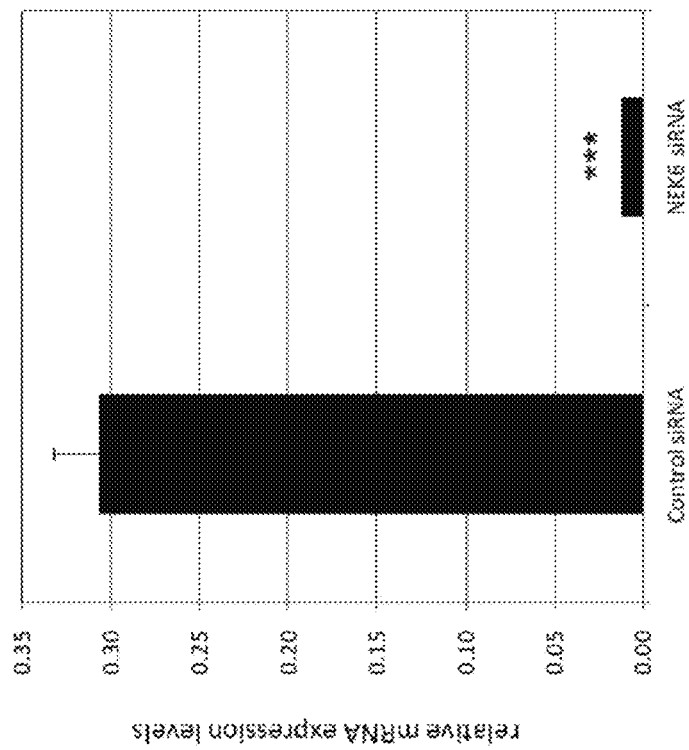

FIG. 6a shows results of real-time PCR of NEK6 when ON-TARGET plus SMART pool siRNA for NEK6 was introduced, and FIG. 6b shows results of NEK6 when Stealth RNAi siRNA for NEK6 was introduced. Introduction of NEK6 siRNAs suppressed the transcript amount of NEK6 gene. Consequently, it was shown that the NEK6 siRNAs used suppressed efficiently the expression of a target gene.

Example 2: Influence of NEK6 Knockdown on Phosphorylation of SMAD2/3 Protein

In order to investigate possibility that NEK6 protein may control TGF-β signal, the amount of phosphorylated SMAD2/3 was analyzed in cells transfected with NEK6 siRNAs.

To human pulmonary fibroblast line LL29 cells established from the lung of an IPF patient, ON-TARGET plus SMART pool siRNA for human NEK6 (Dharmacon Inc.) or Stealth RNAi siRNA (Thermo Fisher Scientific, Inc.) were transfected using Lipofectamine RNAi MAX. 24 hours after transfection, the medium was changed from F-12K medium containing 10% FCS to F-12K medium containing 0.1% BSA. 48 hours after transfection, human TGF-β protein (PeproTech, Inc.) was added so as to provide a final concentration of 5 ng/mL. Two hours after TGF-β addition, the cells were lysed with 2×SDS sample buffer (100 mM Tris-HCl, pH 6.8, 4% SDS, 6 M Urea, 12% Glycerol, 2% protease inhibitor cocktail [Nacalai Tesque Inc.], 1% phosphatase inhibitor cocktail [Nacalai Tesque Inc.]) to give a cell extract. To the cell extract thus obtained, β-Mercaptoethanol and Bromophenol blue were added so as to provide final concentrations of 5% and 0.025%, respectively, and then heated at 95° C. for 4 minutes to give a sample. Using the sample thus obtained, SDS-PAGE was performed to separate proteins contained in the sample in accordance with their sizes. Then, the separated proteins were transferred onto a PVDF membrane, and subjected to Western blotting with an anti-phosphorylated SMAD3 antibody (Cell Signaling Technology, Inc.), an anti-phosphorylated SMAD2 antibody (Cell Signaling Technology, Inc.), an anti-SMAD2/3 antibody (Cell Signaling Technology, Inc.), an anti-NEK6 antibody (Santa Cruz Biotechnology Inc.), and an anti-β-Actin antibody (Sigma-Aldrich Co. LLC.)

FIG. 7a shows results of Western blot of phosphorylated SMAD3 protein when NEK6 was knockdown. By using NEK6 siRNAs, the amount of NEK6 protein was decreased, and the amount of phosphorylated SMAD3 that is elevated by TGF-β was decreased. At this time, the amount of total SMAD3 protein did not change. Meanwhile, FIG. 7b shows results of Western blot of phosphorylated SMAD2 protein when NEK6 was knockdown. By using NEK6 siRNAs, the amount of NEK6 protein was decreased, and the amount of phosphorylated SMAD2 that is elevated by TGF-β was decreased. At this time, the amount of total SMAD2 protein did not change.

Consequently, it was shown that phosphorylation of SMAD2/3 protein is suppressed by NEK6 knockdown.

Example 3: Interaction Between NEK6 Protein and SMAD3 Protein within a Cell

In order to investigate whether NEK6 protein would interact with SMAD3 and phosphorylates SMAD3 within a cell, co-immunoprecipitation was performed.

To human pulmonary fibroblast line LL29 cells established from the lung of an IPF patient, an expression vector in which human NEK6 was cloned (pEZ-M02 Nek6, GeneCopoeia, Inc.) and an expression vector in which FLAG-tag-labeled human SMAD3 was cloned (pEZ-M11 Flag-hSmad3, GeneCopoeia, Inc.) were transfected using X-treme GENE HP (Roche Diagnostics K. K). 24 hours after transfection, the medium was changed. 48 hours after transfection, the cells were recovered with lysis buffer (175 mM NaCl, 50 mM HEPES, pH 7.6, 0.1% NP40, 0.2 mM EDTA, pH 8.0, 1.4 mM β-Mercaptoethanol, 1% protease inhibitor cocktail, 1% phosphatase inhibitor cocktail), and supernatant was obtained by centrifugation. To the supernatant, TrueBlot Anti-Goat IgIP Beads (Rockland Immunochemicals Inc.) was added and subjected to centrifugation to eliminate non-specific binding. To the supernatant thus obtained, a normal goat IgG (Santa Cruz Biotechnology Inc.) as a control or an anti-NEK6 antibody was added and incubated at 4° C. overnight, and then TrueBlot Anti-Goat IgIP Beads was added and incubated at 4° C. for 4 hours. After centrifugation and removal of supernatant, the TrueBlot Anti-Goat IgIP Beads was washed with lysis buffer to eliminate non-specific binding. To the TrueBlot Anti-Goat IgIP Beads, 2×SDS PAGE loading buffer (100 mM Tris-HCl, pH 6.8, 4% SDS, 20% Glycerol, 0.2% Bromophenol blue, 50 mM DTT) was added and heated at 95° C. for 5 minutes, and coimmunoprecipitate contained in the supernatant was recovered. For the coimmunoprecipitate with the anti-NEK6 antibody, Western blotting was performed with an anti-SMAD3 antibody (Cell Signaling Technology, Inc.) or an anti-NEK6 antibody, and subjected to detection whether NEK6 protein and SMAD3 protein would be co-immunopresipitated.

FIG. 8a shows results of co-immunoprecipitation with the anti-NEK6 antibody. NEK6 protein and SMAD3 protein were detected from the coimmunoprecipitate.

In order to analyze whether SMAD3 protein interacts with NEK6 and is phosphorylated within a cell, an expression vector for human NEK6 and an expression vector for FLAG-tag-labeled human SMAD3 were transfected into LL29 cells. 24 hours after transfection, the medium was changed. 48 hours after transfection, the cells were recovered with lysis buffer (250 mM NaCl, 50 mM HEPES, pH 7.6, 0.1% NP40, 0.2 mM EDTA, pH8.0, 1.4 mM β-Mercaptoethanol, 1% protease inhibitor cocktail, 1% phosphatase inhibitor cocktail), and supernatant was obtained by centrifugation. To the supernatant thus obtained, Anti-FLAG M2 Affinity Gel (Sigma-Aldrich Co. LLC.) was added and incubated at 4° C. overnight. Then centrifugation was performed to remove supernatant. The Anti-FLAG M2 Affinity Gel was washed with lysis buffer to eliminate non-specific binding. To the Anti-FLAG M2 Affinity Gel, 2×SDS PAGE loading buffer (100 mM Tris-HCl, pH 6.8, 4% SDS, 20% Glycerol, 0.2% Bromophenol blue, 50 mM DTT) was added and heated at 95° C. for 4 minutes, and coimmunoprecipitate contained in the supernatant was recovered. The coimmunoprecipitate thus obtained was separated with SDS-PAGE on the basis of the sizes, followed by transfer to a PVDF membrane, and subjected to Western blotting for the coimmunoprecipitate by Anti-FLAG M2 Affinity Gel using an anti-phosphorylated SMAD3 antibody, an anti-FLAG antibody (Sigma-Aldrich Co. LLC.), and an anti-NEK6 antibody, to detect whether NEK6 protein and phosphorylated SMAD3 protein would be co-immunoprecipitated.

FIG. 8b shows results of co-immunoprecipitation by the anti-FLAG antibody. NEK6 protein and FLAG-SMAD3 protein were detected from coimmunoprecipitate. Moreover, transfection of a human NEK6 expression vector caused the amount of phosphorylated SMAD3 protein to be elevated.

Since SMAD3 protein was detected in coimmunoprecipitate by an anti-NEK6 antibody, and conversely, NEK6 was detected in coimmunoprecipitate by an anti-FLAG antibody, it was shown that NEK6 protein and SMAD3 protein interact within a cell and form a complex. Furthermore, since the amount of phosphorylated SMAD3 protein was elevated by transfection of a human NEK6 expression vector, it was shown that NEK6 protein phosphorylates SMAD3 protein within a cell.

Example 4: SMAD3 Protein Phosphorylation by NEK6 Protein

Possibility that NEK6 protein may directly phosphorylate SMAD3 protein as a substrate was investigated using purified proteins of NEK6 and SMAD3.

His-fusion NEK6 protein (Eurofins Scientific SE) and GST-fusion SMAD3 protein (Sigma-Aldrich Co. LLC.) were mixed with reaction solvent (150 µM ATP, 50 mM HEPES, 150 mM NaCl, 0.1% Triton X-100, 10 mM MgCl$_2$, 1 mM DTT, 1% phosphatase inhibitor cocktail), and incubated at 30° C. for 45 minutes. To the reaction solution, 2×SDS sample buffer containing 5% β-Mercaptoethanol and 0.025% Bromophenol blue were added in equal amounts to terminate the reaction, and then heated at 95° C. for 5 minutes to give a sample. Using the sample thus obtained, SDS-PAGE was performed to separate proteins contained in the reaction solution in accordance with their sizes. Then, the separated proteins were transferred onto a PVDF membrane, and subjected to Western blotting with an anti-phosphorylated SMAD3 antibody and an anti-GST antibody (Santa Cruz Biotechnology Inc.), an anti-NEK6 antibody.

Figure 9:
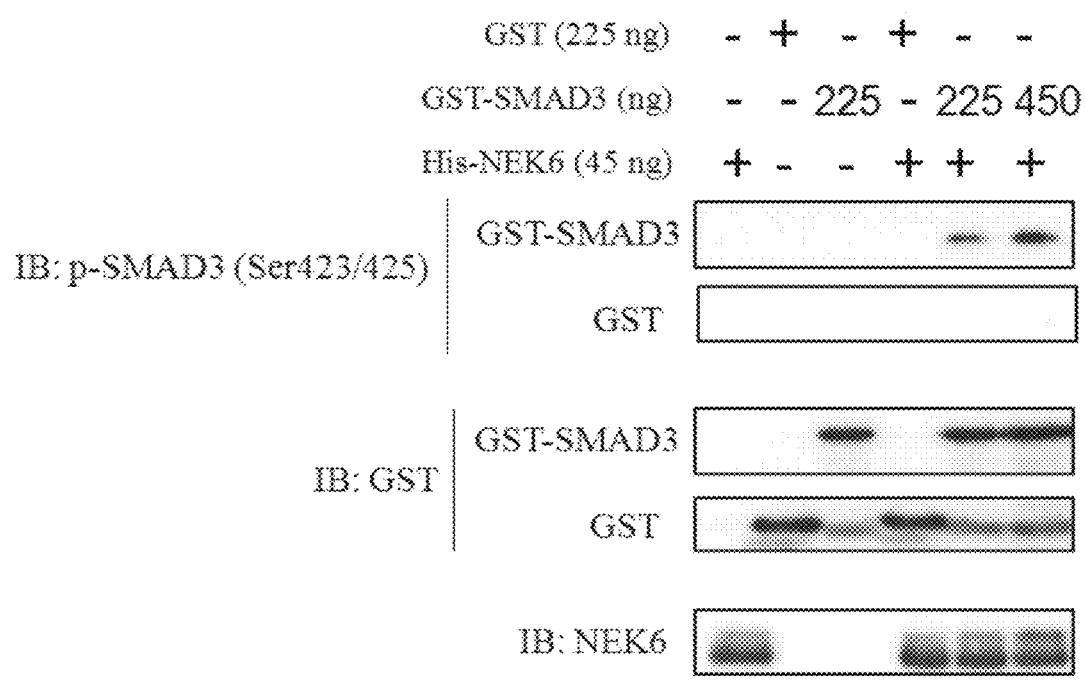
FIG. 9 represents results of Western blot for phosphorylated SMAD3 protein when His-fused NEK6 protein and GST-fused SMAD3 protein were reacted.

FIG. 9 shows results of Western blot of phosphorylated SMAD3 protein, when His-fusion NEK6 protein and GST-fusion SMAD3 protein were reacted. By using NEK6 protein, the amount of phosphorylated SMAD3 was elevated. Consequently, it was shown that NEK6 protein directly phosphorylates SMAD3 protein as a substrate.

Example 5: Influence on Transcriptional Activity of SMAD Protein Complex by NEK6 Knockdown In order to investigate whether NEK6 protein would also control transcriptional activity that generates after nuclear translocation of SMAD protein complex, a luciferase reporter assay with a DNA binding sequence of SMAD protein complex and luciferase gene was performed. Furthermore, Western blotting was performed using LL29 cells prepared simultaneously, to check for NEK6 knockdown.

To human pulmonary fibroblast line LL29 cells established from the lung of an IPF patient, ON-TARGET plus SMART pool siRNA (Dharmacon Inc.), which is an siRNA for human NEK6, was transfected using Lipofectamine RNAi MAX. 24 hours after transfection of the siRNA, the medium was changed from F-12K medium containing 10% FCS to F-12K medium containing 0.4% FCS. 48 hours after transfection of the siRNA, an expression vector in which a DNA binding sequence of SMAD protein complex (SMAD biding element [SBE]) and firefly luciferase gene (pTL-SBE-luc: 5'-AGTATGTCTAGACTGAAGTATGTCTA-GACTGAAGTATGTCTAG ACTGA-3' [SEQ ID NO: 60], Panomics Inc.) were cloned, and a vector for calibration for a reporter assay which contains wildtype *Renilla* luciferase (pRL-TK: Promega Corporation) were transfected using Lipofectamine LTX with PLUS reagent (Thermo Fisher Scientific Inc). Two hours after transfection of the expression vectors, human TGF-β protein was added so as to provide a final concentration of 10 ng/mL. 24 hours after addition of TGF-β, the cells were lysed with 2×SDS sample buffer (100 mM Tris-HCl, pH 6.8, 4% SDS, 6 M Urea, 12% Glycerol, 2% protease inhibitor cocktail, 1% phosphatase inhibitor cocktail). Proteins contained in the cell extract thus obtained were separated by SDS-PAGE, followed by transfer of the proteins onto a PVDF membrane, and subjected to Western blotting with an anti-SMAD3 antibody, an anti-NEK6 antibody, and an anti-Vinculin antibody. Meanwhile, LL29 cells prepared in a similar manner as described above were recovered in accordance with Dual-Luciferase Reporter Assay System (Promega Corporation), and luminescence by firefly luciferase and *Renilla* luciferase was measured. The luminescence quantity of firefly luciferase was calibrated by the luminescence quantity of *Renilla* luciferase.

FIG. 10a shows results of Western blot when NEK6 was knockdown. It was shown that by using NEK6 siRNAs, the amount of NEK6 protein decreased, but the amount of SMAD3 protein did not change. FIG. 10b shows the luminescence quantity of firefly luciferase calibrated by that of *Renilla* luciferase when NEK6 was knockdown. By using NEK6 siRNAs, the luminescence quantity of firefly luciferase that is elevated by TGF-β was decreased. Consequently, it was shown that transcriptional activity of SMAD protein complex is suppressed by NEK6 knockdown.

Example 6: Influence on the Transcript Amounts of Fibrosis-Related Genes by NEK6 Knockdown In order to investigate that NEK6 knockdown exhibits therapeutic effect on fibrosis, the transcript amounts of fibrosis-related genes in cells transfected with NEK6 siRNAs were analyzed.

To human pulmonary fibroblast line LL29 cells established from the lung of an IPF patient, an siRNA for human NEK6 (ON-TARGET plus SMART pool siRNA, Dharmacon Inc.) was transfected using Lipofectamine RNAi MAX. 24 hours after transfection, the medium was changes from F-12K medium containing 10% FCS to F-12K medium containing 0.1% BSA. 48 hours after transfection, human TGF-β protein was added so as to provide a final concentration of 1 ng/mL. 72 hours after transfection, RNAs were extracted from the cells transfected with the siRNA, using RNeasy Mini Kit. The RNAs thus obtained were subjected to reverse transcription using High Capacity cDNA Reverse Transcription Kit to give cDNAs. The cDNAs thus obtained were subjected to real-time PCR using TaqMan Gene Expression Assays to detect influence on the transcript amounts of genes by NEK6 knockdown. The transcript amounts of Col1a1 gene and αSMA gene were calculated by dividing a measurement value in Col1a1 Taqman Probe (HS00164004_m1, Applied Biosystems®) or αSMA Taqman Probe (HS00426835_g1, Applied Biosystems®) by a measurement value in 18s Probe.

Figure 11:
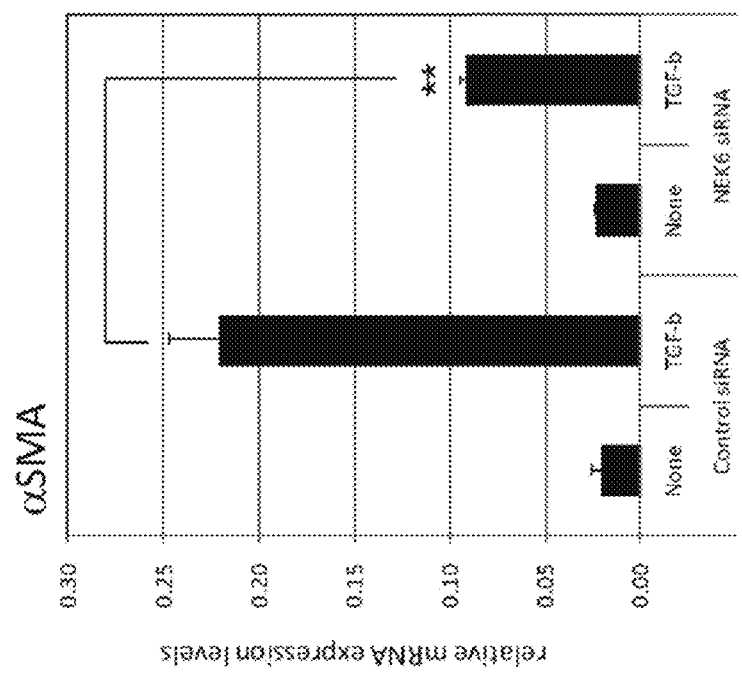
FIG. 11a shows the transcript amounts of Col1a1 gene when NEK6 was knockdown.
FIG. 11b shows the transcript amounts of αSMA gene when NEK6 was knockdown.
Figure 11:
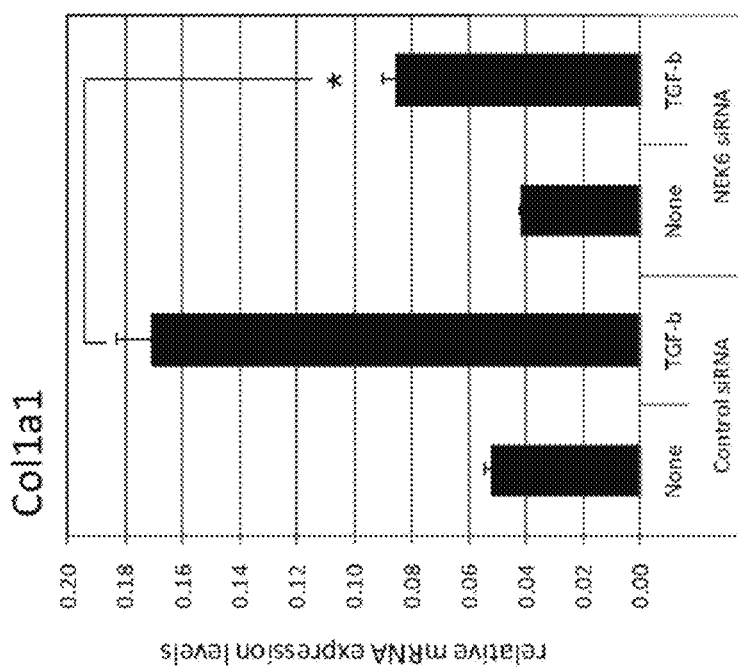

FIG. 11a shows the transcript amount of Col1a1 when NEK6 was knockdown, and FIG. 11b shows the transcript amount of αSMA gene when NEK6 was knockdown. By using NEK6 siRNAs, the transcript amounts of Col1a1 and αSMA genes that are elevated by TGF-β were decreased. Consequently, it was shown that NEK6 knockdown exhibits therapeutic effect on fibrosis.

Example 7: Synthesis of Single-Strand Nucleic Acid Molecules

The nucleic acid molecules shown below were synthesized on the basis of a phosphoroamidite method with a nucleic acid synthesizer (trade name: ABI3900 DNA Synthesizer, Applied Biosystems®). Solid-phase synthesis was performed using CPG (Controlled Pore Glass) as a solid-phase carrier, and EMM amidite (WO2013/027843) as RNA amidite. Excision from the solid-phase carrier and deprotection of a phosphate group protecting group, deprotection of a base protecting group, and deprotection of a 2'-hydroxyl group protecting group followed conventional methods. The synthesized single-strand nucleic acid molecules were purified by HPLC.

In the following single-strand nucleic acid molecules of the present invention, Lx is a linker region Lx and represents L-proline diamide amidite of the following structural formula.

[Chemical Formula 6]

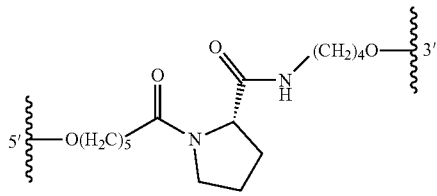

Additionally, underlines in the following single-strand nucleic acid molecules represent sequences that suppress NEK6 gene expression.

```
KB-001
                                   (SEQ ID NO: 31)
5'-GAGGGAGUUCCAACAACCUCUCC-Lx-

GGAGAGGUUGUUGGAACUCCCUCCA-3'

KB-002
                                   (SEQ ID NO: 32)
5'-CGAGGCAGGACUGUGUCAAGGCC-Lx-

GGCCUUGACACAGUCCUGCCUCGCC-3'

KB-003
                                   (SEQ ID NO: 33)
5'-CGUGGAGCACAUGCAUUCACGCC-Lx-

GGCGUGAAUGCAUGUGCUCCACGGC-3'

KB-004
                                   (SEQ ID NO: 34)
5'-GAUAAGAUGAAUCUCUUCUCCCC-Lx-

GGGGAGAAGAGAUUCAUCUUAUCUC-3'

KB-005
                                   (SEQ ID NO: 35)
5'-CAGAGACCUGACAUCGGAUACCC-Lx-

GGGUAUCCGAUGUCAGGUCUCUGGU-3'
```

Example 8: In Vitro Evaluation of ssPN Molecules (Single-Strand Nucleic Acid Molecules)

In vitro evaluation of the ssPN molecules (single-strand nucleic acid molecules) designed for NEK6 was performed. A measurement method for each item followed the aforementioned methods performed with ON-TARGET plus SMART pool siRNA and Stealth RNAi siRNA (Examples 1, 2, and 6). All ssPN nucleic acids of KB-001 to -005 suppressed the transcript amount of NEK6, and knocked down the target gene. Moreover, decrease in the amount of phosphorylated SMAD3 protein was confirmed by acting with ssPN nucleic acids of KB-001 to -005.

Figure 12:
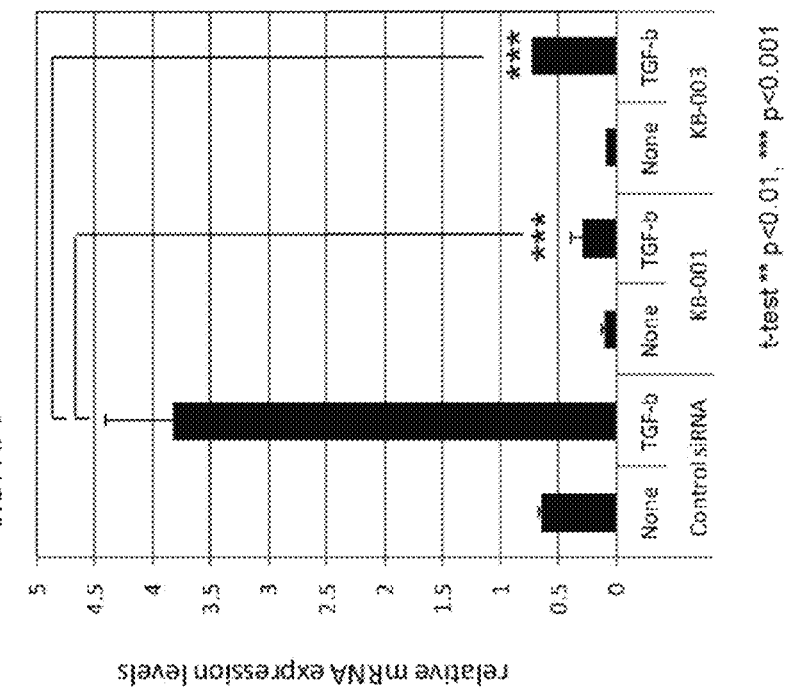
FIG. 12a shows the transcript amounts of Col1a1 gene when NEK6 was knockdown.
FIG. 12b shows the transcript amounts of αSMA gene when NEK6 was knockdown.
Figure 12:
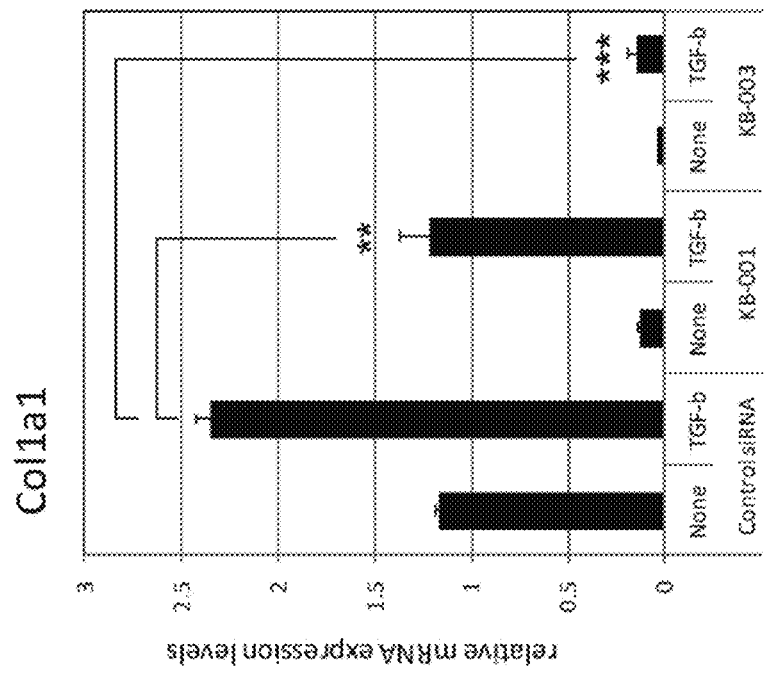

Additionally, results in which influence on the transcript amounts of fibrogenesis-related genes (Col1a1 and αSMA) was examined for KB-001 and KB-003 were shown in FIG. 12. FIG. 12a shows the transcript amounts of Col1a1 gene when KB-001 or KB-003 was acted, and FIG. 12b shows the transcript amounts of αSMA gene when KB-001 or KB-003 was acted. It was confirmed that both ssPN molecules of KB-001 and KB-003 suppresses the transcript amounts of fibrogenesis-related genes. From these results, it was possible to confirm fibrogenesis suppression action of the ssPN molecules (single-strand nucleic acid molecules) designed for NEK6.

Example 9: Verification of Anti-Fibrogenesis Action by In Vivo Knockdown of NEK6

In order to check that NEK6 knockdown exhibits therapeutic effect on fibrosis, NEK6 siRNAs are administered into a bleomycin pulmonary fibrogenesis model mouse to analyze anti-fibrogenesis action.

To a 7-weeks-old Crl:CD1 (ICR) mouse (Charles River Laboratories Japan, Inc.), bleomycin (Nippon Kayaku Co., Ltd.) is administered at a dose of 0.4 mg/kg by body weight to create a pulmonary fibrogenesis model mouse. NEK6 siRNAs are administered at a frequency of once 2 to 7 days at the maximum dose of 50 mg/kg body weight. During the term of administration of NEK6 siRNAs, diagnostic imaging is performed at a frequency of once a week with a micro CT for experimental animal use. Days 14 to 30 after the initial administration of NEK6 siRNAs, dissection is performed to resect the lung. Measurements of the transcript amounts of fibrosis-related genes and the expression amounts of fibrosis-related proteins, pathological analysis, and the like using the resected lung are performed. With these, it is possible to confirm that fibrogenesis is suppressed in a NEK6 siRNA administration group compared to a NEK6 siRNA unadministration group, and to show anti-fibrogenesis action of NEK6 siRNAs in a pulmonary fibrogenesis model mouse.

Example 10: Influence of NEK6 siRNAs on SMAD3 Protein Phosphorylation in Hepatic Stellate Cells In order to investigate possibility that NEK6 protein may control TGF-β signal in hepatic stellate cells, the amount of phosphorylated SMAD3 was analyzed in cells transfected with NEK6 siRNAs.

Human primary hepatic stellate cells isolated from human liver (ScienCell Research Laboratories, Inc.) was cultured on a poly-L-lysine (PLL) coated cell culture dish for 5 days. Then, siRNAs for human NEK6 (KB-004) were transfected using Lipofectamine RNAi MAX (Invitrogen™). 48 hours after transfection, the medium was changed from stellate cell medium (ScienCell Research Laboratories, Inc.) containing 2% FCS and 1% Stellate cell growth supplement (SteCGS, ScienCell Research Laboratories, Inc.) to stellate cell medium containing 0.2% FCS and 1% SteCGS. 72 hours after transfection, lipopolysaccharide (LPS, Sigma-Aldrich Co. LLC.) was added to the medium so as to provide a final concentration of 100 ng/mL. Eleven and half hours after addition of LPS, human TGF-β protein (PeproTech, Inc.) was added so as to provide a final concentration of 5 ng/mL. Thirty minutes after addition of TGF-β, the cells were lysed with 2×SDS sample buffer (100 mM Tris-HCl, pH 6.8, 4% SDS, 6 M Urea, 12% Glycerol, 2% protease inhibitor cocktail [Nacalai Tesque Inc.], 1% phosphatase inhibitor cocktail [Nacalai Tesque Inc.]) to give a cell extract.

To the cell extract thus obtained, β-Mercaptoethanol and Bromophenol blue were added so as to provide final concentrations of 5% and 0.025%, respectively, and then heated at 95° C. for 4 minutes to give a sample. Using the sample thus obtained, SDS-PAGE was performed to separate proteins contained in the sample in accordance with their sizes. Then, the separated proteins were transferred onto a PVDF membrane, and subjected to Western blotting with an anti-phosphorylated SMAD3 antibody (Cell Signaling Technology, Inc.) and an anti-SMAD3 antibody (Cell Signaling Technology, Inc.), an anti-phosphorylated SMAD2 antibody (Cell Signaling Technology, Inc.) and an anti-SMAD2 antibody (Cell Signaling Technology, Inc.), an anti-NEK6 antibody (Santa Cruz Biotechnology Inc.), and an anti-Vinculin antibody (Sigma-Aldrich Co. LLC.).

Figure 13:
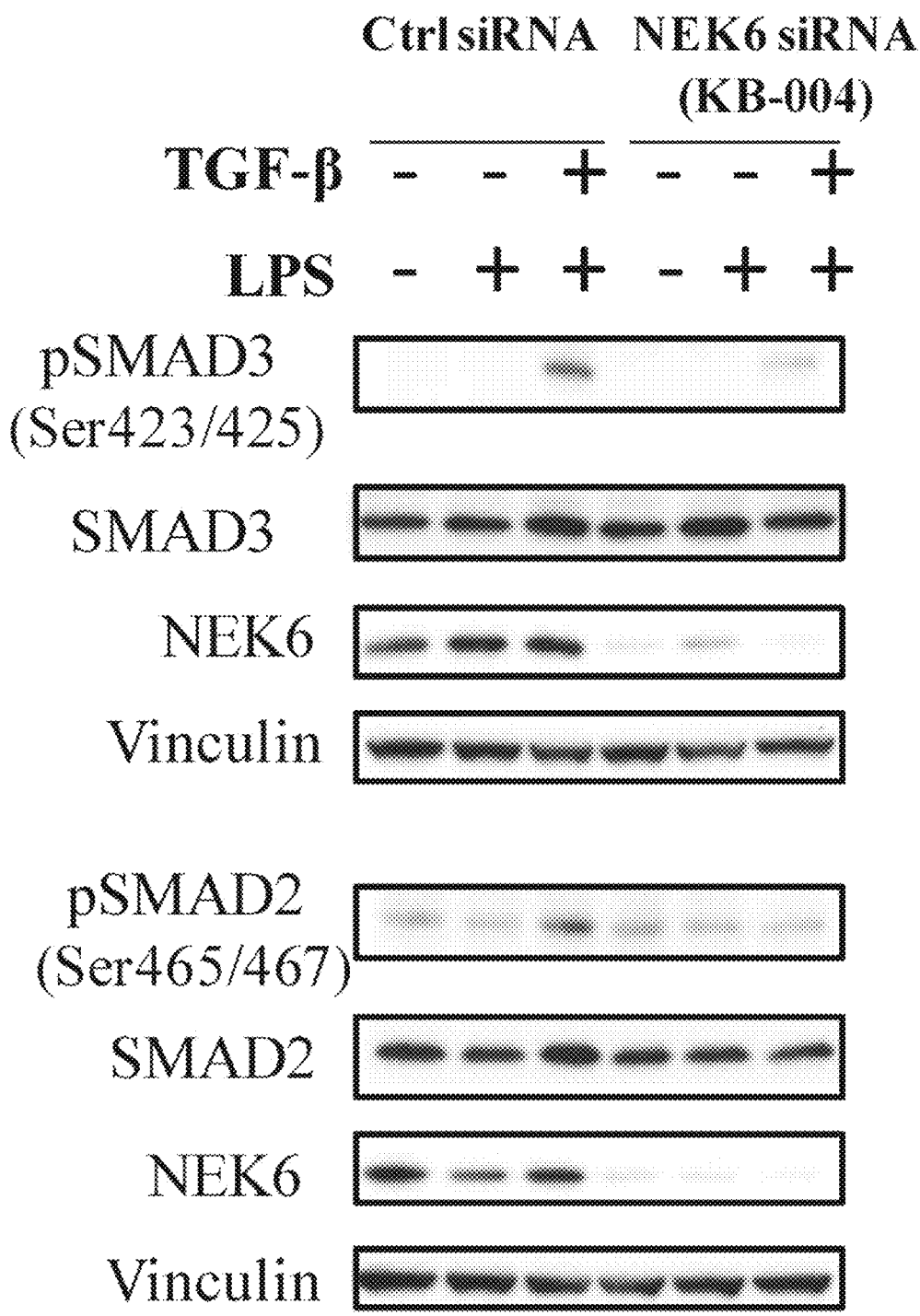
FIG. 13 represents results of Western blot for phosphorylated SMAD3 protein (pSMAD3) when NEK6 siRNAs were introduced into hepatic stellate cells.

FIG. 13 shows results of Western blotting of phosphorylated SMAD3 protein and phosphorylated SMAD2 protein when NEK6 siRNAs were transfected. By NEK6 siRNAs, the amount of NEK6 protein was decreased and the amounts of phosphorylated SMAD3 and phosphorylated SMAD2 that are elevated by TGF-β were decreased. Consequently, it was shown that phosphorylation of SMAD3 protein and SMAD2 protein is suppressed by NEK6 knockdown.

Example 11: Suppression of SMAD3 Phosphorylation by NEK6 siRNAs in Hepatic Stellate Cells In order to investigate possibility that NEK6 protein may also controls TGF-β signal, the amount of phosphorylated SMAD3 was analyzed in cells transfected with each NEK6 siRNA.

Human primary hepatic stellate cells isolated from human liver was cultured on a PLL coated cell culture dish for 5 days. Then, various siRNAs for human NEK6 (KB-006, KB-004, KB-011, KB-005, KB-010 were transfected using Lipofectamine RNAi MAX. 48 hours after transfection, the medium was changed from stellate cell medium containing 2% FCS and 1% SteCGS to stellate cell medium containing 0.2% FCS and 1% SteCGS. 72 hours after transfection, LPS was added to the medium so as to provide a final concentration of 100 ng/ml. Eleven and half hours after addition of LPS, human TGF-β protein was added so as to provide a final concentration of 5 ng/ml. Thirty minutes after addition of TGF-β, the cells were lysed with 2×SDS sample buffer (100 mM Tris-HCl, pH 6.8, 4% SDS, 6 M Urea, 12% Glycerol, 2% protease inhibitor cocktail [Nacalai Tesque Inc.], 1% phosphatase inhibitor cocktail [Nacalai Tesque Inc.]) to give a cell extract. To the cell extract thus obtained, β-Mercaptoethanol and Bromophenol blue were added so as to provide final concentrations of 5% and 0.025%, respectively, and then heated at 95° C. for 4 minutes to give a sample. Using the sample thus obtained, SDS-PAGE was performed to separate proteins contained in the sample in accordance with their sizes. Then, the separated proteins were transferred onto a PVDF membrane, and subjected to Western blotting with an anti-phosphorylated SMAD3 antibody and an anti-SMAD3 antibody, an anti-NEK6 antibody, and an anti-Vinculin.

Figure 14:
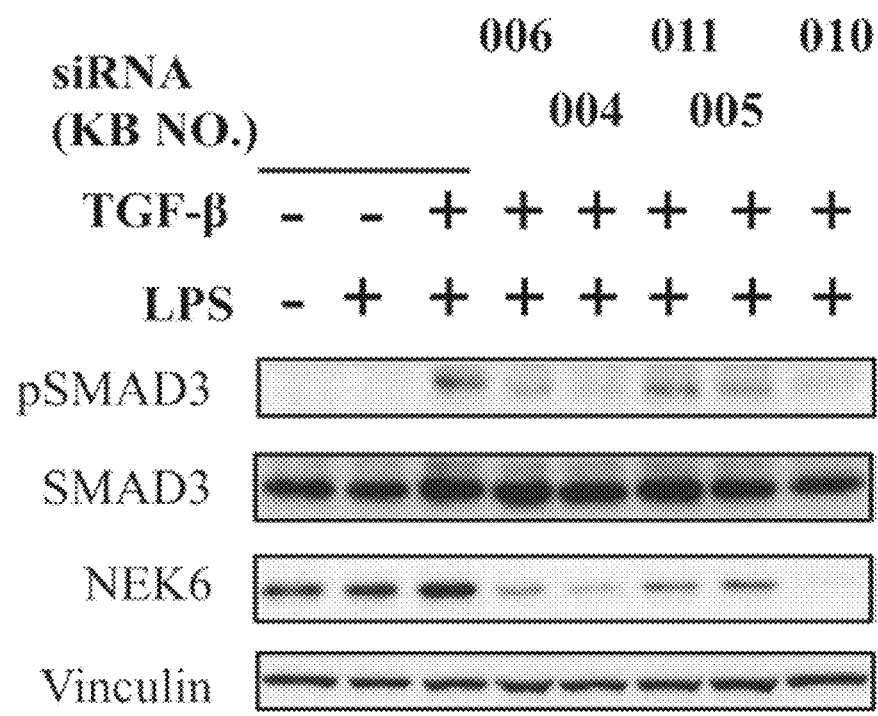
FIG. 14 represents results of Western blot for phosphorylated SMAD3 protein (pSMAD3) when various NEK6 siRNAs were introduced into hepatic stellate cells.

FIG. 14 shows results of Western blotting of phosphorylated SMAD3 protein when NEK6 was knockdown by various kinds of NEK6 siRNAs. By introduction of various kinds of the NEK6 siRNAs, the amount of NEK6 protein was decreased, and the amount of phosphorylated SMAD3 that is elevated by TGF-β was decreased. Consequently, it was shown that phosphorylation of SMAD3 protein is suppressed by NEK6 knockdown by using a plurality of NEK6 siRNA sequences.

Example 12: Influence of NEK6 siRNAs on Fibrosis-Related Genes in Hepatic Stellate Cells In order to investigate that NEK6 knockdown exhibits an efficacy against fibrosis, the amounts of fibrosis-related genes were analyzed in cells transfected with NEK6 siRNAs.

Human primary hepatic stellate cells isolated from human liver was cultured on a PLL coated cell culture dish for 5 days. Then, siRNAs for human NEK6 (KB-004) were transfected using Lipofectamine RNAi MAX. 48 hours after transfection, the medium was changed from stellate cell medium containing 2% FCS and 1% Stellate cell growth supplement to stellate cell medium containing 0.2% FCS and 1% SteCGS. 72 hours after transfection, LPS was added to the medium so as to provide a final concentration of 100 ng/ml. Eleven and half hours after addition of LPS, human TGF-β protein was added so as to provide a final concentration of 5 ng/ml. 24 hours after addition of TGF-β, RNAs were extracted from the cells transfected with KB-004, using RNeasy Mini Kit. The RNAs thus obtained were subjected to reverse transcription using High Capacity cDNA Reverse Transcription Kit to give cDNAs. The cDNAs thus obtained were subjected to real-time PCR using TaqMan Gene Expression Assays to detect influence on the transcript amounts of genes by NEK6 knockdown. The transcript amounts of NEK6 gene, Fibronectin gene, and αSMA gene were calculated by dividing a measurement value in NEK6 Taqman Probe (HS00205221_m1, Applied Biosystems®), a measurement value in Fibronectin Taqman Probe (HS01549976_m1, Applied Biosystems®), or a measurement value in αSMA Taqman Probe (HS00426835_g1, Applied Biosystems®) by a measurement value of 18s Probe.

FIG. 15a shows the transcript amount of NEK6 when NEK6 was knockdown, FIG. 15b shows the transcript amount of Fibronectin when NEK6 was knockdown, and FIG. 15c shows the transcript amount of αSMA gene when NEK6 was knockdown. By NEK6 siRNAs, the transcript amounts of Fibronectin and αSMA genes that are elevated TGF-β were decreased. Consequently, it was shown that NEK6 knockdown suppresses fibrogenesis.

Example 13: Influence of NEK6 siRNAs on SMAD3 Protein Phosphorylation in Kidney Fibroblast In order to investigate possibility that NEK6 protein may control TGF-β signal, the amount of phosphorylated SMAD3 was analyzed in cells transfected with NEK6 siRNAs.

To rat kidney fibroblast line NRK-49F cells, siRNAs for human NEK6 (KB-004) were transfected using Lipofectamine RNAi MAX. 24 hours after transfection, the medium was changed from DMEM medium containing 10% FCS to DMEM medium containing 0.1% FCS. 48 hours after transfection, human TGF-β protein was added so as to provide a final concentration of 5 ng/ml. Thirty minutes or an hour after addition, the cell were lysed with 2×SDS sample buffer (100 mM Tris-HCl, pH 6.8, 4% SDS, 6 M Urea, 12% Glycerol, 2% protease inhibitor cocktail, 1% phosphatase inhibitor cocktail) to give a cell extract. To the cell extract thus obtained, β-Mercaptoethanol and Bromophenol blue were added so as to provide final concentrations of 5% and 0.025%, respectively, and then heated at 95° C. for 4 minutes to give a sample. Using the sample thus obtained, SDS-PAGE was performed to separate proteins contained in the sample in accordance with their sizes. Then, the separated proteins were transferred onto a PVDF membrane, and subjected to Western blotting with an anti-phosphorylated SMAD3 antibody and an anti-SMAD3 antibody, an anti-NEK6 antibody (Abcam plc.), and an anti-Vinculin antibody.

Figure 16:
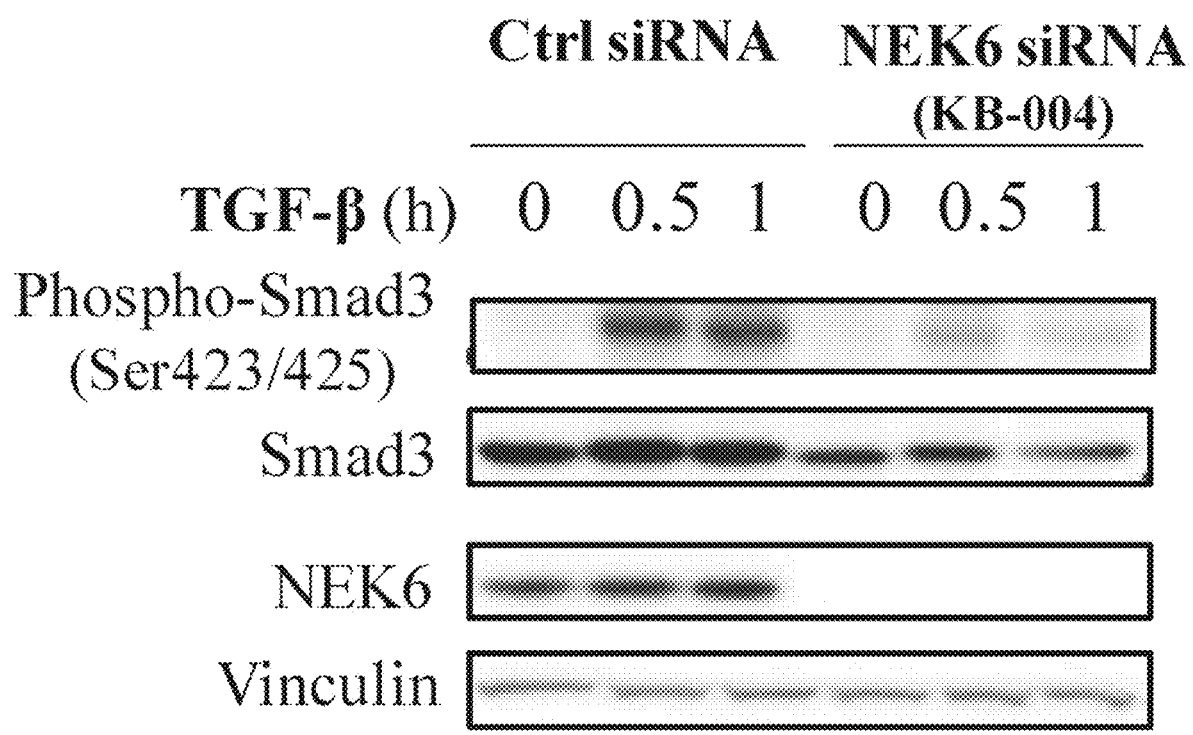
FIG. 16 represents results of Western blotting for phosphorylated SMAD3 protein when NEK6 was knockdown in kidney fibroblasts.

FIG. 16 shows results of Western blotting of phosphorylated SMAD3 protein when NEK6 was knockdown. By using NEK6 siRNAs, the amount of NEK6 protein was decreased, and the amount of phosphorylated SMAD3 that is elevated by TGF-β was decreased. Consequently, it was shown that SMAD3 protein phosphorylation is suppressed by NEK6 knockdown.

Example 14: Evaluation of Efficacy of NEK6 siRNAs in Carbon Tetrachloride ($CCl_4$)-Induced Hepatic Fibrogenesis Models In order to check that NEK6 knockdown exhibits efficacy against fibrosis, NEK6 siRNAs were intravenously administered into $CCl_4$ model mice and subjected to analysis of anti-fibrogenesis action.

To 7-weeks-old male C57BL/6J mice (Charles River Laboratories Japan, Inc.), olive oil solution containing 10 v/v % $CCl_4$ (FUJIFILM Wako Pure Chemical Corporation) was intraperitoneally administered at 10 mL/kg by body weight on day 0, 4, 7, and 11 to create hepatic fibrogenesis model mice. Grouping was performed with body weight at the day before the initial administration of $CCl_4$, and the design of the groups was as a saline administration group not receiving $CCl_4$ (n=5), a solvent-administration group receiving $CCl_4$ (n=10), and nucleic acid administration group receiving $CCl_4$ (n=10). Using KB-004 as NEK6 siRNAs and Invivofectamine 3.0 Reagent (Thermo Fisher Scientific Inc.) as an administration solvent, 0.3 mg/mL of nucleic acid administration solution was made according to the product protocol of Invivofectamine 3.0. For the nucleic acid administration group, the nucleic acid administration solution containing KB-004 was administered via tail vein so as to provide 3 mg/kg by body weight; and for the solvent administration group, the administration solvent in an equal amount to that of the nucleic acid administration group was administered via tail vein on the day before the initial administration of $CCl_4$ and day 10 after induction of pathology. Evaluation of hepatic disorder and fibrogenesis was performed on day 13 after induction of pathology (Examples 15, 16, 17, and 19).

Example 15: Analysis of Hepatic Disorder Markers in $CCl_4$ Models

Fibrogenesis has been understood as an excessive wound healing process against disorder of a cell or tissue. Thus, suppression of disorder of a cell or tissue along with fibrogenesis has been considered to be effective for treatment of various fibrosis. Then, in order to investigate whether NEK6 knockdown would exhibit effect on hepatic disorder, measurement of hepatic disorder markers in $CCl_4$ models was performed.

On day 13 after induction of pathology, blood draw was performed from tail vein using a plane capillary blood-sampling tube, and subjected to standing for 30 minutes or more. The post-standing blood was centrifuged to obtain serum. Serum glutamic pyruvic transaminase (GPT) and glutamic oxaloacetic transaminase (GOT) were measured using Transaminase CII-test Wako (Wako Pure Chemical Industries, Ltd.). Measurement method followed the instruction of the reagent.

FIG. 17a has shown measurement results of serum GPT, and FIG. 17b has shown measurement results of serum GOT. Elevation of serum GPT and GOT found in $CCl_4$ models was suppressed by administering NEK6 siRNAs. Consequently, it was shown that NEK6 knockdown suppresses hepatic disorder.

Example 16: Analysis of SMAD3 Protein Phosphorylation in $CCl_4$ Models

In order to investigate whether NEK6 knockdown would exhibit effect on SMAD3 protein phosphorylation, the amount of phosphorylated SMAD3 in $CCl_4$ models was analyzed.

A liver collected on day 13 after induction of pathology was frozen and grinded to be powdery. To the powdery liver, lysis buffer (150 mM NaCl, 1% NP40, 0.1% SDS, 50 mM Tris-HCl, pH7.5, 1 mM EDTA, 1 mM Benzylsulfonyl fluoride, 2% protease inhibitor cocktail, 1% phosphatase inhibitor cocktail) was added, and an organ extract was prepared using a handy ultrasonic generator. To the supernatant obtained by centrifuging the organ extract, β-Mercaptoethanol and Bromophenol blue were added so as to provide final concentrations of 5% and 0.025%, respectively. Then, heating was made at 95° C. for 4 minutes to give a sample. Using the sample thus obtained, SDS-PAGE was performed to separate proteins contained in the sample in accordance with their sizes. Then, the separated proteins were transferred onto a PVDF membrane, and subjected to Western blotting with an anti-phosphorylated SMAD3 antibody (Abcam plc.) and an anti-SMAD3 antibody, an anti-NEK6 antibody (Abcam plc.), and an anti-Vinculin antibody. Phosphorylated SMAD3 was calibrated by the total SMAD3 amount.

Figure 18:
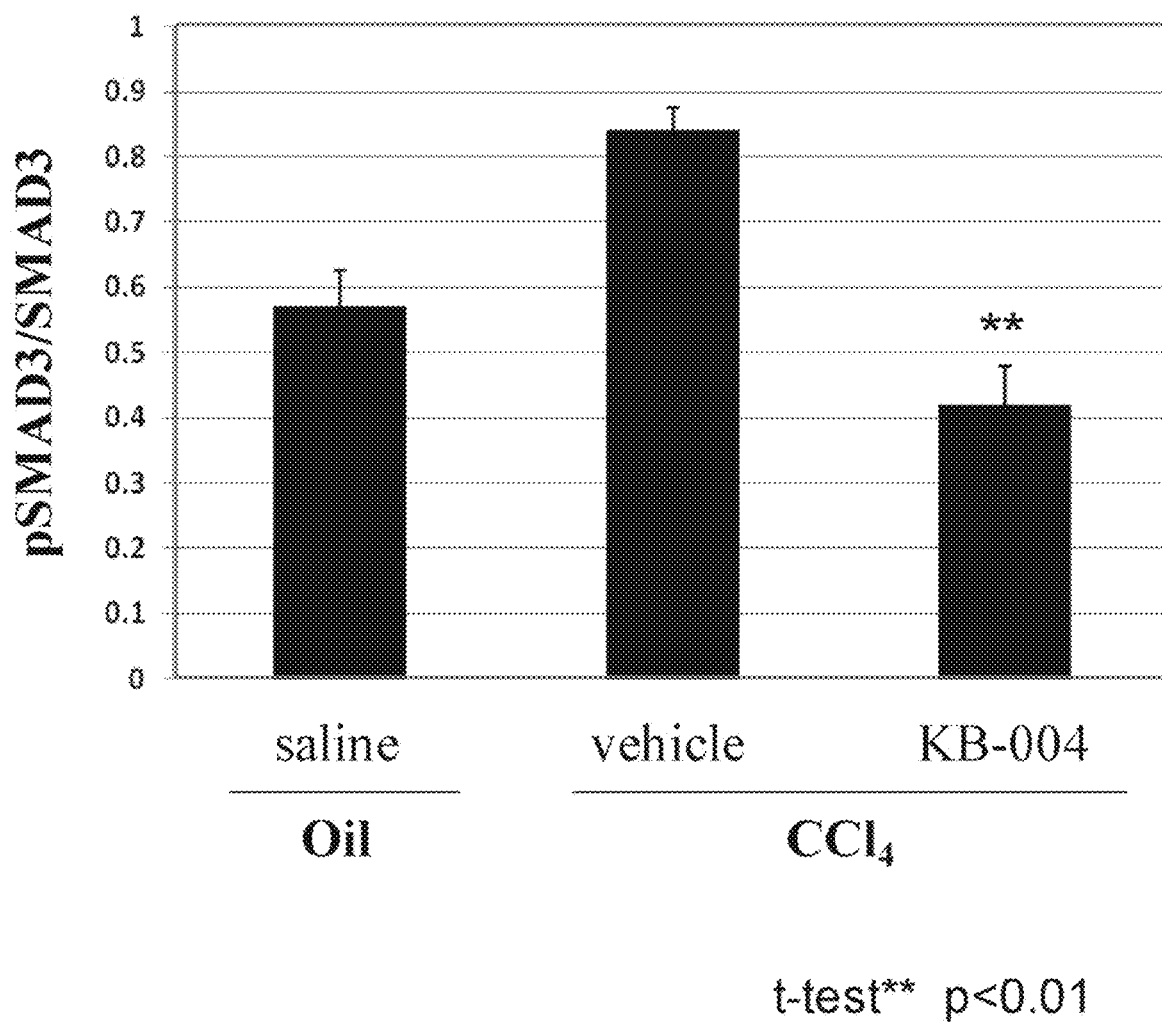
FIG. 18 represents results of Western blotting for phosphorylated SMAD3 protein when NEK6 was knockdown in $CCl_4$ models.

FIG. 18 shows results of Western blotting of phosphorylated SMAD3 protein when NEK6 was knockdown. By using NEK6 siRNAs, the amount of NEK6 protein was decreased, and the amount of phosphorylated SMAD3 that is elevated by TGF-β was decreased. Consequently, it was shown that NEK6 knockdown suppresses SMAD3 protein phosphorylation in the liver of a $CCl_4$ model.

Example 17: Analysis of Fibrosis-Related Genes in $CCl_4$ Models

In order to investigate whether NEK6 knockdown would exhibit efficacy against fibrogenesis, the transcript amounts of fibrosis-related genes in $CCl_4$ models were analyzed.

RNAs were extracted from a liver collected on day 13 after induction of pathology, using QIAzol Lysis reagent (QIAGEN N.V). Subsequently, RNAs were purified using RNeasy mini kit, and subjected to reverse transcription reaction using High-Capacity cDNA Reverse Transcription Kit. The transcript amounts of NEK6 Taqman Probe (Mm00480730_m1, Applied Biosystems®); and Col1a1 Taqman Probe (Mm00801666_g1, Applied Biosystems®), Col3a1 Taqman Probe (Mm01254476_m1, Applied Biosystems®), and Timp1 Taqman Probe (Mm01341361_m1, Applied Biosystems®) as fibrosis-related genes were measured using TaqMan Gene Expression Assay, and relative ratios to the transcript amount of 18s rRNA Taqman Probe (Hs99999901_s1, Applied Biosystems®), which is an inner control, is defined as the transcript amount of each gene.

The transcript amounts of each gene in $CCl_4$ models are shown in FIGS. 19a-d. The transcript amount of NEK6 gene decreased by administration of NEK6 siRNAs. From this, it was shown that KB-004 used suppressed efficiently target gene transcription. At this time, the transcript amounts of fibrosis-related genes (Col1a1, Col3a1, Timp1) that are derived by induction of pathology significantly decreased. Consequently, it was shown that NEK6 knockdown suppresses fibrogenesis.

Example 18: Analysis of Fibrosis-Related Genes in Bile Duct Ligation-Induced Hepatic Fibrogenesis (BDL) Models In order to investigate that NEK6 knockdown exhibits efficacy against fibrosis, NEK6 siRNAs were intravenously administered into bile duct ligation-induced hepatic fibrogenesis model mice (BDL models) to analyze the transcript amounts of fibrosis-related genes.

Nine-weeks-old C57BL/6J mice (Charles River Laboratories Japan, Inc.) were grouped in accordance with body weight, and KB-004 solution (0.3 mg/mL) prepared according to the package insert of the gene transfer reagent Invivofectamine 3.0 (Thermo Fisher Scientific Inc.) was administered via tail vein at a dose of 3 mg/kg by body weight (n=12). For a control group, only solvent was administered (n=15). The next day of administration, the common bile duct was ligated at two points to create a hepatic fibrogenesis model mouse. For a sham-operated group, saline (Otsuka Normal Saline) was administered via tail vein, and only detachment of the common bile duct was performed (n=7). A liver was collected on day 14 after bile duct ligation; and the transcript amounts of NEK6 Taqman Probe (Mm00480730_m1, Applied Biosystems®), and Col1a1 Taqman Probe (Mm00801666_g1, Applied Biosystems®), Col3a1 Taqman Probe (Mm01254476_m1, Applied Biosystems®), and Timp1 Taqman Probe (Mm01341361_m1, Applied Biosystems®) as fibrosis-related genes were measured in a similar manner as described above, and relative ratios to the transcript amount of GAPDH Taqman Probe (Mm9999995_g1, Applied Biosystems®), which is an inner control, is defined as the transcript amount of each gene.

Each gene transcript amount in BDL models are shown in FIGS. 20 a-d. The transcript amount of NEK6 gene decreased by administration of NEK6 siRNAs. From this, it was shown that KB-004 used suppressed efficiently target gene transcription. At this time, the transcript amounts of fibrosis-related genes (Col1a1, Col3a1, Timp1) that are derived by induction of pathology significantly decreased. Consequently, it was shown that NEK6 knockdown suppresses fibrogenesis.

Example 19: Pathological Analysis in $CCl_4$ Models

In order to investigate whether NEK6 knockdown would exhibit effect against a $CCl_4$-induced hepatic fibrogenesis model, observation of histopathology was performed.

The inner right lobe of a liver was collected on day 13 after induction of pathology, and fixed with 10% neutral buffered formalin solution. After embedding with paraffin, tissue sections were made and subjected to hematoxylin-eosin staining.

Figure 21:
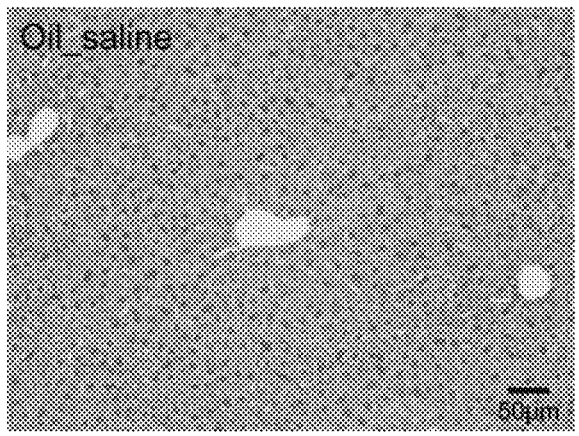
FIG. 21 represents results of pathological analysis of the liver when NEK6 was knockdown in $CCl_4$ models.
Figure 21:
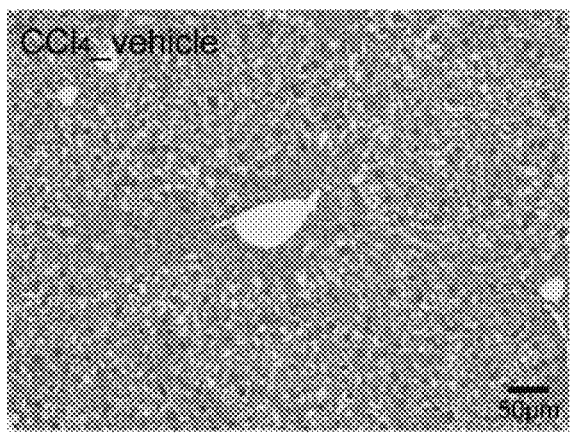
Figure 21:
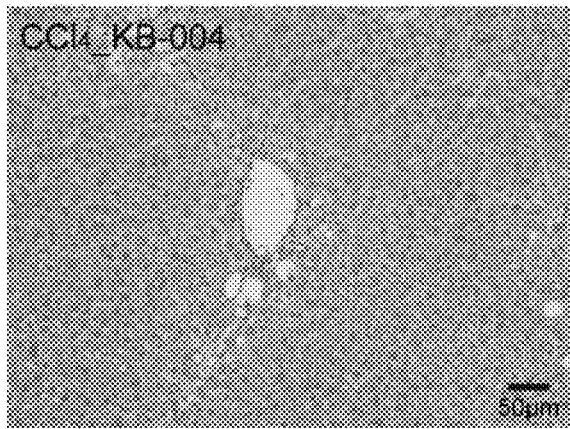

FIG. 21 shows representative examples of histopathology. FIG. 21a represents results of the saline administration group not receiving $CCl_4$, FIG. 21b represents results of the solvent administration group receiving $CCl_4$, and FIG. 21c represents results of the nucleic acid administration group receiving $CCl_4$. Vacuolar degeneration numerously found in FIG. 21b indicates cell disorder, and an area that is abundantly present around the central part and in which the nucleuses are not stained indicates cell necrosis. Disorder, necrosis, and the like of cells found in a liver tissue of a $CCl_4$ model were decreased by administering NEK6 siRNAs. Consequently, it was shown that NEK6 knockdown suppresses change of histopathology in a $CCl_4$-induced hepatic fibrogenesis model.

INDUSTRIAL APPLICABILITY

According to the present invention, a novel phosphorylation inhibitor of SMAD2/3 protein and a therapeutic agent for fibrosis can be provided.

The invention claimed is:

1. A method for treating fibrosis, comprising:
 administering to a subject in need thereof a therapeutically-effective amount of a nucleic acid molecule having a guide strand and a passenger strand,
 wherein the number of nucleotides in the guide strand and in the passenger strand are each 19- to 50-nt, and
 wherein the guide strand includes a sequence suppressing expression, the sequence suppressing expression being complementary to NEK6 gene, to thereby suppress NEK6 gene expression.

2. The method according to claim 1, wherein the nucleic acid molecule is a single-strand nucleic acid molecule forming a hairpin RNA structure.

3. The method according to claim 1, wherein the guide strand forms an overhanging end.

4. The method according to claim 1, wherein the fibrosis is pulmonary fibrosis, hepatic fibrosis, or kidney fibrosis.

5. The method according to claim 1, wherein the number of nucleotides in the guide strand and in the passenger strand are each 19- to 30-nt.

6. The method according to claim 1, wherein the number of nucleotides in the guide strand and in the passenger strand are each 19- to 25-nt.

7. The method according to claim 1, wherein the number of nucleotides in the guide strand and in the passenger strand are each 19- to 23-nt.

* * * * *